United States Patent
De Szalay

(10) Patent No.: US 9,707,162 B2
(45) Date of Patent: Jul. 18, 2017

(54) MICROBICIDAL PERSONAL CARE COMPOSITIONS COMPRISING METAL IONS

(71) Applicant: Reckitt & Colman (Overseas) Limited, Slough, Berkshire (GB)

(72) Inventor: Sarah Frances De Szalay, West Milford, NJ (US)

(73) Assignee: RECKITT & COLMAN (OVERSEAS) LIMITED, Slough, Berkshire (GB)

( * ) Notice: Subject to any disclaimer, the term of this patent is extended or adjusted under 35 U.S.C. 154(b) by 0 days.

(21) Appl. No.: 14/646,825

(22) PCT Filed: Nov. 27, 2013

(86) PCT No.: PCT/GB2013/053129
§ 371 (c)(1),
(2) Date: May 22, 2015

(87) PCT Pub. No.: WO2014/083330
PCT Pub. Date: Jun. 5, 2014

(65) Prior Publication Data
US 2016/0158122 A1    Jun. 9, 2016

Related U.S. Application Data

(60) Provisional application No. 61/731,769, filed on Nov. 30, 2012.

(51) Int. Cl.
| | | |
|---|---|---|
| A61K 8/19 | (2006.01) | |
| A61K 8/34 | (2006.01) | |
| A61K 8/36 | (2006.01) | |
| A61K 8/365 | (2006.01) | |
| A61K 8/20 | (2006.01) | |
| A61K 8/23 | (2006.01) | |
| A61Q 17/00 | (2006.01) | |
| A01N 33/12 | (2006.01) | |
| A61K 8/41 | (2006.01) | |
| A61K 8/27 | (2006.01) | |
| A01N 31/02 | (2006.01) | |

(52) U.S. Cl.
CPC ............... *A61K 8/19* (2013.01); *A01N 31/02* (2013.01); *A01N 33/12* (2013.01); *A61K 8/20* (2013.01); *A61K 8/23* (2013.01); *A61K 8/27* (2013.01); *A61K 8/34* (2013.01); *A61K 8/345* (2013.01); *A61K 8/36* (2013.01); *A61K 8/365* (2013.01); *A61K 8/416* (2013.01); *A61Q 17/005* (2013.01)

(58) Field of Classification Search
CPC ... A61K 8/19; A61K 8/34; A61K 8/27; A61K 8/416; A61K 8/20; A61K 8/23; A61K 8/345; A61K 8/36; A61K 8/365; A61Q 17/005; A01N 31/02; A01N 2300/00; A01N 59/16; A01N 59/20; A01N 33/12
See application file for complete search history.

(56) References Cited

U.S. PATENT DOCUMENTS

| | | |
|---|---|---|
| 2,118,225 A | 5/1938 | Pierce |
| 3,282,776 A | 11/1966 | Kitzke et al. |
| 3,835,057 A | 9/1974 | Cheng et al. |
| 4,098,602 A | 7/1978 | Seymour et al. |
| 4,198,296 A | 4/1980 | Doumas et al. |
| 4,407,818 A | 10/1983 | Lionelle et al. |
| 4,477,438 A | 10/1984 | Willcockson et al. |
| 4,647,458 A | 3/1987 | Ueno et al. |
| 4,654,213 A | 3/1987 | Ramirez et al. |
| 4,678,658 A | 7/1987 | Casey et al. |
| 4,695,453 A | 9/1987 | Tuominen et al. |

(Continued)

FOREIGN PATENT DOCUMENTS

| | | |
|---|---|---|
| EP | 0079579 A1 | 5/1983 |
| EP | 0099209 A1 | 1/1984 |

(Continued)

OTHER PUBLICATIONS

International Search Report for PCT/GB2013/053129 dated Apr. 11, 2014.

(Continued)

*Primary Examiner* — Aradhana Sasan
(74) *Attorney, Agent, or Firm* — Norris McLaughlin & Marcus PA

(57) ABSTRACT

Animate surface treatment compositions comprise (or in certain preferred embodiments may consist essentially of, or may consist of): a metal ion source material which releases copper ions and/or zinc ions into the treatment composition, in certain embodiments at least one alcohol which independently of other constituents present exhibits a microbicidal effect, in certain embodiments at least one quaternary ammonium compound which provides a microbicidal benefit, optionally but very preferably also at least one detersive surfactant, further optionally one or more further constituents which impart one or more advantageous technical or aesthetic benefits to the compositions, including one or more detersive surfactants, and water, wherein the compositions are at a pH such that the animate surface treatment compositions, exhibit a microbicidal or germicidal or antimicrobial effect on treated surfaces, which compositions are characterized in exhibiting a microbicidal benefit when tested against one or more challenge microorganisms according to one or more standardized test protocols.

20 Claims, No Drawings

(56) References Cited

U.S. PATENT DOCUMENTS

| | | |
|---|---|---|
| 4,714,563 A | 12/1987 | Kajs et al. |
| 4,793,988 A | 12/1988 | Casey et al. |
| 4,800,235 A | 1/1989 | La Marre et al. |
| 4,952,398 A | 8/1990 | Tapin |
| RE33,465 E | 11/1990 | Eby, III |
| 4,992,212 A | 2/1991 | Corring et al. |
| 5,043,357 A | 8/1991 | Hoeffler et al. |
| 5,064,635 A | 11/1991 | Casey |
| 5,174,990 A | 12/1992 | Douglas |
| 5,180,749 A | 1/1993 | Cusack et al. |
| 5,208,031 A | 5/1993 | Kelly |
| 5,227,156 A | 7/1993 | Wiese |
| 5,348,731 A | 9/1994 | Patti et al. |
| 5,358,979 A | 10/1994 | van Hoboken et al. |
| 5,364,649 A | 11/1994 | Rossmoore et al. |
| 5,373,025 A | 12/1994 | Gay |
| 5,403,587 A | 4/1995 | McCue et al. |
| 5,429,819 A | 7/1995 | Oka et al. |
| 5,645,846 A | 7/1997 | Oka et al. |
| 5,668,097 A | 9/1997 | Trinh et al. |
| 5,670,475 A | 9/1997 | Trinh et al. |
| 5,696,169 A | 12/1997 | Otsu et al. |
| 5,728,404 A | 3/1998 | von Rheinbaben et al. |
| 5,731,282 A | 3/1998 | Duquesne |
| 5,780,064 A | 7/1998 | Meisters et al. |
| 5,783,544 A | 7/1998 | Trinh et al. |
| 5,798,121 A | 8/1998 | Cauwet et al. |
| 5,827,511 A | 10/1998 | Campbell et al. |
| 5,837,664 A | 11/1998 | Black |
| 5,859,064 A | 1/1999 | Cronce et al. |
| 5,908,854 A | 6/1999 | McCue et al. |
| 5,939,060 A | 8/1999 | Trinh et al. |
| 5,948,741 A | 9/1999 | Ochomogo et al. |
| 5,948,742 A | 9/1999 | Chang et al. |
| 5,968,539 A | 10/1999 | Beerse et al. |
| 6,022,545 A | 2/2000 | Schmittmann et al. |
| 6,046,146 A | 4/2000 | Erilli |
| 6,077,318 A | 6/2000 | Trinh et al. |
| 6,080,387 A | 6/2000 | Zhou et al. |
| 6,106,851 A | 8/2000 | Beerse et al. |
| 6,107,261 A | 8/2000 | Taylor et al. |
| 6,113,933 A | 9/2000 | Beerse et al. |
| 6,136,771 A | 10/2000 | Taylor et al. |
| 6,136,776 A | 10/2000 | Dickler et al. |
| 6,183,757 B1 | 2/2001 | Beerse et al. |
| 6,183,763 B1 | 2/2001 | Beerse et al. |
| 6,190,674 B1 | 2/2001 | Beerse et al. |
| 6,190,675 B1 | 2/2001 | Beerse et al. |
| 6,190,764 B1 | 2/2001 | Shi et al. |
| 6,197,315 B1 | 3/2001 | Beerse et al. |
| 6,214,784 B1 | 4/2001 | Robbins et al. |
| 6,239,096 B1 | 5/2001 | Blum et al. |
| 6,242,009 B1 | 6/2001 | Batarseh et al. |
| 6,245,728 B1 | 6/2001 | Robbins et al. |
| 6,248,135 B1 | 6/2001 | Trinh et al. |
| 6,258,368 B1 | 7/2001 | Beerse et al. |
| 6,268,327 B1 | 7/2001 | Lu et al. |
| 6,277,805 B1 | 8/2001 | Kupneski |
| 6,294,186 B1 | 9/2001 | Beerse et al. |
| 6,339,056 B1 | 1/2002 | Like |
| 6,344,218 B1 | 2/2002 | Dodd et al. |
| 6,346,281 B1 | 2/2002 | DeAth et al. |
| 6,376,448 B1 | 4/2002 | Colurciello, Jr. et al. |
| 6,387,874 B1 | 5/2002 | Schalitz et al. |
| 6,444,707 B1 | 9/2002 | Lampe et al. |
| 6,451,065 B2 | 9/2002 | Trinh et al. |
| 6,468,953 B1 | 10/2002 | Hitchems et al. |
| 6,482,392 B1 | 11/2002 | Zhou et al. |
| 6,482,788 B1 | 11/2002 | Arvanitidou |
| 6,492,313 B1 | 12/2002 | Connors et al. |
| 6,495,500 B1 | 12/2002 | Connors et al. |
| 6,498,137 B1 | 12/2002 | Schalitz et al. |
| 6,551,553 B1 | 4/2003 | von Rheinbaben et al. |
| 6,583,181 B1 | 6/2003 | Chiang et al. |
| 6,610,639 B1 | 8/2003 | Arvanitidou et al. |
| 6,617,296 B1 | 9/2003 | Connors et al. |
| 6,635,609 B2 | 10/2003 | Sutton |
| 6,693,070 B1 | 2/2004 | Cheung et al. |
| 6,762,157 B1 | 7/2004 | Babinski et al. |
| 6,793,914 B2 | 9/2004 | Clarkson et al. |
| 6,875,733 B1 | 4/2005 | Wojtczak et al. |
| 7,026,308 B1 | 4/2006 | Gavin et al. |
| 7,060,302 B1 | 6/2006 | Hickok |
| 7,087,567 B2 | 8/2006 | Connors et al. |
| 7,163,709 B2 | 1/2007 | Cook et al. |
| 7,182,537 B2 | 2/2007 | Policicchio et al. |
| 7,182,941 B2 | 2/2007 | Trinh et al. |
| 7,238,654 B2 | 7/2007 | Hodge et al. |
| 7,455,851 B1 | 11/2008 | Nelson et al. |
| 7,591,840 B2 | 9/2009 | Suddaby |
| 7,625,855 B2 | 12/2009 | Gonzalez |
| 7,629,386 B2 | 12/2009 | Salamone |
| 7,645,746 B1 | 1/2010 | Trinh et al. |
| 7,879,365 B2 | 2/2011 | Modak |
| 7,915,210 B2 | 3/2011 | Bennett et al. |
| 7,951,761 B2 | 5/2011 | Gonzalez |
| 7,951,840 B2 | 5/2011 | Modak |
| 7,956,024 B2 | 6/2011 | Gonzalez |
| 8,877,698 B2 | 11/2014 | Bennett et al. |
| 2001/0044392 A1 | 11/2001 | Trinh et al. |
| 2001/0049347 A1 | 12/2001 | Robbins et al. |
| 2002/0022660 A1 | 2/2002 | Jampani et al. |
| 2002/0045667 A1 | 4/2002 | Baker et al. |
| 2002/0057988 A1 | 5/2002 | Diaz |
| 2002/0119207 A1 | 8/2002 | Baker, Jr. et al. |
| 2002/0155969 A1 | 10/2002 | Rees et al. |
| 2002/0183233 A1 | 12/2002 | Mitra et al. |
| 2003/0013769 A1 | 1/2003 | Mukkamala et al. |
| 2003/0032573 A1 | 2/2003 | Tanner et al. |
| 2003/0100465 A1 | 5/2003 | Kilkenny et al. |
| 2003/0148917 A1 | 8/2003 | Mitra et al. |
| 2003/0153478 A1 | 8/2003 | Sutton |
| 2003/0211066 A1 | 11/2003 | Scholz et al. |
| 2003/0215418 A1 | 11/2003 | Asmus et al. |
| 2003/0216273 A1 | 11/2003 | Mitra et al. |
| 2004/0033916 A1 | 2/2004 | Kuzmin et al. |
| 2004/0058878 A1 | 3/2004 | Walker et al. |
| 2004/0071653 A1 | 4/2004 | Bratescu et al. |
| 2004/0106533 A1 | 6/2004 | Mitra et al. |
| 2004/0110841 A1 | 6/2004 | Kite et al. |
| 2004/0171509 A1 | 9/2004 | Fox et al. |
| 2004/0204331 A1 | 10/2004 | Connors et al. |
| 2004/0209792 A1 | 10/2004 | Mitra et al. |
| 2004/0213750 A1 | 10/2004 | Bennett et al. |
| 2004/0214785 A1 | 10/2004 | Dees et al. |
| 2004/0259951 A1 | 12/2004 | Clarkson et al. |
| 2005/0008576 A1 | 1/2005 | Makansi |
| 2005/0009722 A1 | 1/2005 | Gonzalez |
| 2005/0013836 A1 | 1/2005 | Raad |
| 2005/0015357 A1 | 1/2005 | Shahidi |
| 2005/0019431 A1 | 1/2005 | Modak et al. |
| 2005/0079146 A1 | 4/2005 | Kuzmin et al. |
| 2005/0089496 A1 | 4/2005 | Lichtenberg et al. |
| 2005/0129766 A1 | 6/2005 | Bringley et al. |
| 2005/0164913 A1 | 7/2005 | Polyakov et al. |
| 2005/0239675 A1 | 10/2005 | Makansi |
| 2005/0261148 A1 | 11/2005 | Xia et al. |
| 2006/0047006 A1 | 3/2006 | Salamone et al. |
| 2006/0177519 A1 | 8/2006 | Hartfeldt et al. |
| 2006/0178431 A1 | 8/2006 | Hartfeldt et al. |
| 2006/0189483 A1 | 8/2006 | Hickok |
| 2006/0233886 A1 | 10/2006 | Kielbania, Jr. et al. |
| 2006/0264349 A1 | 11/2006 | Connors et al. |
| 2006/0281663 A1 | 12/2006 | Asmus |
| 2007/0020140 A1 | 1/2007 | Buhr et al. |
| 2007/0134136 A1 | 6/2007 | Polyakov et al. |
| 2007/0190177 A1 | 8/2007 | Kling et al. |
| 2007/0297990 A1 | 12/2007 | Shah et al. |
| 2008/0045491 A1 | 2/2008 | Fitchmun et al. |
| 2008/0118575 A1 | 5/2008 | Ashmore et al. |
| 2008/0138438 A1 | 6/2008 | Taylor et al. |
| 2008/0254141 A1 | 10/2008 | Hwu et al. |
| 2008/0292676 A1 | 11/2008 | Crudden |
| 2008/0292721 A1 | 11/2008 | Crudden |

(56) References Cited

U.S. PATENT DOCUMENTS

| | | |
|---|---|---|
| 2008/0292723 A1 | 11/2008 | Crudden |
| 2008/0299222 A1 | 12/2008 | Crudden |
| 2009/0018213 A1 | 1/2009 | Snyder et al. |
| 2009/0047364 A1 | 2/2009 | Crudden |
| 2009/0053323 A1 | 2/2009 | Tichy et al. |
| 2009/0074881 A1 | 3/2009 | Kielbania, Jr. |
| 2009/0136581 A1 | 5/2009 | Gutierrez et al. |
| 2009/0214606 A1 | 8/2009 | Bujard et al. |
| 2009/0226494 A1 | 9/2009 | Hickok |
| 2009/0246292 A1 | 10/2009 | Seville et al. |
| 2009/0304813 A1 | 12/2009 | Hickok |
| 2010/0015245 A1 | 1/2010 | Harrison et al. |
| 2010/0021562 A1 | 1/2010 | Chowhan et al. |
| 2010/0041580 A1 | 2/2010 | Gonzalez |
| 2010/0041582 A1 | 2/2010 | Gonzalez |
| 2010/0098777 A1 | 4/2010 | Gould et al. |
| 2010/0132741 A1 | 6/2010 | Frey et al. |
| 2010/0151046 A1 | 6/2010 | Okamoto et al. |
| 2010/0187263 A1 | 7/2010 | Lestage et al. |
| 2010/0189611 A1 | 7/2010 | Lestage et al. |
| 2010/0189809 A1 | 7/2010 | Lestage et al. |
| 2010/0209460 A1 | 8/2010 | Pietsch |
| 2010/0233098 A1 | 9/2010 | Bennett et al. |
| 2014/0127141 A1 | 5/2014 | Ijaz et al. |
| 2014/0134269 A1 | 5/2014 | Ijaz et al. |
| 2014/0140935 A1 | 5/2014 | Ijaz et al. |
| 2014/0147513 A1 | 5/2014 | Ijaz et al. |
| 2014/0161905 A1 | 6/2014 | Ijaz et al. |
| 2014/0212361 A1 | 7/2014 | Ijaz et al. |
| 2015/0189888 A1 | 7/2015 | Ijaz et al. |
| 2015/0237867 A1 | 8/2015 | Ijaz et al. |
| 2015/0250183 A1 | 9/2015 | Apollo et al. |
| 2015/0290102 A1* | 10/2015 | Cozean ............... A61K 31/155 514/458 |

FOREIGN PATENT DOCUMENTS

| | | |
|---|---|---|
| EP | 0414309 A1 | 2/1991 |
| EP | 0689767 A2 | 1/1996 |
| EP | 0848907 A1 | 6/1998 |
| EP | 1767495 A1 | 3/2007 |
| EP | 2135507 A1 | 12/2009 |
| JP | 04305505 A | 10/1992 |
| JP | 7179318 A | 7/1995 |
| WO | 0005330 A1 | 2/2000 |
| WO | 0030601 A1 | 6/2000 |
| WO | 02065838 A1 | 8/2002 |
| WO | 03073857 A2 | 9/2003 |
| WO | 03073858 A2 | 9/2003 |
| WO | 03075664 A1 | 9/2003 |
| WO | 2008154395 A1 | 12/2008 |
| WO | 2009130608 A2 | 10/2009 |
| WO | 2012136968 A1 | 10/2012 |
| WO | 2012164251 A1 | 12/2012 |
| WO | 2012164252 A1 | 12/2012 |
| WO | 2012164253 A1 | 12/2012 |
| WO | 2012164254 A1 | 12/2012 |
| WO | 2012164255 A1 | 12/2012 |
| WO | 2013142474 A1 | 9/2013 |
| WO | 2014006380 A1 | 1/2014 |
| WO | 2014006381 A1 | 1/2014 |
| WO | 2014006382 A1 | 1/2014 |
| WO | 2014006383 A1 | 1/2014 |

OTHER PUBLICATIONS

Written Opinion of the International Searching Authority for PCT/GB2013/053129 dated Apr. 11, 2014.
Anonymous, "Disinfectant", Wikipedia, the free encyclopedia, Oct. 9, 2010, XP002680035.
WPI Abstract Accession No. 1992-410101.
WPI Abstract Accession No. 1995-280817.
STN Database Accession No. 2000: 31926 XP-002197632.
C.E.Coulthard, et al., "The Germicidal Effect of Alcohol with Special Reference to its Action on Bacterial Spores", The Pharmaceutical Journal, Jul. 18, 1936, pp. 79-81.
J. Sagripanti, et al., "Virus Inactivation by Copper or Iron Ions Alone and in the Presence of Peroxide", Applied and Environmental Microbiology, vol. 59, No. 12, pp. 4374-4376, Dec. 1993.
"Quaternary ammonium cation", Wikipedia.org, Apr. 14, 2016.

* cited by examiner

US 9,707,162 B2

MICROBICIDAL PERSONAL CARE COMPOSITIONS COMPRISING METAL IONS

The present invention relates to personal care compositions which comprise metal ions selected from copper ions and/or zinc ions, which compositions exhibit a microbicidal benefit when applied to animate surfaces, e.g. dermal and/or topical surfaces including skin and hair. The aqueous alcoholic compositions provide a surprisingly high degree of microbicidal activity against various undesirable microorganisms (sometimes referred to as 'pathogens') including various bacteria, mycobacteria, viruses, and fungi.

While ethanol and other monohydric alcohols are known to the art as having a beneficial microbicidal benefit, at the same time it is a volatile organic compound ("VOC") and there is a substantial interest in regulating the use of ethanol (as well as other volatile organic compounds) in products wherein the ethanol or other VOC is exposed to the environment. Such regulatory interests are, however, completely contrary to the technical benefits provided by ethanol and other monohydric alcohols, and in particular ethanol, as a microbicidal agent, as increased levels of ethanol in a composition have long been known to find increased microbicidal benefits against undesirable microorganisms.

Further, while ethanol and other monohydric alcohols are known to the art as having a beneficial microbicidal benefit they are not without undesirable effects as well; topical compositions with higher amounts of ethanol are known to cause undesirable drying of the skin, and foaming personal care compositions are difficult to formulate where such comprise higher amounts of ethanol.

The technical art has proposed several compositions which are cited to provide some degree of microbicidal/germicidal/antimicrobial efficacy, at the same time to comprise reduced amounts of ethanol and other monohydric alcohols while still providing an appreciable microbicidal benefit. However, these compositions are not wholly successful in providing microbicidal/germicidal/antimicrobial benefit against a broad range of undesirable microorganisms, and in particular in providing effective microbicidal benefit against particularly difficult to eradicate microorganisms including non-enveloped viruses, and in particular polioviruses [e.g., poliovirus type 1 (Sabin)]. As is recognized in the art, demonstrated eradication of poliovirus is highly advantageous as such compositions would not only be effective in controlling this dangerous microorganism but at the same time such a high level of efficacy would also be recognized against relatively easier to eradicate microorganisms including but not limited to bacteria, mycobacteria, other non-enveloped and enveloped virus strains including fungi.

The prior art discloses various compositions which are cited to provide a microbicidal effect.

In U.S. Pat. No. 3,992,146 are disclosed germicidal and antifungal compositions which are based on aqueous solutions of a copper compound and a surfactant. The surfactants disclosed are primarily anionic surfactants based on sulfate or sulfonated organic compounds. The use of ethanol or of specific pH ranges are not clearly disclosed or demonstrated.

U.S. Pat. No. 5,180,749 describes largely aqueous compositions comprising about 65-88% wt. water and which include as further essential constituents both about 10-30% wt. ethanol with about 2-5% wt. benzyl alcohol. However, the use of water soluble metal salts is not disclosed nor is the pH of the compositions disclosed. The compositions were tested against *Staphylococcus aureus, Salmonella cholerae-suis, Pseudomonas aeruginosa*, rhinovirus type 39, herpes simplex 1, herpes simplex 2, adenovirus type 2, respiratory syncytial, influenza A2, influenza B, human rotavirus, *Mycobacterium tuberculosis* var. *bovis*, as well as fungi of types *Aspergillus niger* and *Trichopython mentgrophytes*. In that patent, when contrasting the data from Table B to the data from Table A, the necessary inclusion of benzyl alcohol in conjunction with ethanol in order to achieve increased microbicidal efficacy is shown. The poor microbicidal efficacy of compositions comprising 30% wt. ethanol and water and where benzyl alcohol is absent is demonstrated on Table B.

U.S. Pat. No. 5,728,404 discloses certain virucidal disinfectant compositions which are described as including one or more $C_1$-$C_4$ aliphatic alcohols, 0.1-1% wt. of a hydrolized metal ion, and water. Compositions comprising ethyl alcohol and isopropyl alcohol and ratios of 8:1 to 1:1 are noted to be particularly effective and preferred. While the document alleges that the amount of the aliphatic alcohol may be in the range of 40%-90% wt., such is not demonstrated as in the four examples provided the amount of the aliphatic alcohols are respectively 80% wt., 70% wt., 80% wt. and 80% wt. Furthermore, when formed as described in that document, the composition according to Example 1 of this patent document exhibited a pH of 5.48, the composition of Example 2 exhibited a pH of 5.63, and the composition of Example 3 exhibited a pH of 5.63, which indicates that the foregoing compositions consistently demonstrated an acidic pH.

U.S. Pat. Nos. 6,034,043 and 6,017,861 disclose liquid skin cleaning compositions comprising (1) a so-called mild surfactant system of which at least 10% wt. of which (and which preferably at least 25% wt. of which), is an anionic surfactant, (2) 0.1-10% wt. of a polyvalent cation or cations selected from zinc, copper, tin, aluminum, cobalt, nickel, chromium, titanium, and/or manganese and mixtures thereof, and (3) 1-99% wt. water wherein the cations provide antimicrobial activity. These patents suggest that microbiocidal activity of the liquid skin cleaning compositions was due to the combination of the mild surfactant system with the polyvalent cation or cations whereas the polyvalent cation or cations themselves did not provide a microbiocidal benefit. Further, none of the demonstrated compositions include lower alkyl monohydric alcohols.

U.S. Pat. No. 8,119,115 discloses certain antiviral compositions which are cited to be useful against non-enveloped viruses. The compositions necessarily include an alcohol component which is cited to be present in at least 50% wt. but is preferably present in amounts of at least 60% wt, and more preferably at least 65% wt. and even higher amounts, in conjunction with a so-called enhancer component which may be a cationic oligomer or polymer, such as cationic cationic polysaccharides, cationic copolymers of saccharides and synthetic cationic monomers, and synthetic cationic oligomers or polymers which include cationic polyalkylenimines, cationic ethoxy polyalkylene imines, cationic poly[N-[3-dialkylammonio)alkyl]N' [3-alkyleneoxyalkylene dialkylammonio)alkyl]urea dichloride], vinyl caprolactam/VP/dialkylaminoalkyl alkylate copolymers, and polyquaternium polymers. Notably all of the example compositions tested included 70% wt. or more of ethanol.

U.S. Pat. No. 8,450,378, based on a continuation-in-part patent application of U.S. Pat. No. 8,119,115, and additionally discloses that zinc or copper compounds may be included in addition to the alcohol and cationic oligomer or polymer compounds. As is known to the art, oligomers are essentially short chained polymer compounds which necessarily have a number of repeating units. Similarly to the related application, exemplified compositions of the invention comprise 62% wt., but predominantly comprise 70%-78% wt. of ethanol.

U.S. Pat. No. 8,470,755 discloses certain liquid cleaning and disinfecting compositions which necessarily comprise an inorganic salt which is preferably a divalent zinc salt, and a linear alkyl alkyl nucleophilic surfactant such as a linear alkyl chain amine oxide. The example compositions demonstrate only that the addition of divalent zinc ions (Zn++) provide an increased antimicrobial benefit against E. coli, S. aureus and P. aeroginosa when used in conjunction with a linear $C_{12-14}$ alkyl dimethyl amine oxide compound, versus a cocoamidopropyl dimethyl amine oxide compound, a symmetrically branched dimethyl amine oxide compound or a non-symmetrically amine oxide with a methyl branched moiety, the latter three amine oxide compounds which did not demonstrate any improvement in antibacterial efficacy against the same tested microorganisms.

US 2004/0213750 discloses aqueous alcoholic compositions which comprise 40% wt.-70% wt. of a lower alkanol, optionally a quaternary ammonium cationic compound which itself provides germicidal properties, water and a pH adjusting agent to provide a final pH of between 7 and 13. The compositions are shown to be effective against various microorganisms including gram-positive and gram-negative types of pathogenic bacteria, as well as Poliovirus (Type 1) at a 10 minute contact time. The reference however makes no mention of the use of copper ions in the compositions.

US 2007/0184013 discloses compositions which are cited to be effective against non-enveloped virus particles. The compositions comprise a $C_1$-$C_6$ alcohol and an efficacy-enhancing amount of one or more of: cationic oligomers and polymers, proton donors, chaotropic agents, and mixtures thereof with the proviso that when the compositions include a proton donor that a cationic oligomer or polymer is also present. The cationic oligomers and polymers disclosed are defined to include cationic polyalkylene imines, cationic ethoxy polyalkylene imines, cationic poly[N-[3-(dialkylammonio)alkyl]N'[3-(alkyleneoxyalkylene dialkylammonio) alkyl]urea dichloride], vinyl caprolactam/VP/dialkylaminoalkyl alkylate copolymers and polyquaternium copolymers. The example compositions disclosed in the reference demonstrate compositions having 62% wt. and even greater amounts of the $C_1$-$C_6$ alcohol as being present.

US 2008/0045491 discloses certain surface sanitizer compositions which are recited to include 50-90% wt. of an alcohol component, 10-50% wt. of water, an acid component to maintain the pH of the composition between 2-5, and 0.05-5% wt. of a multivalent cation constituent. The multivalent cation constituent may be a one of a selected list of polymers, a metal ion or a metal compound. The compositions may further optionally include one or more further constituents including oxidative agents, plant derived alkenes or essential oils, emollients, humectants, lubricants and one or more antimicrobial compounds, e.g., quaternary ammonium compounds. The single example of US 2008/0045491 tested demonstrates that a composition having 78% wt. ethanol exhibits efficacy against Candida albicans, Aspergillus niger, Escherichia coli, Pseudomonas aeruginosa, Staphylococcus aureus and adenovirus type 5. Further examples disclosed in US 2008/0045491 are not disclosed to have been tested against any microorganisms.

The treatment of biofilms by compositions which include certain heavy metals are known from US 2008/0118573. The treatment steps require that the biofilms be contacted with the said compositions for 4 hours or more. The biofilms are defined to be conglomerates of microbial organisms embedded in highly hydrated matricies of exopolymers, typically polysaccharides, and other macromolecules.

US 2009/0226494 discloses certain antibacterial formulations which comprise a water-soluble copper compound, a water-soluble ammonium agent, and a water-soluble acid when the composition necessarily has an acidic pH.

US 2010/0233098 discloses methods and compositions for disinfecting hard surfaces which are aqueous compositions which comprise 40% wt.-70% wt. of an alcohol constituent selected from the group consisting of methanol, ethanol, n-propanol, isopropanol, n-butanol, benzyl alcohol, and mixtures thereof and a pH in the range of from about 7.0-14.0. The compositions may include further optional constituents, including ancillary antimicrobial agents, and surfactants, but the use of water soluble metal salts is not disclosed.

US 2013/0237598, which is related to both U.S. Pat. Nos. 8,119,115 and 8,450,378 is of similar scope, but discloses several additional example compositions in addition to those previously disclosed in U.S. Pat. No. 8,450,378, which further example compositions include 74.1% ethanol, a Polyquaternium polymer, and PEG-10 dimethicone and PEG-12 dimethicones, with a demonstrated effect against adenovirus and hepatitis A.

Notwithstanding these various known art compositions, there is still an urgent need in the art to produce treatment compositions, adapted for the control or eradication of undesired microorganisms where such treatment compositions comprise reduced amounts of VOC, and in particular aliphatic alcohols which provide a microbicidal effect such as ethanol, yet which compositions are highly effective against particularly difficult to eradicate undesired microorganisms, especially poliovirus, particularly where the treatment compositions are applied to an animate surface.

In a first broad aspect, the compositions of the present invention are generally directed to animate surface treatment compositions, (e.g., a personal care compositions,) which impart an antimicrobial or microbicidal benefit to such treated surfaces which compositions comprise (or in certain preferred embodiments may consist essentially of, or may consist of):

a metal ion source material selected from a copper ion source material which releases copper ions into the said treatment composition or a zinc ion source material which releases zinc ions into the said treatment composition;

at least one quaternary ammonium compound which independently of other constituents present exhibits a microbicidal effect;

at least one lower alkyl aliphatic monohydric alcohol which independently of other constituents present exhibits a microbicidal effect;

water; and, optionally but very preferably, also at least one further detersive surfactant.

These compositions may optionally additionally include one or more further constituents which impart one or more advantageous technical or aesthetic benefits to the compositions. Preferably the compositions are at a pH such that the said treatment compositions impart a microbicidal or antimicrobial or germicidal effect on treated animate surfaces, particularly a dermal surface such as skin and/or a keratinous surface such as hair. These treatment compositions are characterized in exhibiting a microbicidal benefit when tested against one or more challenge organisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, 17$^{th}$ Ed. (2000), or ASTM E2315-03(2008) Standard Guide for Assessment of Antimicrobial Activity Using a Time-Kill Procedure.

The compositions may be solids, readily pourable fluids or liquids (e.g., lotions, hair treatment preparations, bodywash compositions, rinse compositions, foaming compositions) viscous fluids or liquids (e.g., gels, pastes, creams and the like), as well as pumpable or sprayable compositions (e.g. pumpable, non-aerosol compositions, pressurized compositions, aerosol compositions). Such compositions may also be provided in any apparatus or device wherein the composition may be delivered, (e.g., poured or sprayed) onto an animate surface and/or substrate which is to contacted with an animate surface and/or keratinous surface. The inventive compositions in any of its aspects provide a high degree of microbicidal activity against various undesirable microorganisms (sometimes referred to as 'pathogens') including various bacteria, mycobacteria, viruses, and fungi. The essential cationic quaternary ammonium compounds are preferably non-polymeric and/or non-oligomeric cationic surfactant compounds, e.g, are distinguished from the cationic oligomers and polymers disclosed as being essential to the compositions as disclosed in U.S. Pat. Nos. 8,119,115 and 8,450,378.

In an embodiment of this first aspect, the present invention provides animate surface treatment compositions (e.g., a personal care compositions,) which impart a microbicidal benefit to such treated surfaces which comprise (or in certain preferred embodiments may consist essentially of, or may consist of):

a copper ion source material which releases copper ions into the treatment composition, preferably a source of Cu(I) and/or Cu(II) ions;

at least one lower alkyl aliphatic monohydric alcohol, preferably present in amounts of at least about 10% wt;

at least one cationic quaternary ammonium compound which provides a microbicidal benefit;

water;

optionally, one or more further constituents which impart one or more advantageous technical or aesthetic benefits to the compositions, including one or more detersive surfactants;

wherein the composition has a pH of at least about 3, wherein the treatment compositions are characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN1369, or AOAC Germicidal Spray Products as Disinfectant Test Method, AOAC Index, 17$^{th}$ Ed. (2000), or ASTM E2315-03(2008) Standard Guide for Assessment of Antimicrobial Activity Using a Time-Kill Procedure against one or more challenge microorganisms, especially preferably against gram positive bacteria, gram negative bacteria, preferably adenovirus and/or poliovirus type 1 (Sabin) ("PV1").

In an alternative embodiment of the first aspect of the inspection, the present invention provides animate surface treatment compositions (e.g., a personal care compositions,) which impart a microbicidal benefit to such treated surfaces which comprise (or in certain preferred embodiments may consist essentially of, or may consist of):

a zinc ion source material which releases zinc ions into the treatment composition, preferably a source of Zn(I) and/or Zn(II) ions;

at least one lower alkyl aliphatic monohydric alcohol, preferably present in amounts of at least about 10% wt;

at least one cationic quaternary ammonium compound which provides a microbicidal benefit;

water;

optionally, one or more further constituents which impart one or more advantageous technical or aesthetic benefits to the compositions, including one or more detersive surfactants;

wherein the composition has a pH of at least about 7, wherein the treatment compositions are characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN1369, or AOAC Germicidal Spray Products as Disinfectant Test Method, AOAC Index, 17$^{th}$ Ed. (2000), or ASTM E2315-03(2008) Standard Guide for Assessment of Antimicrobial Activity Using a Time-Kill Procedure against one or more challenge microorganisms, especially preferably against gram positive bacteria, gram negative bacteria, preferably adenovirus and/or poliovirus type 1 (Sabin) ("PV1").

According to a second broad aspect, the compositions of the present invention are generally directed to animate surface treatment compositions (e.g., a personal care compositions,) which impart an antimicrobial or microbicidal benefit to treated surfaces which compositions comprise (or in certain preferred embodiments may consist essentially of, or may consist of):

a metal ion source material selected from a copper ion source material which releases copper ions into the said treatment composition or a zinc ion source material which releases zinc ions into the said treatment composition;

at least one quaternary ammonium compound which independently of other constituents present exhibits a microbicidal effect;

water; and, optionally but very preferably, also at least one further detersive surfactant.

These compositions may optionally additionally include one or more further constituents which impart one or more advantageous technical or aesthetic benefits to the compositions. These compositions are at a pH such that the said treatment compositions exhibit a microbicidal or antimicrobial or germicidal effect on treated animate surfaces, particularly a dermal surface such as skin and/or a keratinous surface such as hair. These treatment compositions are characterized in exhibiting a microbicidal benefit when tested against one or more challenge organisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, 17$^{th}$ Ed. (2000), or ASTM E2315-03(2008) Standard Guide for Assessment of Antimicrobial Activity Using a Time-Kill Procedure. The compositions may be solids, readily pourable fluids or liquids (e.g., lotions, hair treatment preparations, bodywash compositions, rinse compositions, foaming compositions) viscous fluids or liquids (e.g., gels, pastes, creams and the like), as well as pumpable or sprayable compositions (e.g. pumpable, non-aerosol compositions, pressurized compositions, aerosol compositions). Such compositions may also be provided in any apparatus or device wherein the composition may be delivered, (e.g., poured or sprayed) onto an animate surface and/or substrate which is to contacted with an animate surface and/or keratinous surface. The inventive compositions in any of its aspects provide a high degree of microbicidal activity against various undesirable microorganisms (sometimes referred to as 'pathogens') including various bacteria, mycobacteria, viruses, and fungi. The essential cationic quaternary ammonium compounds are preferably non-polymeric and/or non-oligomeric cationic surfactant compounds, e.g, are distinguished from the cationic oligomers and polymers disclosed as being essential to the compositions as disclosed in U.S. Pat. Nos. 8,119,115 and 8,450,378.

According to a third broad aspect, the compositions of the present invention are generally directed to animate surface treatment compositions (e.g., a personal care compositions,) which impart an antimicrobial or microbicidal benefit to treated animate surfaces which compositions comprise (or in certain preferred embodiments may consist essentially of, or may consist of):

a metal ion source material selected from a copper ion source material which releases copper ions into the said treatment composition or a zinc ion source material which releases zinc ions into the said treatment composition;

at least one lower alkyl aliphatic monohydric alcohol which independently of other constituents present exhibits a microbicidal effect;

water; and, optionally but very preferably, also at least one further detersive surfactant.

These compositions may optionally additionally include one or more further constituents which impart one or more advantageous technical or aesthetic benefits to the compositions. These compositions are at a pH such that the said treatment compositions exhibit a microbicidal or antimicrobial or germicidal effect on treated animate surfaces, particularly a dermal surface such as skin and/or a keratinous surface such as hair. These treatment compositions are characterized in exhibiting a microbicidal benefit when tested against one or more challenge organisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697, or AOAC Germicidal Spray Products as Disinfectant Test Method, AOAC Index, $17^{th}$ Ed. (2000), or ASTM E2315-03(2008) Standard Guide for Assessment of Antimicrobial Activity Using a Time-Kill Procedure. The compositions may be solids, readily pourable fluids or liquids (e.g., lotions, hair treatment preparations, bodywash compositions, rinse compositions, foaming compositions) viscous fluids or liquids (e.g., gels, pastes, creams and the like), as well as pumpable or sprayable compositions (e.g. pumpable, non-aerosol compositions, pressurized compositions, aerosol compositions). Such compositions may also be provided in any apparatus or device wherein the composition may be delivered, (e.g., poured or sprayed) onto an animate surface and/or substrate which is to contacted with an animate surface and/or keratinous surface. The inventive compositions in any of its aspects provide a high degree of microbicidal activity against various undesirable microorganisms (sometimes referred to as 'pathogens') including various bacteria, mycobacteria, viruses, and fungi. The essential cationic quaternary ammonium compounds are preferably non-polymeric and/or non-oligomeric cationic surfactant compounds, e.g, are distinguished from the cationic oligomers and polymers disclosed as being essential to the compositions as disclosed in U.S. Pat. Nos. 8,119,115 and 8,450,378.

The present inventors have also found that the treatment compositions (and/or the microbial control systems described hereinafter) exhibit an improved or synergistic antimicrobial efficacy where such comprise a copper ion source material which releases copper ions into the treatment composition and/or a zinc ion source material which releases zinc ions into the treatment composition, as compared to like compositions where the copper ion source material or the zinc ion source material is omitted.

In a fourth aspect of the invention there is provided a first microbicidal control system of constituents which are in and of themselves are effective in providing effective control of gram positive bacteria, gram negative bacteria, and preferably adenovirus and/or poliovirus type 1 (Sabin) ("PV1"), independently of further and optional constituents. This first microbicidal control system of constituents comprises (or consists essentially of, or consists of): water, a metal ion source material selected from a copper ion source material which releases copper ions into the said system and/or a zinc ion source material which releases zinc ions into the said system; at least one lower alkyl aliphatic monohydric alcohol which independently of other constituents in the system exhibits a microbicidal effect and which is preferably present in an amount of at least about 10% wt. of a microbicidal control system of which it forms a part; at least one cationic quaternary ammonium compound which provides a microbicidal benefit independently of the other constituents of the microbicidal control system; and, where necessary a buffer and/or pH adjusting agent to impart an appropriate pH for the microbicidal control system. This first microbicidal control system of constituents may thereafter optionally include further constituents which may or may not provide a further microbicidal benefit. Preferably the microbicidal control system is characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN1369, or AOAC Germicidal Spray Products as Disinfectant Test Method, AOAC Index, $17^{th}$ Ed. (2000), or ASTM E2315-03(2008) Standard Guide for Assessment of Antimicrobial Activity Using a Time-Kill Procedure, especially preferably against gram positive bacteria, gram negative bacteria, preferably adenovirus and/or poliovirus type 1 (Sabin) ("PV1"). This first microbicidal control system of constituents is, or may form a part of, an animate surface treatment composition which imparts a microbicidal benefit.

In a fifth aspect of the invention there is provided a second microbicidal control system of constituents which are in and of themselves are effective in providing effective control of gram positive bacteria, gram negative bacteria, and preferably adenovirus and/or poliovirus type 1 (Sabin) ("PV1"), independently of further and optional constituents, which second microbicidal control system of constituents comprises (or consists essentially of, or consists of): water, a metal ion source material selected from a copper ion source material which releases copper ions into the said system and/or a zinc ion source material which releases zinc ions into the said system; at least one cationic quaternary ammonium compound which provides a microbicidal benefit independently of the other constituents of the microbicidal control system; and, where necessary a buffer and/or pH adjusting agent to impart an appropriate pH for the microbicidal control system. This second microbicidal control system of constituents may thereafter optionally include further constituents which may or may not provide a further microbicidal benefit. Preferably the microbicidal control system is characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN1369, or AOAC Germicidal Spray Products as Disinfectant Test Method, AOAC Index, 17$^{th}$ Ed. (2000), or ASTM E2315-03(2008) Standard Guide for Assessment of Antimicrobial Activity Using a Time-Kill Procedure, especially preferably against gram positive bacteria, gram negative bacteria, preferably adenovirus and/or poliovirus type 1 (Sabin) ("PV1"). This second microbicidal control system of constituents is, or may form a part of, an animate surface treatment composition which imparts a microbicidal benefit.

In a sixth aspect of the invention there is provided a third microbicidal control system of constituents which are in and of themselves are effective in providing effective control of gram positive bacteria, gram negative bacteria, and preferably adenovirus and/or poliovirus type 1 (Sabin) ("PV1"), independently of further and optional constituents. This third microbicidal control system of constituents comprises (or consists essentially of, or consists of): water, a metal ion source material selected from a copper ion source material which releases copper ions into the said system and/or a zinc ion source material which releases zinc ions into the said system; at least one lower alkyl aliphatic monohydric alcohol which independently of other constituents in the system exhibits a microbicidal effect which is preferably present in an amount of at least about 10% wt. of a treatment composition of which it forms a part; and, where necessary a buffer and/or pH adjusting agent to impart an appropriate pH for the microbicidal control system. This third microbicidal control system of constituents may thereafter optionally include further constituents which may or may not provide a further microbicidal benefit. Preferably the microbicidal control system is characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN1369, or AOAC Germicidal Spray Products as Disinfectant Test Method, AOAC Index, 17$^{th}$ Ed. (2000), or ASTM E2315-03(2008) Standard Guide for Assessment of Antimicrobial Activity Using a Time-Kill Procedure, especially preferably against gram positive bacteria, gram negative bacteria, preferably adenovirus and/or poliovirus type 1 (Sabin) ("PV1"). This third microbicidal control system of constituents is, or may form a part of, an animate surface treatment composition which imparts a microbicidal benefit.

Any of the foregoing microbicidal control systems of constituents may be included in an animate surface treatment composition, (e.g., a personal care compositions, which includes at least one further constituent, e.g., further surfactant, soaps, volatile oils, non-volatile oils, humectants, organic solvents, pH adjusting agents, dyes, colorants, fragrances, preservatives, propellants, skin conditioning agents, oils from botanical sources, e.g., essential oils, as well as other conventional constituents which are conventionally present or known to the relevant technical art of topical compositions, hair treatment compositions, skin treatment compositions, cosmetics, and personal care compositions.

Preferably, according to any of the foregoing aspects, the animate surface treatment compositions (and/or microbial control systems) additionally include at least one further detersive surfactant, which is preferably a nonionic surfactant which provides an increased or enhanced microbicidal benefit when included with the essential constituents of the first, second, third, fourth, fifth or sixth aspects of the invention benefit, as compared to like compositions where such at least one further detersive surfactant (viz., preferably a nonionic surfactant) is absent. Thus, in such further embodiments, the inclusion of one or more further detersive surfactants which provide such an increase in microbicidal benefit are further essential constituents of certain aspects of the inventive compositions.

In a still further aspect the present invention provides a method of controlling the incidence of undesired microorganisms on an animate surface, the method comprising the step of: contacting an animate surface which is in need of treatment or upon which the presence of one or more undesirable microorganisms are suspected or are known to be present, with an effective amount of an animate surface treatment composition according to the first, second or third aspects of the invention, and/or a microbicidal control systems of constituents according to the fourth, fifth, or sixth aspects of the invention, as described above, or as otherwise described in this patent specification to provide an animate surface treatment benefit thereto, preferably to provide a microbicidal benefit to the contacted animate surface.

In an additional aspect the present invention provides a method for the manufacture of a vendible product which comprises an animate surface treatment composition and/or a microbicidal control systems of constituents as described herein.

These and further aspects of the invention will become more apparent from a reading of the following specification.

In all aspects, an essential constituent of the invention is a metal ion source material selected from a copper ion source material which releases copper ions into the said treatment composition and/or a zinc ion source material which releases zinc ions into the said treatment composition When present, the copper ion source material may be any material which releases copper ions into the animate treatment composition, which copper ion source material is preferably a source of Cu(I) and/or Cu(II) ions. The copper ions should be dispersible, miscible or soluble in the animate surface treatment compositions. Preferably the copper ion source material is at least partially soluble or miscible in water or in an aqueous/alcoholic mixture. Non-limiting examples of such materials or compounds include: copper sulfate, copper chloride, copper nitrate, copper oxychloride, copper D-gluconate, copper citrate, copper oxylate, copper usnate, copper acetate, copper chloride, copper carbonate, alanine/histidine/lysine polypeptide copper HCl, bis(tripeptide-1) copper acetate, chlorophyllin-copper complex, copper acetylmethionate, copper acetyl tyrosinate methylsilano, copper adenosine triphosphate, copper aspartate, copper chlorophyll, copper DNA, copper gluconate, copper PCA, copper PCA methylsilanol, copper picolinate, copper powder, copper tripeptide-1, disodium EDTA-copper, and silver copper zeolite. Elemental copper, or copper metal may be also be used, although such is of poor solubility. Such are to be expressly understood as non-limiting examples and that other compounds, compositions and materials which may function to provide copper ions may be used, e.g., further copper containing salts of organic or inorganic compounds or materials. The copper ions need not be fully soluble within the animate surface treatment compositions disclosed herein and may, for example, be dispersions, suspensions, or emulsions, e.g., water-in-oil emulsions, or oil-in-water emulsions. Emulsions having more than two phases, e.g., oil-in-water-in-oil as well s water-in-oil-in-water emulsions may also be forms of the animate surface treatment compositions disclosed herein.

The copper ion source material may be present in the compositions in any effective amount but advantageously comprises about 0.001% wt. to about 2.0% wt, preferably from about 0.01% wt to about 1% wt., and particularly preferably from about 0.01% wt. to about 0.5% wt. of the animate surface treatment compositions. Alternately, the copper ion source material may be present in the animate treatment compositions in any effective amount and may provide as little as about 1 ppm (part per million) of Cu(I) and/or Cu(II) ions to the composition, but preferably the copper ion source material may be present in the treatment compositions in a sufficient amount such that the copper ion source material releases between about 1 ppm to about 10,000 ppm of copper ions, preferably from about 1 ppm to about (in order of increasing preference) 9500, 9000, 8500, 8000, 7500, 7000, 6750, 6500, 6250, 6000, 5750, 5500, 5250, 5000, 4750, 4500, 4250, 4000, 3750, 3500, 3250, 3000, 2750, 2500, 2400, 2300, 2250, 2200, 2100, 2000, 1900, 1800, 1750, 1700, 1650, 1600, 1550, 1500, 1450, 1400, 1350, 1300, 1250, 1200, 1150, 1100, 1050, 1000, 975, 950, 925, 900, 875, 850, 825, 800, 775, 750, 725, 700, 675, 650, 625, 600, 575, 550, 500, 475, 450, 425, 400, 375, 350, 325, 300, 275, 250, 225, 200, 175, 150, 125, 100, 95, 90, 85, 80, 75, 70, 65, 60, 55, 50, 45, 40, 35, 30, 25, 20, 15, 10, 9, 8, 7, 6, 5, 4, 3, 2, ppm, and/or alternately any integer number value or range of integer number values within the above range of 1-10,000 ppm of zinc ions.

Alternately, the copper ion source material may be present in the animate surface treatment compositions in any effective amount which provides an increased microbicidal effect as compared to a like animate treatment composition (or like microbicidal control system0 wherein the copper ion source material is omitted and its mass is replaced by water. Preferably the amount of the copper ion source material is present in a synergistically effective amount.

Exclusive of counterions of surfactant compounds or counterions of other materials described herein which might also be present and provide zinc ions, most preferably the copper ion source material is the sole material present in the composition which releases Cu(I) and/or Cu(II) ions to the animate treatment compositions taught herein.

Exclusive of counterions of surfactant compounds or counterions of other materials described herein which might also be present and provide copper ions, most preferably the copper ion source material is the sole material present in the composition which releases Cu(I) and/or Cu(II) ions to the animate treatment compositions taught herein.

When present, the zinc ion source material may be any material which releases zinc ions into the animate treatment composition, which zinc ion source material is preferably a source of Zn(I) and/or Zn(II) ions. These zinc ions should be dispersible, miscible or soluble in the animate surface treatment compositions. Preferably the zinc ion source material is at least partially soluble or miscible in water or in an aqueous/alcoholic mixture. Non-limiting examples of such materials or compounds include zinc compounds having a counterion selected from acetate, acetylacetonate, bromide, bromide, citrate, chloride, formate, gluconate, glycerophosphate, iodide, lactate, nitrate, salycilate, sulfate, pyrithione and tartrate. By way of non-limiting example, such include species such as zinc acetate, zinc ascorbate, zinc aspartate, zinc butyrate, zinc benzoate, zinc borate, zinc borosilicate, zinc bromate, zinc bromide, zinc carbonate, zinc carbonate hydroxide, zinc chloride, zinc chlorate, zinc citrate, zinc ethylsulfate, zinc fluoride, zinc fluorosilicate, zinc formate, zinc hydrosulfite, zinc hydroxide, zinc glutamate, zinc gluconate, zinc glycinate, zinc glycolate, zinc glycerate, zinc glycolate, zinc glucoheptonate, zinc glycyrrhetinate, zinc hexametaphosphate, zinc iodide, zinc lactate, zinc laurate, zinc linoleate, zinc malate, zinc monohydrate, zinc nitrate, zinc oxide, zinc palmitate, zinc perborate, zinc peroxide, zinc phosphate, zinc picolinate, zinc proprionate, zinc salycilate, zinc silicate, zinc stearate, zinc sulfamate, zinc sulfide, zinc sulfite, zinc sulfate, zinc tartrate, zinc thiosalicylate, and zinc undecylenate. Further non-limiting examples include aluminum zinc oxide, ammonium silver zinc aluminum silicate, ethylene/zinc acrylate copolymer, magnesium/aluminum/zinc/hydroxide/carbonate, silicon/titanium/cerium/zinc oxides, sodium zinc cetyl phosphate, sodium zinc histidine dithiooctanamide, zinc acetylmethionate, zinc adenosine triphosphate, zinc cerium oxide, zinc coceth sulfate, zinc coco-sulfate, zinc cysteinate, zinc dibutyldithiocarbamate, zinc DNA, zinc formaldehyde sulfoxylate, zinc hydrolyzed collagen, zinc magnesium aspartate, zinc myristate, zinc neodecanoate, zinc oxide, zinc PCA, zinc pentadecene tricarboxylate, zinc phenolsulfonate, zinc pyrithione, zinc ricinoleate, zinc rosinate, and zinc zeolite. The zinc ion source material may be in a hydrated form. The zinc ion source material may comprise one or more said compounds, constituents or materials. Preferred zinc ion source materials include zinc salts of an organo-carboxylic acid having from about 2 to about 6 carbon atoms, such as zinc salts of acetates, glycloates, lactates, gluconate, hydrates such as monohydrates, and citrates. Elemental zinc, or zinc metal may be also be used, although such is of poor solubility. The foregoing are to be expressly understood as non-limiting examples and that other compounds, compositions and materials which may function to provide zinc ions may be used, e.g., further zinc containing salts of organic or inorganic compounds or materials. The zinc ions need not be fully soluble within the animate surface treatment compositions disclosed herein and may, for example, be dispersions, suspensions, or emulsions, e.g., water-in-oil emulsions, or oil-in-water emulsions. Emulsions having more than two phases, e.g., oil-in-water-in-oil as well as water-in-oil-in-water emulsions may also be forms of the animate surface treatment compositions disclosed herein.

The zinc ion source material may be present in the compositions in any effective amount but advantageously comprises about 0.001% wt. to about 2.0% wt, preferably from about 0.01% wt to about 1% wt., and particularly preferably from about 0.01% wt. to about 0.5% wt. of the animate surface treatment compositions. Alternately, the zinc ion source material may be present in the animate treatment compositions in any effective amount and may provide as little as about 1 ppm (part per million) of Zn(I) and/or Zn(II) ions to the composition, but preferably the zinc ion source material may be present in the treatment compositions in a sufficient amount such that the zinc ion source material releases between about 1 ppm to about 10,000 ppm of zinc ions, preferably from about 1 ppm to about (in order of increasing preference) 9500, 9000, 8500, 8000, 7500, 7000, 6750, 6500, 6250, 6000, 5750, 5500, 5250, 5000, 4750, 4500, 4250, 4000, 3750, 3500, 3250, 3000, 2750, 2500, 2400, 2300, 2250, 2200, 2100, 2000, 1900, 1800, 1750, 1700, 1650, 1600, 1550, 1500, 1450, 1400, 1350, 1300, 1250, 1200, 1150, 1100, 1050, 1000, 975, 950, 925, 900, 875, 850, 825, 800, 775, 750, 725, 700, 675, 650, 625, 600, 575, 550, 500, 475, 450, 425, 400, 375, 350, 325, 300, 275, 250, 225, 200, 175, 150, 125, 100, 95, 90, 85, 80, 75, 70, 65, 60, 55, 50, 45, 40, 35, 30, 25, 20, 15, 10, 9, 8, 7, 6, 5, 4, 3, 2, ppm, and/or alternately any integer number value or range of integer number values within the above range of 1-10,000 ppm of zinc ions.

Alternately, the zinc ion source material may be present in the animate surface treatment compositions in any effective amount which provides an increased microbicidal effect as compared to a like animate treatment composition (or like microbicidal control system) wherein the zinc ion source material is omitted and its mass is replaced by water. Preferably the amount of the zinc ion source material is present in a synergistically effective amount.

Exclusive of counterions of surfactant compounds or counterions of other materials described herein which might also be present and provide zinc ions, most preferably the zinc ion source material is the sole material present in the composition which releases Zn(I) and/or Zn(II) ions to the animate treatment compositions taught herein.

In certain further embodiments of the invention, a further essential constituent is at least one lower alkyl aliphatic monohydric alcohol. Preferably this at least one of a lower alkyl aliphatic monohydric alcohol also exhibits a biocidal or microbicidal effect against microorganisms independently of the other constituents which may be present in the compositions. Exemplary and preferred are $C_1$-$C_6$ monohydric alcohols, especially methanol, ethanol, n-propanol, isopropanol, and all isomers of butanol. Of these, $C_1$-$C_3$ monohydric alcohols and especially $C_1$-$C_3$ monohydric alcohols are preferred, especially ethanol. A single such alcohol, or mixture of two or more such alcohols, may be present. In certain embodiments when a plurality of alcohols are present, ethanol is the predominant alcohol present, and especially preferably comprises at least 50.1% wt., and especially preferably and in order of increasing preference, at least 51%, 55%, 60%, 65%, 70%, 75%, 80%, 85%, 90%, 92%, 95%, 97%, 98%, 99%, 99.5% and 100% by weight of the at least one lower alkyl aliphatic monohydric alcohol constituent present in the animate treatment compositions.

When present, the at least one lower alkyl aliphatic monohydric alcohol advantageously comprises at least about 10% wt. of the animate surface treatment composition of which it forms a part. Preferably the at least one lower alkyl aliphatic monohydric alcohol constituent is present in the inventive treatment compositions in an amount of at least about 10% wt., and in order of increasing preference comprises at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70% by weight; concurrently and preferably the at least one lower alkyl aliphatic monohydric alcohol constituent is present in the inventive treatment compositions in an amount of up to about 99% wt., and in order of increasing preference is present in an amount up to about 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49.5, 49, 48.5, 48, 47.5, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, and 10% by weight of the treatment composition of which it forms a part.

In certain preferred embodiments wherein at least one lower alkyl aliphatic monohydric alcohol constituent is present, the at least one lower alkyl aliphatic monohydric alcohol forms between about 10% wt. and about 60% wt., preferably forms from about 10% wt. to about 48% wt., preferably to about 46% wt. based on the total amount of the animate surface treatment composition of which it forms a part. Particularly preferred amounts of the at least one lower alkyl aliphatic monohydric alcohol constituent are disclosed with reference to the example compositions.

Advantageously the at least one lower alkyl aliphatic monohydric alcohol constituent exhibits a microbicidal effect against one or more pathogens even in the absence of the further constituents of the treatment compositions taught herein. For this reason, $C_1$-$C_4$ monohydric aliphatic alcohols, e.g., methanol, ethanol and the various isomers of propanol are particularly preferred whether used singly or in mixtures of two or more selected $C_1$-$C_4$ monohydric aliphatic alcohols. In certain embodiments a single $C_1$-$C_4$ monohydric aliphatic alcohol is present as the second essential constituent. In certain embodiments, ethanol is the sole constituent of the lower alkyl aliphatic monohydric alcohol constituent.

In certain embodiments of the invention, a further essential constituent is at least one cationic quaternary ammonium compound which, independently of the at least one lower alkyl aliphatic monohydric alcohol constituent provides a microbicidal benefit. Particularly preferred quaternary ammonium compounds are those which are known to primarily provide a microbicidal benefit rather than a primary detersive benefit, or a fabric softening benefit, or a skin-treatment benefit such as Polyquaternium-type oligomer or (co)polymer compounds. The at least one cationic quaternary ammonium compound is also to be understood to be outside of the scope of the defined detersive surfactants described later in this specification. Otherwise, any microbicidally active cationic surfactant which satisfies these requirements may be used. Mixtures of two or more such microbicidally active cationic surface active agents, viz., cationic surfactants, may also be used. Such microbicidally active cationic surfactants are well known and useful cationic surfactants may be one or more of those described for example in *McCutcheon's Functional Materials*, Vol. 2, 1998; Kirk-Othmer, *Encyclopedia of Chemical Technology*, 4th Ed., Vol. 23, pp. 481-541 (1997), the contents of which are herein incorporated by reference. These are also described in the respective product specifications and literature available from the suppliers of these cationic surfactants.

Non-limiting examples of preferred cationic surfactant compositions which have an independent microbicidal effect are quaternary ammonium compounds and salts thereof, which may be characterized by the general structural formula:

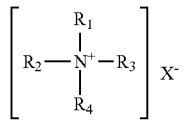

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits for the solubility or miscibility of the quaternary ammonium complex within the treatment composition.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which exhibit an microbicidal effect, viz., act as germicides, and which are useful in the practice of the present invention include those which have the structural formula:

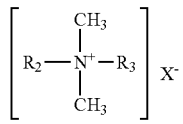

wherein $R_2$ and $R_3$ are the same or different $C_8$-$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, a saccharinate counterion or is a methosulfate anion. The alkyl groups recited in $R_2$ and $R_3$ may be straight-chained or branched, but are preferably substantially linear.

Particularly useful quaternary ammonium compounds useful in the present inventive compositions include materials which include a single quaternary compound, as well as mixtures of two or more different quaternary compounds. Such useful quaternary compounds are available under the BARDAC®, BARQUAT®, HYAMINE®, LONZABAC®, and ONYXIDE® trademarks, which are more fully described in, for example, *McCutcheon's Functional Materials* (Vol. 2), North American Edition, 1998, as well as the respective product literature from the suppliers identified below. Such include, for example: BZT, which is described to be benzethonium chloride (N-benzyl-N,N-dimethyl-2-{2-[4-(2,4,4-trimethylpentan-2-yl)phenoxy] ethoxy}ethanaminium chloride); BARDAC® 205M which is described to be a liquid containing alkyl dimethyl benzyl ammonium chloride; octyl decyl dimethyl ammonium chloride; didecyl dimethyl ammonium chloride, and dioctyl dimethyl ammonium chloride (50% active) (also available as 80% active (BARDAC® 208M)); BARDAC® 2050 which is described to be a combination of octyl decyl dimethyl ammonium chloride/didecyl dimethyl ammonium chloride, and dioctyl dimethyl ammonium chloride (50% active) (also available as 80% active (BARDAC® 2080)); BARDAC® 2250 which is described to be didecyl dimethyl ammonium chloride (50% active); BARDAC® LF (or BARDAC® LF-80), described as being based on dioctyl dimethyl ammonium chloride (BARQUAT® MB-50, MX-50, OJ-50 (each 50% liquid) and MB-80 or MX-80 (each 80% liquid) are each described as an alkyl dimethyl benzyl ammonium chloride; BARDAC® 4250 and BARQUAT® 4250Z (each 50% active) or BARQUAT® 4280 and BARQUAT 4280Z (each 80% active) are each described as alkyl dimethyl benzyl ammonium chloride/alkyl dimethyl ethyl benzyl ammonium chloride. Also, HYAMINE® 1622, described as diisobutyl phenoxy ethoxy ethyl dimethyl benzyl ammonium chloride (50% solution); HYAMINE® 3500 (50% actives), described as alkyl dimethyl benzyl ammonium chloride (also available as 80% active (HYAMINE® 3500-80)); and HYMAINE® 2389 described as being based on methyldodecylbenzyl ammonium chloride and/or methyldodecylxylene-bis-trimethyl ammonium chloride. (BARDAC®, BARQUAT® and HYAMINE® are presently commercially available from Lonza, Inc., Fairlawn, N.J.). BTC® 50 NF (or BTC® 65 NF) is described to be alkyl dimethyl benzyl ammonium chloride (50% active); BTU® 99 is described as didecyl dimethyl ammonium chloride (50% acive); BTU® 776 is described to be myrisalkonium chloride (50% active); BTU® 818 is described as being octyl decyl dimethyl ammonium chloride, didecyl dimethyl ammonium chloride, and dioctyl dimethyl ammonium chloride (50% active) (available also as 80% active (BTU® 818-80%)); BTC® 824 and BTU® 835 are each described as being of alkyl dimethyl benzyl ammonium chloride (each 50% active); BTU® 885 is described as a combination of BTU® 835 and BTU® 818 (50% active) (available also as 80% active (BTU® 888)); BTU® 1010 is described as didecyl dimethyl ammonium chloride (50% active) (also available as 80% active (BTC® 1010-80)); BTC® 2125 (or BTC® 2125 M) is described as alkyl dimethyl benzyl ammonium chloride and alkyl dimethyl ethylbenzyl ammonium chloride (each 50% active) (also available as 80% active (BTC® 2125 80 or BTC® 2125 M)); BTC® 2565 is described as alkyl dimethyl benzyl ammonium chlorides (50% active) (also available as 80% active (BTU® 2568));

BTC® 8248 (or BTC® 8358) is described as alkyl dimethyl benzyl ammonium chloride (80% active) (also available as 90% active (BTC® 8249)); ONYXIDE® 3300 is described as n-alkyl dimethyl benzyl ammonium saccharinate (95% active). (BTC® and ONYXIDE® are presently commercially available from Stepan Company, Northfield, Ill.)

The cationic quaternary ammonium compounds useful in the present inventive compositions are preferably non-polymeric and/or non-oligomeric cationic surfactant compounds, e.g, are distinguished from the cationic oligomers and polymers disclosed as being essential to the compositions as disclosed in U.S. Pat. Nos. 8,119,115 and 8,450,378. It is further to be understood that the animate surface treatment compositions of the first, second and third aspects of the invention, as well as the microbicidal control systems of the fourth, fifth and sixth aspects of the invention, provide unexpectedly effective microbicidal benefits even in the absence of the cationic oligomers and polymers disclosed as being essential to the compositions as disclosed in U.S. Pat. Nos. 8,119,115 and 8,450,378.

When present, the least one cationic quaternary ammonium compound (s) may be present in any effective amount, but generally need not be present in amounts in excess of about 10% wt. based on the total weight of the animate surface treatment composition of which it forms a part. Preferably, when present, the germicidal quaternary ammonium compound(s) may be present in the inventive compositions in amounts of from about 0.001% wt. to up to about 10% wt., very preferably about 0.01-8% wt., more preferably in amounts of between about 0.01-2% wt., and most preferably from about 0.01-1% wt. It is particularly advantageous that the preferred germicidal cationic quaternary ammonium compound(s) are present in amounts of at least about 200 parts per million (ppm), preferably in amounts of from about 1 ppm to 10,000 ppm, preferably from about 50 ppm to 2000 ppm, more preferably in amounts of from about 100 ppm to 1,000 ppm. Particularly preferred amounts of one or more quaternary ammonium compound(s) and preferred amounts are identified with reference to the examples.

While not wishing to be bound by the following, the present inventors have surprisingly found that by careful selection of both: (1) the nature and amounts of the metal ion source material which releases either copper and/or zinc ions into a treatment composition (and/or microbicidal control system of constituents), and especially preferably wherein the metal ion source material is a source of Cu(I) and/or Cu(II) ions, or alternately Zn(I) and/or Zn(II) ions, and either one or both of (2) the at least one lower alkyl aliphatic monohydric alcohol which preferably also exhibits an independent microbicidal effect, and the (3) cationic quaternary ammonium compound which provides a microbicidal benefit, and further wherein the composition is at a pH in a generally acidic range (viz., a pH of about 3 to about 7) when Cu(I) and/or Cu(II) ions are present, or in the alternative, wherein the composition is at a pH in a generally alkaline range (viz., a pH of about 7 to about 10) when Zn(I) and/or Zn(II) ions are present, therein is provided what appears to be a synergistic increase in the microbicidal activity of the compositions and in some instances, especially preferably when these constituents are concurrently present with one or more further detersive surfactant compounds, especially where one or more nonionic surfactant compounds are present. The resultant compositions provide unexpectedly superior microbicidal efficacy against undesirable microorganisms which has heretofore not been expected from compositions which have the markedly reduced amounts of the alcohol constituent as provided in the inventive compositions. Such an effect has been observed even when a very limited amount of the metal ion source material is present, and wherein the amount of the one lower alkyl aliphatic monohydric alcohol is also present in reduced amounts, e.g, in an amount of less than about 50% wt. or even in lesser amounts. Reference is made to the various Examples provided in this specification which demonstrates this effect, particularly as against comparative formulations which omit one or more of: the metal ion source material, the at least one lower alkyl aliphatic monohydric alcohol, the at least one quaternary ammonium compound or wherein the composition exhibits a pH level outside a preferred range. The animate surface treatment compositions as now disclosed by the inventors are believed to be unknown, particularly wherein such treatment compositions exhibit what is believed to be a synergistic benefit.

In certain preferred embodiments the animate surface treatment compositions necessarily include at least one further, detersive surfactant although such may be considered an optional constituent according to other embodiments of the invention. Such at least one further detersive surfactant, (which is preferably is, or includes a nonionic surfactant) is one (or more) surfactant(s) other than a microbicidally effective quaternary ammonium compound. This at least one further detersive surfactant may provide an ancillary microbicidal benefit within the treatment composition of which it forms a part. Such an effect has been observed by the inventors, and thus in certain preferred embodiments such a further detersive surfactant which increases or boosts the microbicidal benefit of animate surface treatment compositions (or systems) according to any of the forgoing aspects of the invention, as compared to like compositions which exclude said surfactant, are also considered to be further essential constituents of the invention. When such further detersive surfactants which boost or increase the microbicidal benefit of a animate surface treatment composition (and/or microbial control system) are present, they may be included in any effective amount which increases or boosts the microbicidal benefit of a animate surface treatment composition (or system) of any aspect of the invention, as compared to a like animate surface treatment composition (and/or microbial control system) where the said surfactant is omitted, and its mass substituted by water. Advantageously such said further detersive surfactants may be present in amounts of as little as 0.001% wt., preferably in amount of at least about 0.05% wt., yet more preferably are present in an amount of at least about 0.1% wt., based on the total weight of the composition (or system) of which said surfactant forms a part.

Non-limiting examples of the major surfactant types that can be used as detersive surfactants of the present invention include those which are known as anionic, nonionic, amphoteric, and zwitterionic surfactants as well as further cationic surfactants which are not primarily present to provide a microbicidal or germicidal benefit. Such include, e.g.: sulfates and sulfonates of oils and fatty acids, sulfates and sulfonates, ethoxylated alkylphenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecylbenzenes, sulfonates of naphthalene and alkyl naphthalene, sulfonates of petroleum, sulfosuccinamates, sulfosuccinates and derivatives, soaps, taurates, thio and mercapto derivatives, tridecyl and dodecyl benzene sulfonic acids, alkanolamides, alkanolamines, alkylaryl sulfonates, alkylaryl sulfonic acids, alkylbenzenes, amine acetates, amine oxides, amines, sulfonated amines and amides, betaine derivatives, block polymers, carboxylated alcohol or alkylphenol ethoxylates, carboxylic acids and fatty acids, ethoxylated alcohols, ethoxylated alkylphenols, ethoxylated amines and/or amides, ethoxylated fatty acids, ethoxylated fatty esters and oils, fatty esters, fluorocarbon-based surfactants, glycerol esters, glycol esters, hetocyclic-type products, imidazolines and imidazoline derivatives, isethionates, lanolin-based derivatives, lecithin and lecithin derivatives, lignin and lignin deriviatives, maleic or succinic anhydrides, methyl esters, monoglycerides and derivatives, olefin sulfonates, phosphate esters, phosphorous organic derivatives, polyethylene glycols, polymeric (polysaccharides, acrylic acid, and acrylamide) surfactants, propoxylated and ethoxylated fatty acid alcohols or alkyl phenols, protein-based surfactants, sarcosine derivatives, silicone-based surfactants, sorbitan derivatives, sucrose and glucose esters and derivatives, as well as further surfactants known to the art but not elucidated here.

Soaps are also considered as useful anionic surfactants. Such include water-soluble or water-dispersible alkali metal salt of an organic acid, especially a sodium salt, or the corresponding ammonium or substituted ammonium salt. Examples of suitable organic acids are natural or synthetic aliphatic carboxylic acids of from 10 to 22 carbon atoms, especially the fatty acids of triglyceride oils such as tallow and coconut oil. Non-limiting examples of preferred soaps of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominantly $C_{14}$ and $C_{18}$ fatty acids, the nut oil fatty acids are of shorter chain length and are predominantly $C_{10}$-$C_{14}$ fatty acids.

Additional non-limiting examples of surfactants that can be used include one or more nonionic surfactants, especially one or more compounds based on the condensation products of alkylene oxide groups with an organic hydrophobic compound, such as an aliphatic compound or with an alkyl aromatic compound. The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic detergent. Further, the length of the polyethenoxy hydrophobic and hydrophilic elements may be varied to adjust these properties. Illustrative examples of such a nonionic surfactant include the condensation product of one mole of an alkyl phenol having an alkyl group containing from 6 to 12 carbon atoms with from about 5 to 25 moles of an alkylene oxide. Another example of such a nonionic surfactant is the condensation product of one mole of an aliphatic alcohol which may be a primary, secondary or tertiary alcohol having from 6 to 18 carbon atoms with from 1 to about 10 moles of alkylene oxide. Preferred alkylene oxides are ethylene oxides or propylene oxides which may be present singly, or may be both present.

Non-limiting, illustrative examples of nonionic surfactants include primary and secondary linear and branched alcohol ethoxylates, such as those based on $C_6$-$C_{18}$ alcohols which further include an average of from 2 to 80 moles of ethoxylation per mol of alcohol. Examples include the Genapol® series of linear alcohol ethoxylates from Clariant Corp., Charlotte, N.C. Further examples of useful nonionic surfactants include secondary $C_{12}$-$C_{15}$ alcohol ethoxylates, including those which have from about 3 to about 10 moles of ethoxylation. Such are available in the Tergitol® series of nonionic surfactants (Dow Chemical, Midland, Mich.), particularly those in the Tergitol® "15-S-" series. Further exemplary nonionic surfactants include linear primary $C_{11}$-$C_{15}$ alcohol ethoxylates, including those which have from about 3 to about 10 moles of ethoxylation. Such are available in the Tomadol® series of nonionic surfactants (Tomah Products, Inc., Milton, Wis.).

Further examples of useful nonionic surfactants include $C_6$-$C_{15}$ straight chain alcohols ethoxylated with about 1 to 13 moles of ethylene oxide, particularly those which include about 3 to about 6 moles of ethylene oxide. Examples of such nonionic surfactants include Alfonic® 810-4.5, which is described as having an average molecular weight of 356, an ethylene oxide content of about 4.85 moles and an HLB of about 12; Alfonic® 810-2, which is described as having an average molecular weight of 242, an ethylene oxide content of about 2.1 moles and an HLB of about 12; and Alfonic® 610-3.5, which is described as having an average molecular weight of 276, an ethylene oxide content of about 3.1 moles, and an HLB of 10.

A further class of nonionic surfactants which may find use in the present inventive compositions include ethoxylated octyl and nonyl phenols include those having one of the following general structural formulas:

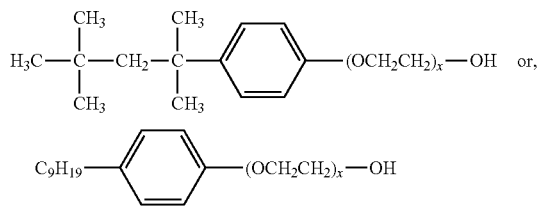

in which the $C_9H_{19}$ group in the latter formula is a mixture of branched chained isomers, and x indicates an average number of ethoxy units in the side chain. Particularly suitable non-ionic ethoxylated octyl and nonyl phenols include those having from about 7 to about 13 ethoxy groups. Such compounds are commercially available under the trade name Triton® X (Dow Chemical, Midland, Mich.), as well as under the tradename Igepal® (Rhodia, Princeton, N.J.). One exemplary and particularly preferred nonylphenol ethoxylate is Igepal® CO-630.

Still further examples of suitable nonionic surfactants which may be advantageously included in the inventive compositions are alkoxy block copolymers, and in particular, compounds based on ethoxy/propoxy block copolymers. Polymeric alkylene oxide block copolymers include nonionic surfactants in which the major portion of the molecule is made up of block polymeric C2-C4 alkylene oxides. Such nonionic surfactants, while preferably built up from an alkylene oxide chain starting group, can have as a starting nucleus almost any active hydrogen containing group including, without limitation, amides, phenols, thiols and secondary alcohols.

One group of such useful nonionic surfactants containing the characteristic alkylene oxide blocks are those which may be generally represented by the formula (A):

$$HO\text{-}(EO)_x(PO)_y(EO)_z\text{-}H \quad (A)$$

where EO represents ethylene oxide,
PO represents propylene oxide,
y equals at least 15,
$(EO)_{x+y}$ equals 20 to 50% of the total weight of said compounds, and,
the total molecular weight is preferably in the range of about 2000 to 15,000.

Another group of nonionic surfactants for use in the new inventive compositions can be represented by the formula (B):

$$R\text{-}(EO,PO)_a(EO,PO)_b\text{-}H \quad (B)$$

wherein R is an alkyl, aryl or aralkyl group, where the R group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the E0 rich block.

Further nonionic surfactants which in general are encompassed by formula (B) include butoxy derivatives of propylene oxide/ethylene oxide block polymers having molecular weights within the range of about 2000-5000.

Still further useful nonionic surfactants containing polymeric butoxy (BO) groups can be represented by formula (C) as follows:

$$RO\text{—}(BO)_n(EO)_x\text{—}H \quad (C)$$

wherein R is an alkyl group containing 1 to 20 carbon atoms, n is about 5-15 and x is about 5-15.

Also useful as the nonionic block copolymer surfactants, which also include polymeric butoxy groups, are those which may be represented by the following formula (D):

$$HO\text{-}(EO)_x(BO)_n(EO)_y\text{—}H \quad (D)$$

wherein n is about 5-15, preferably about 15,
x is about 5-15, preferably about 15, and
y is about 5-15, preferably about 15.

Still further useful nonionic surfactants include ethoxylated derivatives of propoxylated ethylene diamine, which may be represented by the following formula:

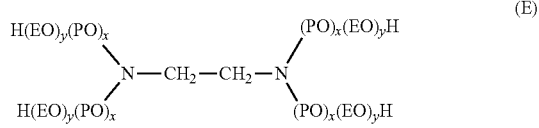

where (EO) represents ethoxy,
(PO) represents propoxy,
the amount of $(PO)_x$ is such as to provide a molecular weight prior to ethoxylation of about 300 to 7500, and the amount of $(EO)_y$ is such as to provide about 20% to 90% of the total weight of said compound.

Further examples of useful nonionic surfactants are one or more amine oxides. Exemplary amine oxides include:

A) Alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide;

B) Alkyl di(hydroxy lower alkyl) amine oxides in which the alkyl group has about 10-20, and preferably 12-16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide;

C) Alkylamidopropyl di(lower alkyl) amine oxides in which the alkyl group has about 10-20, and preferably 12-16 carbon atoms, and can be straight or branched chain, saturated or unsaturated. Examples are cocoamidopropyl dimethyl amine oxide and tallowamidopropyl dimethyl amine oxide; and D) Alkylmorpholine oxides in which the alkyl group has about 10-20, and preferably 12-16 carbon atoms, and can be straight or branched chain, saturated or unsaturated.

Preferably the amine oxide constituent is an alkyl di(lower alkyl) amine oxide as denoted above and which may be represented by the following structure:

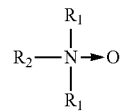

wherein each:
$R_1$ is a straight chained $C_1$-$C_4$ alkyl group, preferably both $R_1$ are methyl groups; and,
$R_2$ is a straight chained $C_8$-$C_{18}$ alkyl group, preferably is $C_{10}$-$C_{14}$ alkyl group, most preferably is a $C_{12}$ alkyl group.

Each of the alkyl groups may be linear or branched, but most preferably are linear. Technical grade mixtures of two or more amine oxides may be used, wherein amine oxides of varying chains of the $R_2$ group are present. Preferably, the amine oxides used in the present invention include $R_2$ groups which comprise at least 50% wt., preferably at least 60% wt. of $C_{12}$ alkyl groups and at least 25% wt. of $C_{14}$ alkyl groups, with not more than 15% wt. of $C_{16}$, $C_{18}$ or higher alkyl groups as the $R_2$ group.

Where an amine oxide surfactant is present, preferably a linear $C_{12\text{-}14}$ alkyl dimethyl amine oxide compound is excluded.

Further specific examples of useful nonionic surfactants are alkanolamide surfactant compounds. Exemplary useful alkanolamides include one or more monoethanol amides, and diethanol amides of fatty acids having an acyl moiety which contains from about 8 to about 18 carbon atoms, and which may be represented in accordance with the formula:

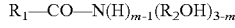

where $R_1$ represents a saturated or unsaturated aliphatic hydrocarbon radical of from about 7 to 21 carbon atoms, but preferably from about 11 to 17 carbon atoms; $R_2$ represents a —$CH_2$— or —$CH_2CH_2$—, and m is an integer from 1 to 3, but is preferably 1. Preferably, $R_1$ is a saturated or unsaturated aliphatic hydrocarbon radical comprising from about 11 to 17 carbon atoms, and m is 1. Specific examples of such compounds include mono-ethanol amine coconut fatty acid amide and diethanol amine dodecyl fatty acid amide. An exemplary useful and particularly preferred fatty acid amides include cocomonoethanol amide or cocodiethanolamide, which are presently commercially available under the Monamid® tradename. Further exemplary useful alkanolamides which provide such functions include inter alia: cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof. Further useful alkanolamide surfactant compounds include alkanolamides, particularly fatty monoalkanolamides and fatty dialkanolamides, including one or more of those marketed under the Nino® tradename. Further exemplary alkanolamide surfactant compounds include monoethanol amides and diethanol amides include those marketed under the trade names Alakamide® and Cyclomide® by Rhône-Poulenc Co., (Cranbury, N.J.) e.g., Cyclomide® CDD-518 described to be a nonionic surfactant based on coconut diethanolamide; Cyclomide® C212 described to be a nonionic surfactant based on coconut monoethanolamide; Cyclomide® DC212/SE described to be a nonionic surfactant based on 1:1 fatty acid diethanolamide; Cyclomide® DIN 100 described to be a nonionic surfactant based on lauric/linoleic diethanolamide; Cyclomide® DIN-295/S described to be a nonionic surfactant based on 1:1 linoleic diethanolamide; Cyclomide® DL203 described to be a nonionic surfactant based on 2:1 lauric diethanolamide.

Further specific examples of useful nonionic surfactants include alkyl polyglycosides. The alkyl polyglycosides which can be used as nonionic surfactants in the composition are generally represented by the formula:

$$R_1O(R_2O)_b(Z)_a$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides have the formula I wherein Z is a glucose residue and b is zero. Such alkyl polyglycosides are commercially available, for example, as APG®, GLUCOPON®, or PLANTAREN® surfactants from Cogis Corp. Specific examples of such surfactants include but are not limited to: APG® 225, described to be an alkyl polyglycoside in which the alkyl group contains 8 to 10 carbon atoms and having an average degree of polymerization of 1.7; GLUCOPON® 425, described to be an alkyl polyglycoside in which the alkyl group contains 8 to 16 carbon atoms and having an average degree of polymerization of 1.48; GLUCOPON® 625, described to be an alkyl polyglycoside in which the alkyl group contains 12 to 16 carbon atoms and having an average degree of polymerization of 1.6; APG® 325, described to be an alkyl polyglycoside in which the alkyl group contains 9 to 11 carbon atoms and having an average degree of polymerization of 1.5; GLUCOPON® 600, described to be an alkyl polyglycoside in which the alkyl group contains 12 to 16 carbon atoms and having an average degree of polymerization of 1.4; PLANTAREN® 2000, described to be an alkyl polyglycoside in which the alkyl group contains 8 to 16 carbon atoms and having an average degree of polymerization of 1.4; and, PLANTAREN® 1300, described to be an alkyl polyglycoside in which the alkyl group contains 12 to 16 carbon atoms and having an average degree of polymerization of 1.6. Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and R.sub.1 is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70-95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6-20 carbon atoms and a suitable saccharide from which excess alcohol has been separated.

Also useful as nonionic surfactants are ethylene oxides condensed with sorbitan fatty acid esters. Such materials are presently commercially available under the tradename TWEEN (ex. ICI) and/or CRILL (ex. Croda) which include polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleates which are available in a variety of grades, and with differing amounts of polyoxylethylene groups per molecule.

The inventive compositions most desirably, although not always essentially, include at least one nonionic surfactant. Such is a detersive surfactant constituent. An example of an especially preferred nonionic surfactant is at least one alcohol ethoxylate based nonionic surfactant in an amount of from about 0.01-40% wt. In order of increasing preference, when present, the at least one nonionic surfactant comprises in % wt. at least 0.025, 0.05, 0.075, 0.1, 0.2, 0.25, 0.3, 0.4, 0.5, 0.6, 0.75, 0.8, 0.9, 1, 1.5, 2, 3, 4, 5, 6, 7, 8, 9, 10, 15, 20, 25, 30, 35 and 40% wt. and similarly the at least one nonionic surfactant comprises, in % wt., not more than about 40% wt. based on the total weight of an animate surface treatment composition of which they form a part.

In certain preferred embodiments, at least one detersive surfactant, preferably at least one nonionic surfactant, is a necessary constituent of the inventive compositions. While not wishing to be bound by the following, it is suspected that the presence of at least one surfactant and especially at least one nonionic surfactant aids in the penetration of organic soils and/or the penetration of one or more undesired microorganisms and hastens the activity of the essential constituents, viz. the copper ions provided by the source of copper ions, and/or the lower alkyl aliphatic monohydric alcohol in reducing, deactivating or destroying these undesired microorganisms and thus may aid in both providing an improved speed and/or degree of control, reduction or elimination of the one or more undesired microorganisms being treated with the treatment compositions taught herein.

Especially preferred nonionic surfactants and the amounts in which they are preferably present are disclosed with reference to one or more of the Examples. In certain embodiments at least one detersive surfactant, and preferably at least one nonionic surfactant is necessarily present and is considered as a further essential constituent of the invention.

Non-limiting examples of further surfactants which may be included in the treatment compositions of the invention include zwitterionic and amphoteric surfactants. Zwitterionic surfactants may also be present either by themselves or in admixture with another ionic surfactant providing there are no troublesome interactions. Typical examples of amphoteric or zwitterionic surfactants are alkyl betaines, alkyl amidobetaines, aminopropionates, aminoglycinates, imidazolinium betaines and sulfobetaines. Within this group, alkyl betaines and alkyl amidobetaines are particularly preferred. Alkyl betaines are known surfactants which are mainly produced by carboxyalkylation, preferably carboxymethylation of aminic compounds. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, C12/14 cocoalkyl dimethyl amine, myristyl dimethyl amine, cetyl dimethyl amine, stearyl dimethyl amine, stearyl ethyl methyl amine, oleyl dimethyl amine, C16/18 tallow alkyl dimethyl amine and technical mixtures thereof.

Alkyl amidobetaines which represent carboxyalkylation products of amidoamines are also suitable for use in the animate treatment compositions. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethyl amine, N,N-dimethylaminoproply amine, N,N-diethylaminoethyl amine and N,N-diethylaminoproply amine which are condensed with sodium chloroacetate. The condensation product of C8/18 cocofatty acid-N,N-dimethylaminopropyl amide with sodium chloroacetate is preferably used.

Further specific examples of particular amphoteric surfactants which may be used in the animate surface treatment compositions of the invention include one or more amphoteric surfactants. Exemplary amphoteric surfactants include alkylampho(mono)acetates, alkylampho(di)acetates, alkylampho(mono)propionates, and alkylampho(di)propionates. Examples of these amphoteric surfactants can be found under the tradename Miranol from Rhodia (Cranbury, N.J.). Some examples include Miranol C2M-Conc. NP, described to be disodium cocoamphodiacetate; Miranol FA-NP, described to be sodium cocoamphotacetate; Miranol DM, described to be sodium steroamphoacetate; Miranol HMA, described to be sodium lauroamphoacetate; Miranol C2M, described to be cocoamphodiprioponic acid; Miranol C2M-SF, described to be disodium cocoamphodiproprionate; Miranol CM-SF Conc., described as being cocoamphopropriate; Mirataine H2C-HA, described as sodium lauiminodiproprionate; Miranol Ultra L-32, described as sodium lauroamphoacetate; and Miranol Ultra C-37, described as sodium cocoamphoacetate. Other amphoteric surfactants are also available under the tradename Amphoterge from Lonza (Fair Lawn, N.J.) such as Amphoterge K described to sodium cocoamphoproprionate; Amphoterge K-2, described as disodium cocoamphodiproprionate; Amphoterge W, described to be sodium cocoamphoacetate; and Amphoterge W-2, described to be disodium cocoamphodiacetate.

Further useful amphoteric surfactants include those which may be represented by the following general formula

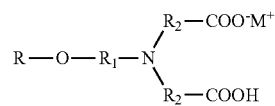

in which, R represents a $C_4$ to $C_{24}$ alkyl group, and is preferably a C10 to C16 alkyl group, R1 and R2 independently represent a $C_1$ to $C_8$ alkyl group, is preferably —CH$_2$CH$_2$— or —CH$_2$CH$_2$CH$_2$—, and M may be any salt-forming anion which permits water solubility or water miscibility of the compound, e.g., chloride, bromide, methosulfate, ethosulfate, lactate, saccharinate, acetate or phosphate. Such compounds are presently commercially available, such as those marketed in the Tomamine Amphoteric series of amphoteric surfactants, ex. Air Products Inc.

While the one or more detersive surfactants may be present in any effective amount which may be observed to improve the microbicidal efficacy of the system of the essential constituents, these one or more surfactants, when present, are advantageously present in an amount of from about 0.001-99% wt., preferably from about 0.1-60% wt., based on the total weight of the treatment composition (or microbicidal system) within which they are present. In certain preferred embodiments the one or more detersive surfactants comprise in excess of 1% wt. of an animate treatment composition, preferably in excess of 1% wt. to about 30% wt., and preferably comprise at least about 5% wt. of an animate treatment composition of which they form a part.

While in certain preferred embodiments the animate surface treatment compositions necessarily include at least at least one further detersive surfactant, (which is preferably a nonionic surfactant) other than a germicidally effective quaternary ammonium compound, which least one further detersive surfactant which provides an ancillary microbicidal benefit within the treatment composition of which it forms a part, as compared to where such at least one such further detersive surfactant is absent from said composition, such is however not an absolute requirement in the selection of one or more detersive surfactants. Rather it is to be clearly understood that compositions of the invention may include one or more further detersive surfactants which provide no ancillary microbiocidal benefit within the treatment compositions, particularly wherein a detersive benefit, a cleaning benefit, a foaming benefit, or a lathering benefit are desired to be provided in the animate surface treatment compositions taught herein.

As the inventive compositions may be in part, aqueous, water may be added in order to provide to 100% by weight of the compositions of the invention. The water may be tap water, but is preferably distilled and is most preferably deionized water. If the water is tap water, it is preferably substantially free of any undesirable impurities such as organics or inorganics, especially minerals salts which are present in hard water and which may undesirably interfere with the operation of the constituents present in the aqueous compositions according to the invention.

As the animate treatment compositions are advantageously used in personal care products, e.g., topical compositions, hair treatment compositions, skin treatment compositions, cosmetics, and personal care compositions, the compositions of the invention may also include one or more conventional constituents which are conventionally present in personal care products. Such include materials identified in the *Compilation of Ingredients Use in Cosmetics in the United States*, 1$^{st}$ Ed. (2012) published by the Personal Care Products Council (Washington, D.C.) Thus, certain additives and adjuvants which are conventional in the cosmetic, pharmaceutical or dermatological field, specifically hydrophilic or lipophilic gelling agents, hydrophilic or lipophilic active agents, humectants, opacifiers, emollients, light stabilizers including UV absorbers, and Polyquaternium type polymers may also be present in effective amounts.

The animate surface treatment compositions may include volatile oils or non-volatile oils. Such oils preferably are pourable liquids at room temperature (e.g., 20° C.). Such may be volatile (having a vapor pressure of at least 2 mm Hg at 20° C.) or non-volatile (having a vapor pressure of not more than 2 mm Hg at 20° C.). Such oils comprise one or more of esters, fatty acids and alcohols, polyols and hydrocarbons as well as further materials which may impart a softening effect when topically applied, e.g. function as emollients.

Such oils include esters including mono-, di- and triesters. Monoesters include esters formed by the reaction of a monocarboxylic acid having the formula R—COOH, wherein R is a straight or branched chain saturated or unsaturated alkyl having 2 to 30 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups, e.g., is an alpha hydroxy acid. Either one or both of the acid or alcohol may be a "fatty" acid or alcohol, i.e., may have from about 6 to 22 carbon atoms. Examples of monoester oils that may be used in the compositions of the invention include hexyldecyl benzoate, hexyl laurate, hexadecyl isostearate, hexyldecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, cetyl octanoate, cetyl laurate, cetyl lactate, isostearyl isononanoate, cetyl isononanoate, cetyl stearate, stearyl lactate, stearyl octanoate, stearyl heptanoate, stearyl stearate, and so on. It is understood that in the above nomenclature, the first term indicates the alcohol and the second term indicates the acid in the reaction, i.e. stearyl octanoate is the reaction product of stearyl alcohol and octanoic acid. Diesters include the reaction product of a dicarboxylic acid and an aliphatic or aromatic alcohol. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. The aliphatic or aromatic alcohol may be substituted with one or more substitutents such as hydroxyl. Preferably, one or more of the acid or alcohol is a fatty acid or alcohol, i.e. contains 14-22 carbon atoms. The dicarboxylic acid may also be an alpha hydroxy acid. Examples of diester oils that may be used in the compositions of the invention include diisostearyl malate, neopentyl glycol dioctanoate, dibutyl sebacate, di-$C_{12}$-$C_{13}$ alkyl malate, dicetearyl dimer dilinoleate, dicetyl adipate, diisocetyl adipate, diisononyl adipate, diisostearyl dimer dilinoleate, disostearyl fumarate, diisostearyl malate, and the like. Triesters include the reaction product of a tricarboxylic acid and an aliphatic or aromatic alcohol. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 14-22 carbon atoms. Examples of triesters include triarachidin, tributyl citrate, triisostearyl citrate, tri $C_{12}$-$C_{13}$ alkyl citrate, tricaprylin, tricaprylyl citrate, tridecyl behenate, trioctyldodecyl citrate, tridecyl behenate, tridecyl cocoate, tridecyl isononanoate, and the like.

Further oils include fatty alcohols and acids thereof which include, inter alia, those compounds having from 10 to 20 carbon atoms, preferentially cetyl, myristyl, palmitic and stearyl alcohols and acids.

Further such oils include polyols which include, inter alia, linear and branched chain alkyl polyhydroxyl compounds such as, propylene glycol, sorbitol and glycerin. Further useful emollients include polymeric polyols, inter alia, polypropylene glycol and polyethylene glycol. Exemplary hydrocarbons which may serve as emollients are those having hydrocarbon chains anywhere from 12 to 30 carbon atoms, particularly, mineral oil, petroleum jelly, mineral oil, pentahydrosqualene, squalene, squalane, and mixtures thereof. Lanolin oil, and derivatives thereof such as derivatives containing hydroxyl, alkyl, or acetyl groups, such as hydroxylated lanolin, isobutylated lanolin oil, acetylated lanolin, acetylated lanolin alcohol, and the like may also be present as oils and are also useful to provide an emollient effect.

Examples of volatile oils include linear and cyclic silicones, including those cyclic silicones which conform to the general formula:

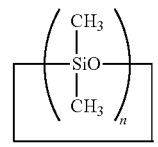

wherein n=2-12, preferably 3-6,
and linear silicones which conform to the general formula:

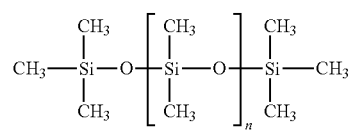

wherein n is 0, or is an integer of 1 or greater, preferably n=0-12, more preferably 0-5, and optionally one of the methyl groups of the foregoing linear silicone formula may be replaced with an alkyl group (e.g. of 2 to 10 carbon atoms) to provide an alkylmethylsiloxane. Such linear and cyclic silicones comprise octamethylcyclotetrasiloxane, decamethylcyclopentasiloxane, hexamethyldisiloxane, 3-hexylheptamethyltrisiloxane, octamethyltrisiloxane, dodecamethylpentasiloxane, and mixtures thereof, and include commercially available materials such as the Dow Corning 200 Fluid, Dow Corning 244 Fluid, Dow Corning 245 Fluid, Dow Corning 344 Fluid, DM Fluid 0.65 cs, DM Fluid 1.5 cs, DM Fluid 2.0 cs, DC 2-1184 and DC 2-1731, all of which are available from Dow Corning or other commercial sources.

Further examples of volatile oils include various straight or branched chain paraffinic hydrocarbons having 5 to 40 carbon atoms, more preferably 8-20 carbon atoms. Preferred paraffinic hydrocarbons include pentane, hexane, heptane, decane, dodecane, tetradecane, tridecane, and $C_8$-$C_{20}$ isoparaffins such as isodecane, preferred of which are those having a molecular weight of 70-225, and a boiling point in the range of 30-320° C., preferably 60-260° C. Such include materials currently available under the tradename Isopar® (ex Exxon) as well as under the Permethyl® tradename (ex. Permethyl Corp.)

Examples of non-volatile oils include non-volatile liquid oils such as silicones, esters, and the like. In the case where it is desired to make long wearing cosmetic products, if the nonvolatile oils are too heavy or greasy it may hamper the long wearing characteristics of the invention. In such a case, the viscosity of the nonvolatile oils, if present, should range from about 11-1000, preferably less than 100 centipoise, most preferably less than about 50 centipoise at 25° C. Examples of such oils include polyalkylsiloxanes, polyarylsiloxanes, and polyethersiloxanes, as well as non-volatile silicones such as dimethicone, phenyl trimethicone, dimethicone copolyol, and the like.

Further non-volatile oils include lower viscosity organic liquids including saturated or unsaturated, substituted or unsubstituted branched or linear or cyclic organic compounds that are liquid under ambient conditions, viz., at normal atmospheric pressure and a temperature of about 20-25° C. Such non-volatile oils generally have a viscosity of greater than 10 centipoise at 25° C. and may range in viscosity up to about 1,000,000 centipoise at said temperature.

Further examples of non-volatile oils include naturally occurring glyceryl esters of fatty acids, or triglycerides. Both vegetable and animal sources may be used. Examples of such oils include castor oil, lanolin oil, $C_{10}$-$C_{18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like. Also useful are synthetic or semi-synthetic glyceryl esters, e.g. fatty acid mono-, di-, and triglycerides which are natural fats or oils that have been modified, for example, acetylated castor oil, or mono-, di- or triesters of polyols such as glyceryl stearate, diglyceryl diiosostearate, polyglyceryl-4 isostearate, polyglyceryl-6 ricinoleate, glyceryl dioleate, glyceryl diisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and the like.

Further useful non-volatile oils include non-volatile silicone oils. By way of non-limiting example such include non-volatile silicone oils which may be water insoluble such as amine functional silicones such as amodimethicone; phenyl substituted silicones such as bisphenylhexamethicone, phenyl trimethicone, or polyphenylmethylsiloxane; dimethicone, alkyl substituted dimethicones, and mixtures thereof, as well as those which are water soluble such as dimethicone copolyol, dimethiconol, and the like.

Further useful oils include various fluorinated oils such as fluorinated silicones, such as trimethylsilyl endcapped fluorosilicone oil, polytrifluoropropylmethylsiloxanes, fluorinated esters, perfluoropolyethers, and the like.

Any one or more of the foregoing volatile oils or non-volatile oils may be present in the animate surface treatment compositions in any effective amount in order to provide a desired technical or aesthetic benefit. Advantageously, when present, one or more of the foregoing volatile oils or non-volatile oils may is present in an amount of at least about 0.01% wt., preferably is present in an amount of from about 0.001% wt. to about 10% wt., based on the total weight of the composition of which the one or more volatile oils or non-volatile oils form a part.

The treatment compositions of the invention may include one or more further organic solvents, which are differentiated from the alkyl aliphatic monohydric alcohol constituent which is an essential constituent according to certain aspects of the invention, although optional in all other aspects of the invention. Such further optional organic solvents may include one or more of: alcohols other than the essential lower alkyl aliphatic monohydric alcohol described previously, glycols, acetates, ether acetates, glycerols, as well as polyethylene glycols and glycol ethers. Mixtures of these further optional organic solvents can also be used. Typically such further one or more organic solvents are ones which have no appreciable microbicidal effect and are thus differentiated from the essential alkyl aliphatic monohydric alcohol constituent. Non-limiting examples of useful glycol ethers and examples include those glycol ethers having the general structure $R_a$—O—[$CH_2$—CH(R)—($CH_2$)—O]$_n$—H, wherein $R_a$ is $C_{1-20}$ alkyl or alkenyl, or a cyclic alkane group of at least 6 carbon atoms, which may be fully or partially unsaturated or aromatic; n is an integer from 1 to 10, preferably from 1 to 5; each R is selected from H or $CH_3$; and a is the integer 0 or 1. Specific and preferred solvents are selected from propylene glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, diethylene glycol monoethyl ether acetate and the like. When present such further optional one or more organic solvents may be present in any effective amount, preferably in amounts of between about 0.001-10% wt., and preferably between about 0.01-5% wt. based on the total weight of the treatment composition of which they form a part.

The treatment compositions of the invention may include one or more film-forming constituents. Such are advantageously present to provide a coating or barrier layer to dermal surfaces and/or keratinous surfaces. Non-limiting examples of film forming agents can be chosen from anionic compounds, non-ionic compounds, amphoteric compounds, zwitterionic compounds, proteins, viscosity modifiers, cationic polymers, polyamides, polyaminoamides, polyesters, silicone resins, polysaccharides, silicone fluids, polyacrylamides, starches, gums and mixtures thereof. When such are included, they may be present in any effective amount. When present one or more such film forming constituents are preferably present in an amount of between about 0.001-10% wt., and preferably between about 0.01-5% wt. based on the total weight of the treatment composition of which they form a part.

A further optional constituent which nonetheless may be advantageously present are one or more compounds or materials which absorb a significant percentage (e.g., at least about 75%) of ambient ultraviolet (UVA) light, particularly UVA radiation in the range of about 320-400 nanometers. Nonlimiting examples of preferred UVA radiation absorbing compounds and materials include dibenzoylmethane compounds such as 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxy-dibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and the like. When present, such UVA radiation absorbing compounds and materials may be present in any effective amounts, but advantageously when present, are included in the animate surface treatment compositions in amounts of at least about 0.0001% wt., preferably in amounts of from about 0.001% wt.-5% wt.

A further optional constituent which nonetheless may be advantageously present are one or more compounds or materials which absorb a significant percentage (e.g., at least about 75%) of ambient ultraviolet (UVB) light, particularly UVB radiation in the range of about 280-320 nanometers. Nonlimiting examples of preferred UVB radiation absorbing compounds and materials include α-cyano-β,β-diphenyl acrylic acid esters, such as 2-ethylhexyl 2-cyano-3,3-diphenylacrylate, as well as octocrylene, which is commercially available as Uvinul® N-539 (ex. BASF). Also useful as UVB radiation absorbing compounds include benzylidene camphor derivatives, e.g, 4-methylbenzylidene camphor, which is commercially available as Eusolex® 6300 (ex. Merck), cinnamate derivatives such as ethylhexyl methoxycinnamate, which is also frequently referred to as Octoxinate or octyl methoxycinnamate. mono-, di-, and triethanolamine derivatives of such methoxy cinnamates including diethanolamine methoxycinnamate, benzophenone derivatives, Benzophenone 1, 2, 3, 4, 5, 6, 7, 8, 9, 10, 11, and 12. Particularly preferred is where the benzophenone derivative is Benzophenone 3 (also referred to as Oxybenzone) and Benzophenone 4 (also referred to as Sulisobenzone), Benzophenone 5 (Sulisobenzone Sodium), menthyl salicylate derivatives including homomethyl salicylate (also known as Homosalate) or menthyl anthranilate, amino benzoic acid derivatives including PABA, ethyl hexyl dimethyl PABA (Padimate 0), ethyldihydroxypropyl PABA, as well as salicylate derivatives such as octyl salicylate, TEA-salicylcate, DEA-salicylate, and mixtures thereof. When present such UVB radiation absorbing compounds and materials may be present in any effective amounts, but advantageously when present, are included in the animate surface treatment compositions in amounts of at least about 0.0001% wt., preferably in amounts of from about 0.001% wt.-50% wt.

The animate treatment compositions of the invention may optionally further comprise one or more vitamins, antioxidants and/or coenzymes. Nonlimiting examples of vitamins include one or more of Vitamin A and derivatives thereof such as Vitamin A palmitate, acetate, or other esters thereof, as well as Vitamin A in the form of beta carotene, Vitamin C such as ascorbic acid and derivatives thereof, the B vitamins such as thiamine, riboflavin, pyridoxin, and the like, Vitamin E and derivatives thereof such as Vitamin E acetate, nicotinate, or other esters thereof, as well as Vitamin D and Vitamin K. Nonlimiting examples of coenzymes include one or more of thiamine pyrophosphate, flavin adenin dinucleotide, folic acid, pyridoxal phosphate, tetrahydrofolic acid, and the like. Nonlimiting examples of antioxidants include one or more of potassium sulfite, sodium bisulfite, sodium erythrobate, sodium metabisulfite, sodium sulfite, propyl gallate, cysteine hydrochloride, butylated hydroxytoluene, butylated hydroxyanisole, and the like.

When present, such one or more vitamins, antioxidants and/or coenzymes are present in effective amounts, and when present, advantageously comprise at least about 0.001% wt. of the composition of which it forms a part. Preferably one or more of said vitamins, antioxidants and/or coenzymes comprise from about 0.002% wt. to about 5% wt.

The animate treatment compositions of the invention may optionally further comprise one or more humectants. Nonlimiting examples of such humectants include one or more of di- or polyhydric alcohols such as glycols, sugars, and similar materials. Suitable glycols include alkylene glycols such as propylene, ethylene, or butylene glycol; or polymeric alkylene glycols such as polyethylene and polypropylene glycols, including PEG 4-240, which are polyethylene glycols having from 4 to 240 repeating ethylene oxide units. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and the like. When present, such one or more humectants may be present in any effective amount, and advantageously comprise at least about 0.001% wt. of the composition of which it forms a part. When present, preferably the one or more humectants comprise about 0.001-8% wt. of the animate surface treatment composition of which it forms a part.

The animate surface treatment compositions of the invention may also include one or more Polyquaternium type polymers, as, while such are not necessary to provide the microbicidal benefits of the inventive compositions, such may provide a useful technical benefits, including but not limited to: a film forming benefit, a topical barrier, and additional thickening benefits to the inventive compositions, or other technical benefits. Such materials, are, per se, well known to the art of topical compositions. Various grades of such cationic polymers may be used, inter alia: Polyquaternium 1; Polyquaternium 2; copolymers of hydroxyethylcellulose and diallyldimethyl ammonium chloride commercially available as Polyquaternium 4; homopolymers of diallyldimethylammonium chloride commercially available as Polyquaternium 5; dimethyldiallyammonium chloride homopolymer commercially available as Polyquaternium 6; copolymers of diallyldimethylammonium chloride with acrylamide commercially available as Polyquaternium 7; the polymeric quaternary ammonium salt of methyl and steardyl dimethylaminoethyl methacrylate quaternized with dimethyl sulfate commercially available as Polyquaternium 8; the polymeric quaternary ammonium salt of polydimethylaminoethyl methacrylate quaternized with methyl bromide commercially available as Polyquaternium 9; a polymeric quaternary ammonium salt formed from the reaction of hydroxyethyl cellulose with a trimethylammonium substituted epoxide commerically available as Polyquaternium 10; a polymeric quaternary ammonium polymer formed by the reaction of vinyl pyrrolidine and dimethyl aminoethylmethacrylate commercially available as Polyquaternium 11; a polymeric quaternary ammonium salt prepared by the reaction of ethyl methacrylate/abietyl methacrylate/diethylaminoethyl methacrylate copolymer with dimethyl sulfate commercially available as Polyquaternium 12; a polymeric ammonium salt prepared by the reaction of ethyl methacrylate/oleyl methacrylate/diethylaminoethyl methacrylate copolymer with dimethyl sulfate commercially available as Polyquaterinum 12; a polymeric quaternary ammonium salt prepared by the reaction of ethyl methacrylate/oleyl methacralte/diethylaminoethyl methacrylate copolymer with dimethyl sulfate commercially available as Polyquaternium 13; Polyquaternium 14; the copolymer of methacrylamide and betamethacryloxyethyl trimethyl ammonium chloride commercially available as Polyquaternium 15; the polymeric quaternary ammonium salt formed from methylvinylimidazolium chloride and vinylpyrrolidone commercially available as Polyquaternium 16; polymeric quaternary salts prepared by the reaction of adipic acid and dimethylaminopropylamine reached with dichloroethyl ether commercially available as Polyquaternium 17; a polymeric quaternary salt prepared by the reaction of azelaic acid and dimethylaminopropylamine reacted with dichloroethyl ether commercially available as Polquaternium 18; a polymeric quaternary ammonium salt prepared by the reaction of polyvinyl alcohol with 2,3-epoxy-propylamine commercially available as Polyquaternium 19; a polymeric quaternary ammonium salt prepared by the reaction of polyvinyl octadecyl ether with 2,3-epoxypropylamine commercially available as Polyquaternium 20; copolymers of acrylic acid and dimethyldiallylammonium chloride commercially available as Polyquaternium 22; polymeric quaternary ammonium salts of hydroxyethyl cellulose reacted with lauryl dimethyl ammonium-substituted epoxide commercially available as Polyquaternium 24; a block copolymer formed by the reaction of Polyquaternium 2 and Polyquaternium17 commercially available as Polyquaternium 27; a polymeric quaternary ammonium salt consisting of vinylpyrrolidone and dimethylaminopropyl methacrylamide monomers commercially available as Polyquaternium 28; chitosans reacted with propylene oxide and quaternized with epichlorohydrin commercially available as Polyquaternium 29; Polyquaternium 30; a polymeric quaternary ammonium salt prepared by the reaction of DMAPA acrylates/acrylic acid/acrylonitrogens copolymer with diethyl sulfate commercially available as Polyquaternium 31; Polyquaternium 32; Polyquaternium 33; Polyquaternium 34; Polyquaternium 35; Polyquaternium 36; Polyquaternium 37; polymeric quaternary ammonium salts of the terpolymer of acrylic acid/diallyldimethylammonium chloride/acrylamide commercially available as Polyquaternium 39; Polyquaternium 42; a copolymer of acrylamide, acrylamidopropyltrimonium chloride, 2-amidopropylacrylamide sulfonate and DMAPA polymers commercially available as Polyquaternium 43; a polymeric quaternary ammonium salt consisting of vinylpyrrolidone and quaternized imidazoline monomers commercially available as Polyquaternium 44; Polyquaternium 45; a polymeric quaternary ammonium salt prepared by the reaction of vinylcaprolactam and vinylpyrrolidone with methylvinylimidazolium commercially available as Polyquaternium 46; a polymer quaternary ammonium chloride formed by the polymerization of acrylic acid with methacrylamidopropyl trimethylammonium chloride and methylacrylate commercially available as Polyquaternium 47; a copolymer of methacryloyl ethyl betaine, 2-hydroxyethyl methacrylate and metacyloyl ethyl trimethyl ammonium chloride commercially available as Polyquaternium 48; a copolymer of methacryloyl ethyl betaine, PEG-9 methacrylate and methacryloyl ethyl trimethyl ammonium chloride commercially available as Polyquaternium 49; Polyquaternium 50; Polyquaternium 51; Polyquaternium 52; a copolymer of acrylic acid, acrylamide and methacrylamidopropyltrimonium chloride commercially available as Polyquaternium 53; a polymeric quaternary ammonium salt prepared by the reaction of aspartic acid and C6-C18 alkylamine with dimethylaminopropylamine and sodium chloroacetate commercially available as Polyquaternium 54; a polymeric quaternary ammonium chloride formed by the reaction of vinylpyrrolidone, dimethylaminopropyl methacrylamide and methacryloylaminopropyl lauryldimonium chloride commercially available as Polyquaternium 55; and a polymeric quaternary ammonium salt consisting of isophorone diisocyanate, butylene glycol and dihydroxyethyldimonium methosulfate monomers commercially available as Polyquaternium 56. Each of the foregoing are described in the literature, particularly in the International Cosmetic Ingredient Dictionary and Handbook, Volume 2 (9th Edition, 2002), at pages 1311-1319.

When present in the inventive compositions, the one or more Polyquaternium-type polymers are advantageously present in amounts of from about from 0.001-5% wt., preferably in amounts from 0.01-2.5% wt., based on the total weight of the inventive composition of which they form a part.

In certain embodiments of the invention, one or more of the foregoing Polyquaternium type polymers may be excluded from the animate surface treatment compositions.

The animate surface treatment compositions of the invention may also include one or more further compounds, constituents or materials which provide an ancillary microbicidal benefit or effect. These are distinguished from the essential constituents of the invention described above. When present, they may be included in amounts which are effective in order to provide an ancillary microbicidal benefit. Non-limiting examples of such materials include non-cationic microbicidal agents which are particularly useful in the present invention: benzoyl peroxide, pyrithiones (especially zinc pyrithione which is also known as ZPT), dimethyldimethylol hydantoin (Glydant), methylchloroisothiazolinone/methylisothiazolinone (Kathon CG), sodium sulfite, sodium bisulfite, imidazolidinyl urea (Germall 115), diazolidinyl urea (Germaill II), benzyl alcohol, 2-bromo-2-nitropropane-1,3-diol (Bronopol), formalin (formaldehyde), iodopropenyl butylcarbamate (Polyphase P100), chloroacetamide, methanamine, methyldibromonitrile glutaronitrile (1,2-Dibromo-2,4-dicyanobutane or Tektamer), glutaraldehyde, 5-bromo-5-nitro-1,3-dioxane (Bronidox), phenethyl alcohol, o-phenylphenol/sodium o-phenylphenol, sodium hydroxymethylglycinate (Suttocide A), polymethoxy bicyclic oxazolidine (Nuosept C), dimethoxane, thimersal dichlorobenzyl alcohol, captan, chlorphenenesin, dichlorophene, chlorbutanol, glyceryl laurate, halogenated diphenyl ethers like 2,4,4-trichloro-2-hydroxy-diphenyl ether (Triclosan or TCS), 2,2-dihydroxy-5,5-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m,m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4-chloro 2,4-dihydroxydiphenyl methane, 5-bromo 2,4-dihydroxydiphenyl methane, and 4-bromo 2,4-dihydroxydiphenyl methane, bisphenolic compounds like 2,2-methylene bis(4-chlorophenol), 2,2-methylene bis(3,4,6-trichlorophenol), 2,2-methylene bis(4-chloro-6-bromophenol), bis(2-hydroxy-3,5-dichlorophenyl) sulphide, and bis(2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4-trichlorocarbanilides (Triclocarban or TCC), 3-trifluoromethyl-4,4-dichlorocarbanilide, 3,3,4-trichlorocarbanilide, etc.).

Of these, preferred are phenol based non-cationic microbicidals, especially those based on one or more phenolic compounds, particularly 2-hydroxydiphenyl compounds which may be exemplified by the following classes of compounds:

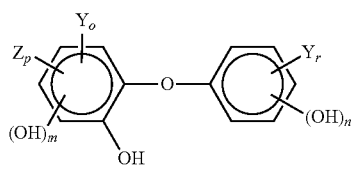

wherein Y is chlorine or bromine, Z is $SO_2H$, $NO_2$, or $C_1$-$C_4$ alkyl, r is 0 to 3, o is 0 to 3, p is 0 or 1, m is 0 or 1, and n is 0 or 1. In preferred embodiments, Y is chlorine or bromine, m is 0, n is 0 or 1, o is 1 or 2, r is 1 or 2, and p is 0, and according to especially preferred embodiments, Y is chlorine, m is 0, n is 0, o is 1, r is 2, and p is 0.

Particularly useful 2-hydroxydiphenyl compounds include those which may be represented by the structure:

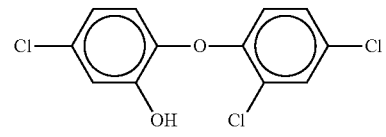

which is commonly referred to as "TRICLOSAN" and which is presently commercially available from Ciba Specialty Chemicals Corp., as well as halogenated carbanilides, e.g., TCC.

Further exemplary useful phenolic based disinfecting agents include 2,2'-hydroxy-5,5'-dibromo-diphenyl ether which may be represented by the structure:

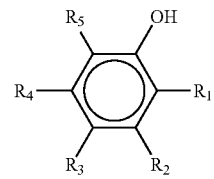

wherein $R_1$ is hydro, hydroxy, $C_1$-$C_4$ alkyl, chloro, nitro, phenyl, or benzyl; $R_2$ is hydro, hydroxy, $C_1$-$C_6$ alkyl, or halo; $R_3$ is hydro, $C_1$-$C_6$ alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid.

Still further useful phenol derivatives include those which may be represented by the structure:

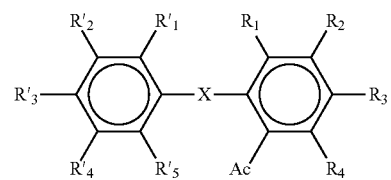

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5%5,5% 6,6'-hexachlorodiphenyl sulfide, and 3,3'-dibromo-5,5'-dichloro-2,2'-dihydroxydiphenylamine. Of the foregoing, a particularly useful phenol derivative is commonly referred to as triclocarban, or 3,4,4'-trichlorocarbanilide as well as derivatives thereto. When present, one or more such further compounds, constituents or materials which provide an ancillary microbicidal benefit or effect may be present in effective amounts, e.g., in amounts of up to about 5% wt., although depending upon the efficacy of one or more selected such further compounds, constituents or materials are usually effective in reduced amounts, e.g., 0.001-2% wt. of the treatment composition.

The treatment compositions of the invention may optionally include a fragrance constituent, which may be based on natural and/or synthetic fragrances and most commonly are mixtures or blends of a plurality of such fragrances, optionally in conjunction with a carrier such as an organic solvent or a mixture of organic solvents in which the fragrances are dissolved, suspended or dispersed. Such may be natural fragrances, e.g, natural extracts of plants, fruits, roots, stems, leaves, wood extracts, e.g. terpineols, resins, balsams, animal raw materials, e.g., civet and beaver, as well as typical synthetic perfume compounds which are frequently products of the ester, ether, aldehyde, ketone, alcohol and hydrocarbon type, e.g., benzyl acetate, linalyl acetate, citral, citronellal, methyl cedryl ketone, eugenol, isoeugenol, geraniol, linalool, and Typically it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, limeblossom oil, juniper berry oil, vetiver oil, olibanum oil, *galbanum* oil, labolanum oil and lavendin oil. When present in a treatment composition, in accordance with certain of the preferred embodiments, the fragrance constituent may be present in any effective amount such that it can be discerned by a consumer of the composition, however such is advantageously present in amounts of up to about 1% wt., preferably in amounts of from about 0.00001% wt. to about 0.5% wt., and most preferably in an amount of from about 0.0001% wt. to 0.5% wt. based on the total weight of the treatment composition of which it forms a part.

The animate treatment compositions of the invention may optionally further comprise one or more botanical extracts. Such are to be understood to be in addition to any fragrance or perfume constituent which might also be concurrently present, or one or more of such botanical extracts may also provide a fragrancing benefit as well Nonlimiting examples of suitable botanical extracts include one or more extracts from plants (herbs, roots, flowers, fruits, seeds) such as flowers, fruits, vegetables, and so on, including acacia (*dealbata*, farnesiana, senegal), *acer saccharinum* (sugar maple), acidopholus, acorns, *aesculus, agaricus*, agave, agrimonia, algae, aloe, citrus, *brassica*, cinnamon, orange, apple, blueberry, cranberry, peach, pear, lemon, lime, pea, seaweed, green tea, chamomile, willowbark, mulberry, poppy, and the like. Further botanical extracts include one or more essential oils, including one or more of: Bergamot—*Citrus Aurantium Bergamia* (Bergamot) Fruit Oil, Coconut—*Cocos Nucifera* (Coconut) Oil, Basil—*Ocimum Basilicum* (Basil) Oil, Tangerine—*Citrus Nobilis* (Mandarin Orange) Peel Oil, Geranium—*Pelargonium Graveolens* Flower Oil, Jasmine—*Jasminum Officinale* (Jasmine) Oil, Lavender—*Lavandula Angustifolis* (Lavender) Oil, Lemon—*Citrus Medica Limonum* (Lemon) Peel Oil, Lime—*Citrus Aurantium Dulcis* (Orange) Peel Oil, Clove—*Eugenia Caryophyllus* (Clove) Leaf Oil, Spearmint—*Mentha Viridis* (Spearmint) Leaf Oil, Vanilla—*Vanilla Planifolia* Fruit Extract, Patchouly—*Pogostemon Cablin* Oil, Curry Leaf—*Murraya Koenigii* (Curry) Leaf Oil, Cinnamon Leaf—*Cinnamomum Cassia* Leaf Oil, Chamomile—*Anthemis Nobilis* Flower Oil, Orange—*Citrus Aurantium Dulcis* (Orange) Peel Oil, Clary Sage—*Salvia Sclarea* (Clary) Oil, Tea Tree—*Melaleuca Alternifolia* (Tea Tree) Leaf Oil. Further botanical extracts include terpenes, terpene alcohols, sesquiterpene alcohols, terpinen-4-ol, bisabolol, farnesol, anise oils, neroli, sandalwood, geraniol, neral, citronellal, cinnamaldehyde, lemongrass oil, linalool, eugenol, carvacrol, thymol, and cinnamaldehyde. When present, such botanical extracts may be present in any effective amount but advantageously are present in an amount of at least about 0.001% wt., preferably from about 0.01% wt.-7.5% wt. based on the total weight of the animate surface treatment composition of which it forms a part.

A further optional constituent of the treatment compositions of the invention are one or more colorants, such as dyes and pigments which may be used to impart a color to the compositions of which they form a part. As colorants may be used organic pigments, such as one or more of red, green, blue, yellow, violet, orange pigments. Lakes of such pigments, viz, wherein the organic pigments are reacted with a metal salt such as calcium, aluminum, barium, zirconium, and the like to form salts. Formation of the metal salt of the organic pigment will generally convert the pigment from a water soluble pigment into a water insoluble pigment. Examples of organic pigment families that may be used herein include azo, (including monoazo and diazo), fluoran, xanthene, indigoid, triphenylmethane, anthroquinone, pyrene, pyrazole, quinoline, quinoline, or metallic salts thereof may also be used. Particularly useful are D&C colors, FD&C colors, or Lakes of D&C or FD&C colors. The term "D&C" means drug and cosmetic colors that are approved for use in drugs and cosmetics by the FDA. The term "FD&C" means food, drug, and cosmetic colors which are approved for use in foods, drugs, and cosmetics by the U.S. Food and Drug Administration. Such include FD&C colors: Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and the like. As colorants may also be used inorganic pigments, including but not limited to iron oxides such as red, blue, black, green, and yellow; titanium dioxide, bismuth oxychloride, and the like. When present, such colorants may be included in any effective amount, preferably from about 0.00001% wt.-2.5% wt., based on the total weight of the inventive composition of which they form a part.

The animate treatment compositions of the invention optionally may include one or more particulate fillers, which may in some instances also function as an abrasive agent when topically applied. By way of non-limiting example, such include powders such as titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, zinc laurate, zinc myristate, zinc rosinate, alumina, attapulgite, calcium carbonate, calcium silicate, dextran, kaolin, nylon, silica sylylate, sericite, soy flour, tin oxide, titanium hydroxide, trimagnesium phosphate, walnut shell powder, or mixtures thereof. Also useful and in certain embodiments preferred, are titanium dioxide, and zinc oxide. The above mentioned powders may be surface treated with lecithin, amino acids, mineral oil, silicone oil or various other agents either alone or in combination, which coat the powder surface and render the particles more lipophilic in nature. The average particle size of the particulate fillers may vary widely and indeed a broad distribution of average particle sizes may be preferred for use, or alternatively a narrow distribution of average particle size may be preferred. In certain applications, one or more of the particulate fillers may also function as a physical sunblock material which may block the absorption of UVA and/or UVB radiation by topical surfaces treated by the compositions of the invention.

Advantageously the average particle size of the particulate fillers is in the range of about 0.01 to 1000 microns, preferably from about 0.1 to about 250 microns. When present in the animate treatment compositions of the invention, one or more such particulate fillers comprise from about 0.001% wt.-10% wt., preferably from about 0.01% wt.-5% wt., based on the total weight of the animate surface treatment composition of which the one or more particulate fillers form a part.

The treatment compositions of the invention may also optionally include a preservative constituent which is used to control undesired microorganisms within the treatment composition particularly when the treatment composition is in long-term storage and at elevated temperatures. While these are normally not present due to the microbicidal efficacy of the compositions as taught herein, such ancillary preservative constituents may be included in minor but effective amounts. Nonlimiting examples include one or more of parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. Further exemplary useful preservatives include those which are commercially including a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.). When present, the preservative constituent may be included in any effective amount but preferably forms at least about 0.0001% wt. of the inventive composition of which it forms a part.

The treatment compositions may include one or more thickener components in order to impart a desired viscosity. Non-limiting examples of useful thickener constituents include polysaccharide polymers selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, naturally occurring polysaccharide polymers such as xanthan gum, guar gum, locust bean gum, tragacanth gum, or derivatives thereof, polycarboxylate polymers, polyacrylamides, clays, and mixtures thereof.

The thickener constituent may be one or more cellulose derivatives include methyl cellulose ethyl cellulose, hydroxymethyl cellulose hydroxy ethyl cellulose, hydroxy propyl cellulose, carboxy methyl cellulose, carboxy methyl hydroxyethyl cellulose, hydroxypropyl cellulose, hydroxy propyl methyl cellulose, ethylhydroxymethyl cellulose and ethyl hydroxy ethyl cellulose.

The thickener constituent may be one or more polycarboxylate polymers thickeners which have a molecular weight from about 500,000 to about 4,000,000, preferably from about 1,000,000 to about 4,000,000, with, preferably, from about 0.5% to about 4% crosslinking Preferred polycarboxylate polymers include polyacrylate polymers including those sold under trade names Carbopol®, Acrysol® ICS-1 and Sokalan®. The preferred polymers are polyacrylates. Other monomers besides acrylic acid can be used to form these polymers including such monomers as ethylene and propylene which act as diluents, and maleic anhydride which acts as a source of additional carboxylic groups.

The thickener constituent may be one or more polycarboxylate polymer which can be a non-associative thickener or stabilizer, such as a homopolymer or a copolymer of an olefinically unsaturated carboxylic acid or anhydride monomers containing at least one activated carbon to carbon olefinic double bond and at least one carboxyl group or an alkali soluble acrylic emulsion, or an associative thickener or stabilizer, such as a hydrophobically modified alkali soluble acrylic emulsion or a hydrophobically modified nonionic polyol polymer, i.e., a hydrophobically modified urethane polymer, or combinations thereof. The copolymers are preferably of a polycarboxylic acid monomer and a hydrophobic monomer. The preferred carboxylic acid is acrylic acid. The homopolymers and copolymers preferably are crosslinked. Homopolymers of polyacrylic acid are described, for example, in U.S. Pat. No. 2,798,053. Examples of homopolymers which are useful include Carbopol® 934, 940, 941, Ultrez 10, ETD 2050, and 974P polymers, which are available from Noveon. Such polymers are homopolymers of unsaturated, polymerizable carboxylic monomers such as acrylic acid, methacrylic acid, maleic acid, itaconic acid, maleic anhydride, and the like.

The thickener constituent may be one or more hydrophobically modified polyacrylic acid polymers including those are described, for example, in U.S. Pat. Nos. 3,915,921, 4,421,902, 4,509,49, 4,923,940, 4,996,274, 5,004,598, and 5,349,030. These polymers have a large water-loving hydrophilic portion (the polyacrylic acid portion) and a smaller oil-loving hydrophobic portion (which can be derived from a long carbon chain acrylate ester). Representative higher alkyl acrylic esters are decycl acrylate, lauryl acrylate, stearyl acrylate, behenyl acrylate and melissyl acrylate, and the corresponding methacrylates. It should be understood that more than one carboxylic monomer and more than one acrylate ester or vinyl ester or ether or styrenic can be used in the monomer charge. The polymers can be dispersed in water and neutralized with base to thicken the aqueous composition, form a gel, or emulsify or suspend a deliverable. Useful polymers are sold as Carbopol® 1342 and 1382 and Pemulen® TR-1, TR-2, 1621, and 1622, all available from Noveon. The carboxyl containing polymers are prepared from monomers containing at least one activated vinyl group and a carboxyl group, and would include copolymers of polymerizable carboxylic monomers with acrylate esters, acrylamides, alkylated acrylamides, olefins, vinyl esters, vinyl ethers, or styrenics. The carboxyl containing polymers have molecular weights greater than about 500 to as high as several billion, or more, usually greater than about 10,000 to 900,000 or more.

Also useful as thickeners are interpolymers of hydrophobically modified monomers and steric stabilizing polymeric surface active agents having at least one hydrophilic moiety and at least one hydrophobic moiety or a linear block or random comb configuration or mixtures thereof. Examples of steric stabilizers which can be used are Hypermer®, which is a poly(12-hydroxystearic acid) polymer, available from Imperial Chemical Industries Inc. and Pecosil®, which is a methyl-3-polyethoxypropyl siloxane-ω-phosphate polymer, available from Phoenix Chemical, Somerville, N.J. These are taught by U.S. Pat. Nos. 4,203,877 and 5,349,030, the disclosures of which are incorporated herein by reference.

The polymers can be crosslinked in a manner known in the art by including, in the monomer charge, a suitable crosslinker in amount of about 0.1 to 4%, preferably 0.2 to 1% by weight based on the combined weight of the carboxylic monomer and the comonomer(s). The crosslinker is selected from polymerizable monomers which contain a polymerizable vinyl group and at least one other polymerizable group. Polymerization of the carboxyl-containing monomers is usually carried out in a catalyzed, free radical polymerization process, usually in inert diluents, as is known in the art.

Other polycarboxylic acid polymer compositions which can be used in the thickener constituent include, for example, crosslinked copolymers of acrylates, (meth)acrylic acid, maleic anhydride, and various combinations thereof. Commercial polymers are available from Rheox Inc., Highstown, N.J. (such as Rheolate® 5000 polymer), 3 V Sigma, Bergamo, Italy (such as Stabelyn® 30 polymer, which is an acrylic acid/vinyl ester copolymer, or Polygel® and Synthalen® polymers, which are crosslinked acrylic acid polymers and copolymers), Noveon (such as Carbopol 674 (lightly crosslinked polyacrylate polymer), Carbopol 676 (highly crosslinked polyacrylate polymer), Carbopol EP-1 thickener, which is a acrylic emulsion thickener), or Rohm and Haas (such as Acrysol® ICS-1 and Aculyn® 22 thickeners, which are hydrophobically modified alkali-soluble acrylic polymer emulsions and Aculyn® 44 thickener, which is a hydrophobically modified nonionic polyol). Preferred are the Carbopol® and Pemulen® polymers, generally. Further useful are crosslinked, alkali swellable, associative polymer thickeners comprising acidic monomers and associative monomers with hydrophobic end groups, whereby the polymer comprises a percentage of hydrophobic modification and at least one hydrophobic side chain comprising an alkyl function group, including commercial polymers sold as Aqupec® SER-300 described to be an acrylates/C10-C30 alkyl acrylate crosspolymer which comprises stearyl side chains and is less than 1% of hydrophobic modification of the polymer, and Aqupec® HV-701EDR described as being an acrylates/C10-C30 alkyl acrylate crosspolymer which comprises octyl side chains and about 3.5% of hydrophobic modification of the polymer (although such and similar polymers which comprise stearyl, octyl, decyl and/or lauryl side chains are also considered to be suitable as well), both available from Sumitomo Seika of Japan. The choice of the specific polymer to be employed will depend upon the desired rheology of the composition, and the identity of other compositional ingredients.

Further useful in the thickener constituent are clay thickeners which comprise, for example, colloid-forming clays, for example, such as smectite and/or attapulgite types. The clay materials can be described as expandable layered clays, i.e., aluminosilicates and magnesium silicates. The term "expandable" as used to describe the instant clays relates to the ability of the layered clay structure to be swollen, or expanded, on contact with water. The expandable clays used herein are those materials classified geologically as smectites (or montmorillonite) and attapulgites (or polygorskites). Smectites are three-layered clays. There are two distinct classes of smectite-type clays. In the first, aluminum oxide is present in the silicate crystal lattice; in the second class of smectites, magnesium oxide is present in the silicate crystal lattice. The general formulas of these smectites are $Al_2(Si_2O_5)_2(OH)_2$ and $Mg_3(Si_2O_5)(OH)_2$, for the aluminum and magnesium oxide type clays, respectively. It is to be recognized that the range of the water of hydration in the above formulas may vary with the processing to which the clay has been subjected.

Commercially available clays include, for example, montmorillonite, bentonite, volchonskoite, nontronite, beidellite, hectorite, saponite, sauconite and vermiculite. The clays herein are available under various trade names such as Gelwhite GP, Gelwhite H, Mineral Colloid BP, and Laponite from Southern Clay Products, Inc., Texas; and Van Gel 0 from R. T. Vanderbilt. A second type of expandable clay material useful in the instant invention is classified geologically as attapulgite (polygorskite). Attapulgite clays are commercially available. For example, such clays are marketed under the tradename Attagel, i.e. Attagel 40, Attagel 50 and Attagel 150 from Engelhard Minerals & Chemicals Corporation.

It is of course to be understood that two or more of the foregoing thickeners may be used to form the thickener constituent.

Certain preferred thickeners are disclosed with reference to one or more of the Examples.

Advantageously the thickener constituent may be used to adjust the viscosity of the treatment compositions to a desired viscosity range or to a target viscosity, and the specific amount of the thickener constituent required to achieve said viscosity range or target viscosity may vary based on the other constituents present in the treatment compositions. However, the selection of one or more suitable thickening agents and the necessary amounts may be determined by routine analytical methods by a skilled artisan. Where present, the thickener constituent is present in sufficient amounts to attain such viscosities. Advantageously the thickener constituent forms from about 0.0001% wt.-5% wt., preferably about 0.01-5% wt. of a treatment composition of which it forms a part.

In certain preferred embodiments however, a thickener constituent is excluded.

The pH of the treatment compositions is preferably established and thereafter maintained at a desired pH or within a bounded pH range. As is better understood from a consideration of the example compositions, the inventors have also found that the pH of the treatment compositions plays a significant role in establishing the overall efficacy of a treatment composition in reducing, deactivating or destroying undesired microorganisms, and the preferred pH of an animate surface treatment composition depends in no small degree if Cu(I) and/or Cu(II) ions, or if Zn(I) and/or Zn(II) ions were present in the composition. It was generally, observed that compositions having a higher, more alkaline pH but concurrently including lesser amounts of alcohol (specifically ethanol) provided similar microbicidal performance to other compositions having a lower pH but which included increased amounts of ethanol. Thus, a reasonable degree of flexibility in formulating compositions of the invention is provided by judicious control of the pH and the amount of the lower alkyl monohydric alcohol present. Specific reference is made to the example formulations described hereinafter which demonstrate this effect.

Although the compositions of the invention find use in the pH range of 1-14, and preferably are in the range of 2-11, depending upon the nature or identity of the metal ions present, certain pH ranges are preferred whether Cu(I)

and/or Cu(II) ions, or if Zn(I) and/or Zn(II) ions were present in the compositions. Preferably when zinc ions are present, the pH of the inventive compositions is at least about 5, but is preferably greater and in certain particularly preferred embodiments is substantially alkaline, viz. at least about 7.5 Thus, in preferred embodiments wherein Zn(I) and/or Zn(II) ions were present the pH of the treatment compositions (and/or microbicidal control system) is at least 5, and in order of increasing preference is at least 5.1, 5.2, 5.3, 5.4, 5.5, 5.6, 5.7, 5.8, 5.9, 6, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, and about 12. However in preferred embodiments wherein Cu(I) and/or Cu(II) ions are present, the pH of the inventive compositions is not more than about 10, and is preferably substantially acidic. Thus in these preferred embodiments wherein Cu(I) and/or Cu(II) ions are present, the pH of the treatment compositions (and/or microbicidal control systems) is not more than 9, and in order of increasing preference the pH is not in excess of 10, 9.5, 9, 8.9, 8 . . . , 8.7, 8.6, 8.5, 8.4, 8.3, 8.2, 8.1, 8, 7.9, 7.8, 7.7, 7.6, 7.5, 7.4, 7.3, 7.2, 7.1, 7, 6.9, 6.8, 6.7, 6.6, 6.5, 6.4, 6.3, 6.2, 6.1, 6, 5.9, 5.8, 5.7, 5.6, 5.5, 5.4, 5.3, 5.2, 5.1, 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1 and 3.0.

Particularly preferred pHs are indicated in the foregoing ranges and are demonstrated by the Examples. The pH of the surface treatment compositions may be established, adjusted and/or maintained by the addition of an effective amount of a pH adjustment constituent.

Optionally but preferably the treatment compositions of the invention include a pH adjusting constituent which may be used to establish and/or maintain, viz., buffer, a treatment composition at a desired pH or within a bounded pH range. Essentially any material which may increase or decrease the pH of the treatment composition is suitable as a pH adjusting constituent. Suitable pH adjusting constituents are one or more acids and/or bases whether such be based on organic and/or inorganic compounds or materials. By way of non-limiting example, pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which however are typically required in only minor amounts. By way of further non-limiting example, pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, and hydroxides, can also function as buffers. It may also be suitable to use as buffers such materials as aluminosilicates (zeolites), borates, aluminates and certain organic materials such as gluconates, succinates, maleates, citrates, and their alkali metal salts. Particularly useful and preferred is citric acid and metal salts thereof such as sodium citrate which are widely available and which are effective in providing these pH adjustment and buffering effects. Further exemplary and useful pH adjusting constituents include monoalkanolamines, dialkanolamines, trialkanolamines, and alkylalkanolamines such as alkyl-dialkanolamines, and dialkyl-monoalkanolamines. Such may also function as detersive surfactants. The alkanol and alkyl groups are generally short to medium chain length, that is, from 1 to 7 carbons in length. For di- and trialkanolamines and dialkyl-monoalkanolamines, these groups can be combined on the same amine to produce for example, methylethylhydroxypropylhydroxylamine. One of ordinary skill in the art can readily ascertain other members of this group. Preferred alkanolamines include monoethanolamine.

When present, the one or more pH adjusting constituents are included in amounts which are effective in establishing and/or maintaining the pH of a treatment composition at the desired pH value or within a range of pH values. Advantageously the one or more pH adjusting constituents comprise from about 0.001-2.5% wt., preferably from about 0.01-2% wt. of the treatment composition of which the one or more pH adjusting constituents form a part. Preferred pH adjusting constituents include those demonstrated in or more of the Examples. In certain preferred embodiments, one or more pH adjusting constituents are necessarily present and are to be understood as essential constituents of the treatment compositions.

The animate surface treatment compositions of the invention may include one or more acids, which include not only organic and inorganic acids but also acid salts of organic acids. Preferred examples of the organic acid to be used in the present invention include linear aliphatic acids such as formic acid, acetic acid, propionic acid, butyric acid and valeric acid; dicarboxylic acids such as oxalic acid, malonic acid, succinic acid, glutaric acid, adipic acid, pimelic acid, fumaric acid and maleic acid; acidic amino acids such as glutamic acid and aspartic acid; and hydroxy acids such as glycolic acid, lactic acid, hydroxyacrylic acid, alpha-hydroxybutyric acid, glyceric acid, tartronic acid, malic acid, tartaric acid and citric acid, as well as acid salts of these organic acids. Exemplary inorganic acids include phosphoric acid, potassium dihydrogenphosphate, sodium dihydrogenphosphate, sodium sulfite, potassium sulfite, sodium pyrosulfite (sodium metabisulfite), potassium pyrosulfite (potassium metabisulfite), acid sodium hexametaphosphate, acid potassium hexametaphosphate, acid sodium pyrophosphate, acid potassium pyrophosphate and sulfamic acid. These acids can be used singly or as a mixture of two or more inorganic and/or organic acids. Such one or more acids may be used to adjust the pH of the inventive compositions, and/or buffer the pH of the treatment compositions. When present, these may be included in effective amounts in order to provide the desired technical effect. Advantageously the acids may be present in amounts of from about 0.01-5% wt.

The animate surface treatment compositions of the invention may include an antimicrobially effective amount of an organic acid. Exemplary organic acids are those which generally include at least one carbon atom, and include at least one carboxyl group (—COOH) in its structure and which provide an antimicrobial benefit to the skin treatment compositions and/or the cleaning wipe articles. Derivatives of said organic acids are also contemplated to be useful. Of course mixtures of one or more acids are contemplated as being useful. Exemplary organic acid include linear aliphatic acids such as acetic acid; dicarboxylic acids, acidic amino acids, and hydroxy acids such as glycolic acid, lactic acid, hydroxyacrylic acid, alpha-hydroxybutyric acid, glyceric acid, malic acid, tartaric acid and citric acid, as well as acid salts of these organic acids. Of these, citric acid, sorbic acid, acetic acid, boric acid, formic acid, maleic acid, adipic acid, lactic acid, malic acid, malonic acid, glycolic acid, salicylic acid and/or derivatives thereof, e.g., salicylic acid derivatives such as esters of salicylic acid, such as ethylhexyl salicylate, dipropylene glycol salicylate, TEA salicylate, salicylic acid 2-ethylhexylester, salicylic acid 4-isopropyl benzylester, salicylic acid homomenthylester are preferred. Preferred antimicrobially effective organic acids include lactic acid, salicylic acid and citric acid and/or derivatives thereof; particularly preferred of these are salicylic acid as well as salicylic acid and salicylate esters, including octyl, amyl, phenyl, benzyl, menthyl, glyceryl, and dipropyleneglycol esters. When present, these may be included in effective amounts in order to provide the desired technical effect. Advantageously one or more of such antimicrobially effective organic acids may be present in amounts of from about 0.01-5% wt. The specific identity of preferred antimicrobially effective organic acids and preferred weights and/or weight ranges thereof are described with reference to one or more of the following examples.

A further optional constituent in the inventive treatment compositions is one or more chelating agents. Exemplary useful chelating agents include those known to the art, including by way of non-limiting example; aminopolycarboxylic acids and salts thereof wherein the amino nitrogen has attached thereto two or more substituent groups. Preferred chelating agents include acids and salts, especially the sodium and potassium salts of ethylenediaminetetraacetic acid, diethylenetriaminepentaacetic acid, N-hydroxyethylethylenediaminetriacetic acid, and of which the sodium salts of ethylenediaminetetraacetic acid may be particularly advantageously used. Such chelating agents may be omitted, or they may be included in generally minor amounts such as from about 0.001-0.5% wt. based on the weight of the chelating agents and/or salt forms thereof. When present, advantageously, such chelating agents are included in the present inventive composition in amounts from about 0.001-5% wt., but are most desirably present in reduced weight percentages from about 0.01-0.5% wt.

The amounts or presence of chelating agents should be carefully controlled and may in some preferred embodiments be excluded from the treatment compositions. This is due the fact that the presence of chelating agents may undesirably form insoluble complexes with the Cu(I) and/or Cu(II) ions, or with the Zn(I) and/or Zn(II) ions present in the compositions, and thus reduce or remove their beneficial effects in the treatment compositions. Desirably when such are present they are included in only limited amounts so as not to deleteriously affect the improved microbicidal efficacy of the inventive compositions, but in particularly preferred embodiments such chelating agents are desirably excluded from the compositions of the invention.

When the animate surface treatment compositions (or systems) are provided in a pressurized canister, e.g, an aerosol canister, a propellant is also necessarily present. The propellant may be material or composition which is conventionally used in the art for such purposes. Propellants which may be used include, for example, a hydrocarbon, of from 1 to 10 carbon atoms, such as n-propane, n-butane, isobutane, n-pentane, isopentane, and mixtures thereof dimethyl ether and blends thereof as well as individual or mixtures of chloro-, chlorofluoro- and/or fluorohydrocarbons- and/or hydrochlorofluorocarbons (HCFCs). Useful commercially available compositions include A-70 (Aerosol compositions with a vapor pressure of 70 psig available from companies such as Diversified and Aeropress) and Dymel® 152a (1,1-difluoroethane from DuPont). Compressed gases such as carbon dioxide, compressed air, nitrogen, and possibly dense or supercritical fluids may also be used, and in view of environmental benefits may be preferred for use in many applications wherein the use of hydrocarbon based, and particularly wherein the use of chloro-, chlorofluoro- and/or fluorohydrocarbons- and/or hydrochlorofluorocarbons (HCFCs) are desirably avoided. Individual materials, or blends of materials may be used as the propellant constituent. Advantageously the propellant will generally be present in an amount of from about 1% wt. to about 50% wt. of the total formulation as contained within the aerosol canister, with preferred amounts being from about 1% wt. to about 25% wt., more preferably from about 1% wt. to about 15% wt.

When one or more such further optional constituents are present in the treatment compositions, preferably their cumulative amount does not exceed about 90% wt. and preferably does not exceed about 75% wt., of the treatment composition of which they form a part.

The inventive compositions may be solid including in the form of a compressed bar, cake or tablet, or in the form of comminuted solid particles such as flakes, prills or particulates, a viscous gel or paste, an unpressurized free-flowing liquid, or may be a supplied as an unpressurized sprayable liquid, or as an aerosolized liquid.

When the inventive compositions are unpressurized free-flowing liquids, such liquids preferably have a viscosity in the range of about 200 centipoise ("cP") or less, preferably and in order of increasing preference, viscosities of 150 cP, 100 cP, 75 cP, 50 cP, 25 cP, 20 cP, 15 cP, 10 cP, 5 cP, 3 cP, 2 cP, and 1 cP, when measured using conventional quantitative method, e.g., as measured at 20° C. or 25° C. by a Brookfield Type LVT or Type RVT viscometer using a standard spindle provided by that manufacturer and measuring the samples at room temperature (20-25° C.). Such unpressurized free-flowing liquids are pourable and pumpable and may be dispensed by pumping the composition through a manually operated or a power driven (e.g., motor driven, pressure driven) dispensing device, such as a sprayer, viz "trigger" sprayer or spray pump affixed to a container containing a quantity of the surface treatment composition. The animate surface treatment composition may also be a composition which may be dispensed from the open end of a suitable flask, bottle or other container, or may be dispensed via a suitable nozzle or spout, e.g., which may be operated by either inversion of the container, and optionally compressing some or part of the container, so to expel it from the container to an animate surface to be treated, e.g., hands, or hair. Between such dispensing operations; however, the contents of such a container which includes the treatment composition are not pressurized. The animate surface treatment composition may also be stored within and be dispensable from a wide mounted jar or other container, particularly when such is in a paste, cream or gel form.

The animate surface treatment compositions of the invention may also be supplied within a water dispersible, water miscible or water soluble sachet or pouch or water-soluble package; such may be formed from a water soluble material, such as a water soluble or water dispersible polymeric film (e.g. polyvinyl alcohol), or alternately may be formed from a water insoluble material, such as a water insoluble polymeric film. Additionally the sachet, pouch or package may be formed in a manner where only part of the sachet is physically breachable or only part of the sachet, pouch or package is water soluble or dispersible. Thus a further aspect of the invention provides a closed, a water dispersible, a water miscible or a water soluble sachet or pouch containing the inventive composition as described herein.

The animate surface treatment compositions can also be applied to a dermal and/or keratinous surface by using an inanimate substrate, such as a wipe, sponge or other substrate upon which a quantity or the animate surface treatment composition can be absorbed and/or adsorbed. A suitable wipe can be of a woven or non-woven nature. Fabric substrates can include nonwoven or woven pouches, sponges, or in the form of abrasive or non-abrasive cleaning pads. Such fabrics are known commercially in this field and are often referred to as wipes. Such substrates can be resin bonded, hydroentangled, thermally bonded, meltblown, needlepunched or any combination of the former. The nonwoven fabrics may be a combination of wood pulp fibers and textile length synthetic fibers formed by well known dry-form or wet-lay processes. Synthetic fibers such as rayon, nylon, orlon and polyester as well as blends thereof can be employed. The substrate of the wipe may also be a film forming material such as a water soluble polymer. Such self-supporting film substrates may be sandwiched between layers of fabric substrates and heat sealed to form a useful substrate. The free standing films can be extruded utilizing standard equipment to devolatilize the blend. Casting technology can be used to form and dry films, or a liquid blend can be saturated into a carrier and then dried in a variety of known methods.

The treatment compositions of the present invention are absorbed onto the wipe to form a saturated wipe and sold as a vendible product. The wipe can then be sealed individually in a pouch which can then be opened when needed or a multitude of wipes can be placed in a container for use on an as-needed basis. The container, when closed, is sufficiently sealed to prevent evaporation of any components from the compositions. Thus a further aspect of the invention provides a closed container containing one or more wipes which include the treatment composition as described herein.

The animate surface treatment compositions of the present invention may also be adsorbed and/or adsorbed onto a sterile substrate to form a wound dressing or bandage.

The compositions taught herein are advantageously used to treat animate surfaces and in particular embodiments may be provided as a topical skin treatment composition, a skin cleansing composition, a hand sanitizer composition, a skin disinfecting composition, a hand, face or bodywash composition or other form of a personal care composition when topically applied. The animate surface treatment compositions may also be used as or in a hair treatment composition. The compositions may be applied directly to an animate surface, e.g., a topical surface including a dermal surface and/or hair, or alternately the compositions of the invention may be first applied to an inanimate substrate which is then brought into contact with an animate surface, e.g, a wipe, pad, sponge or bandage to which is first applied an animate surface treatment composition as taught herein, and only subsequently is the thus pretreated inanimate substrate contacted with an animate surface, e.g., a topical surface including a dermal surface or hair.

The compositions according to the invention may be used in processes wherein a composition according to any aspect of the invention is applied to a dermal surface, including but not limited to the skin, hair, hands, feet or any part of an animal body, e.g, a human body, or other animal body in order to provide an mycobacterial benefit thereto and further optionally, a detersive benefit thereto. Such compositions may be any of those commonly understood to be provided as personal care products, which by way of non-limiting example include: tablets, bar soaps, powder compositions, salves, creams, balms, lotions, fluid soaps including liquid hand soaps, shampoos, bodywash compositions, rinse compositions, hair shampoos, hair conditioners, gels including self-supporting gels, pastes, sprayable compositions, and pressurized aerosol compositions. The compositions of the invention may also be used in cosmetic compositions, e.g., a cosmetic base, a makeup remover, and the like.

The animate surface treatment compositions (or systems) according to any aspect of the invention described herein may be ultimately provided in compositions which may be of a variety of forms and product formats. As previously noted, compositions according to any aspect of the invention specifically include solids (e.g., bar soaps, tablets, and the like), readily pourable fluids or liquids (e.g., lotions, hair treatment preparations, bodywash compositions, rinse compositions, and the like) viscous fluids or liquids (e.g., gels, pastes, creams and the like), as well as pumpable or sprayable compositions (e.g. pumpable, non-aerosol compositions such as via a manually operable trigger-spray pump affixed to a container, pressurized compositions, aerosol compositions).

Thus a further aspect of the invention provides a closed container, e.g., a package, containing the inventive composition as described herein which may be in the form of a vendible product.

The treatment compositions of the invention may be used to provide or impart a microbicidal effect on treated animate surfaces, which include keratinous surfaces. Preferably the inventive compositions are characterized in exhibiting a microbicidal benefit when tested against one or more challenge microorganisms according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces, or European Standard Surface Test, EN13697 or AOAC Germicidal Spray Products as Disinfectant Test Method, AOAC Index, $17^{th}$ Ed. (2000), or ASTM E2315-03(2008) Standard Guide for Assessment of Antimicrobial Activity Using a Time-Kill Procedure. In particularly preferred embodiments the treatment compositions exhibit a high degree of microbicidal efficacy against various undesirable microorganisms (sometimes referred to as 'pathogens') including various bacteria, viruses, and fungi. In particularly preferred embodiments treatment compositions of the invention exhibit a high degree of microbicidal efficacy against gram positive bacteria, gram negative bacteria.

As certain embodiments of the invention there are provided processes for the treatment of animate surfaces, which method includes the step of: contacting such a surface which is in need of treatment or upon which the presence of one or more undesirable microorganisms are suspected or are known to be present, with an effective amount of a surface treatment composition as described herein to provide a surface treatment benefit thereto, preferably to provide a microbicidal benefit to the surface, particularly against various undesirable microorganisms (sometimes referred to as 'pathogens') including various bacteria, mycobacteria, viruses, and fungi, and particularly preferably against poliovirus type 1 (Sabin) ("PV1"). Such methods require the application of an effective amount of a treatment composition as taught herein to such surfaces, so that the desired microbicidal benefit is imparted to the treated surface. Desirably such an effective amount is a sufficient amount of a treatment composition which will provide at least a 0.25 $\log_{10}$ reduction, more preferably at least, and in order of increasing preference, a 0.5, 0.75, 1, 1.25, 1.5, 1.75, 2, 2.25, 2.5, 2.75, 3, 3.25, 3.5, 3.75, 4, 4.25, 4.5, 4.75, and 5 $\log_{10}$ reduction against one or more challenge microorganisms, and especially preferably against gram positive bacteria, gram negative bacteria, or other microorganisms or pathogens, e.g., viruses (enveloped and non-enveloped) and/or fungi, in accordance with one or more of the testing protocols described hereinafter, at contact times of 10 minutes or less, preferably, and in order of increasing preference; 9, 8, 7, 6, 5, 4, 3, 2.5, 2, 1.5, 1, and 0.5 minutes contact time, and/or as are demonstrated with reference to one or more of the Examples.

With reference to the Examples described later, and with reference to Tables C and 1, the disclosed compositions were subjected to one or more of the following indicated test protocols in order to evaluate their microbicidal efficacy against one or more of the other challenge microorganisms which are identified on Table B. As is known in the art, amongst the most difficult to control or eradicate are non-enveloped viruses, such as adenovirus and/or poliovirus type 1 (Sabin,) and while microbicidal efficacy against adenovirus and/or poliovirus type 1 (Sabin) presumptively demonstrates that the same composition would be expected to be effective against the bacteria and the other non-enveloped viruses disclosed on Table B, however, the converse is not expected to be true by a skilled artisan. Thus, for example, while a composition which exhibits good microbicidal efficacy against a Gram-positive or Gram-negative bacteria, such would not be expected to be particularly effective against the adenovirus and/or poliovirus type 1 (Sabin), while the converse would be expected to be true.

Preferred treatment compositions of the invention demonstrate a microbicidal benefit when tested according to the standardized protocol outlined in ASTM E1052 Standard Test Method for Efficacy of Antimicrobial Agents against Viruses in Suspension. This test is per se, known to the art. Preferred treatment compositions exhibit a microbicidal benefit against one, but preferably against two or more of the following challenge organisms, specifically "challenge" non-enveloped viruses: hepatitis A (supplied as hepatitis A virus, strain MH-175 ex. Dr. Mark Sobsey, University of North Carolina, Chapel Hill, N.C.; human adenovirus type 5 (supplied as ATCC VR-5); feline calicivirus strain F-9 (supplied as ATCC VR-782); herpes simplex type 1 (supplied as ATCC VR-1493); human rhinovirus type 14 strain 1059 (supplied as ATCC VR-284), and especially preferably against poliovirus type 1 (Sabin) (supplied by U.S. Centers for Disease Control and Prevention (CDC)), in accordance with this test protocol. As is known to the skilled artisan, of these forgoing challenge viruses, the most resistant to control or eradicate is the poliovirus type 1 (Sabin) and is it commonly presumed that any composition which shows an effective degree of control or eradication against the poliovirus type 1 (Sabin) virus will exhibit an even greater degree of control or eradication of the further prior listed viruses. As is known from the literature, e.g., *Hierarchy of susceptibility of viruses to environmental surface disinfectants: a predictor of activity against new and emerging viral pathogens*. J. AOAC International 90:1655-1658, Sattar, S. A. (2007), the efficacy of a composition in controlling or eradicating poliovirus type 1 (Sabin) provides an excellent prediction of the composition's efficacy against further challenge non-enveloped viruses.

Preferred treatment compositions of the invention demonstrate a microbicidal benefit when tested according to the standardized protocol outlined in ASTM E1053 Standard Test Method to Assess Virucidal Activity of Chemicals Intended for Disinfection of Inanimate, Nonporous Environmental Surfaces. This test is also, per se, known to the art. Certain preferred treatment compositions exhibit a microbicidal benefit against gram positive bacteria, gram negative bacteria and preferably against adenovirus and/or poliovirus type 1 (Sabin) (supplied by U.S. Centers for Disease Control and Prevention (CDC)), in accordance with this test protocol. Again, as is known to the skilled artisan, of these forgoing challenge viruses the most resistant to control or eradication is the poliovirus type 1 (Sabin) and is it commonly presumed that any composition which shows an effective degree of control or eradication against the adenovirus and/or poliovirus type 1 (Sabin) will exhibit an even greater degree of control or eradication of many other viruses, including hepatitis A virus, feline calicivirus strain F-9, Herpes simplex type 1 and human rhinovirus type 14 strain 1059 as identified above.

Preferred treatment compositions of the invention demonstrate a microbicidal benefit when tested according to the standardized protocol outlined in European Standard Surface Test, EN13697. This test too is, per se, known to the art. Preferred treatment compositions exhibit a microbicidal benefit against one or more of the following bacteria or fungi: *Staphylococcus aureus* (supplied as ATCC 6538); *Escherichia coli* (supplied as ATCC 10536); *Pseudomonas aeruginosa* (supplied as ATCC 15442); *Enterococcus hirae* (supplied as ATCC 10541) and/or the fungus, *Trichophyton mentagrophytes* (supplied as ATCC 9533) in accordance with the protocols of the test.

Certain preferred treatment compositions of the invention also demonstrate a microbicidal benefit when tested according to the standardized protocol identified as the AOAC Germicidal Spray Products as Disinfectant Test Method, AOAC Index, $17^{th}$ Ed. (2000). This test is also, per se, known to the art. Preferred treatment compositions exhibit a microbicidal benefit against one or more of the following bacteria or fungi: *Staphylococcus aureus* ("*S. aureus*" or "Sa") (supplied as ATCC 6538); *Escherichia coli* ("*E. coli*", or "Ec") (supplied as ATCC 10536), in accordance with the protocols of the test.

Certain of the preferred treatment compositions exhibit an microbicidal benefit when tested according to ASTM E2315-03(2008) Standard Guide for Assessment of Antimicrobial Activity Using a Time-Kill Procedure. Preferred treatment compositions exhibit a microbicidal benefit against one or more of the following bacteria or fungi: *Staphylococcus aureus* ("*S. aureus*" or "Sa"), a gram positive bacteria (supplied as ATCC 6538); *Escherichia coli* ("*E. coli*", or "Ec") a gram negative bacteria (supplied as ATCC 10536), in accordance with the protocols of the test.

The following examples below illustrate exemplary formulations as well as preferred embodiments of the invention. It is to be understood that these examples are provided by way of illustration only and that further useful formulations falling within the scope of the present invention and the claims may be readily produced by one of ordinary skill in the art without deviating from the scope and spirit of the invention.

EXAMPLES

A number of treatment compositions as well as a number of comparative compositions were produced and are described on the following Tables. In these identified compositions, the constituents were used "as supplied" from their respective suppliers and may constitute less than 100% wt. "actives", or may have been supplied as constituting 100% wt. "active" of the named compound, as indicated below. Treatment compositions which are considered to fall within the scope of the present invention are identified by a digit prepended with the letter "E" which indicates this to be an "example" composition, while compositions provided only for the purposes of comparison are identified by a digit prepended with the letter "C", which indicates this to be a comparative composition and falling outside of the scope of the present invention. In certain of the treatment compositions, one or more constituents, e.g., a pH adjusting agent, or deionized water was added in "quantum sufficient" "q.s." in order to provide a desired pH or to provide a sufficient mass in order to provide 100% wt. of each composition. The example compositions disclosed hereinafter include certain presently preferred embodiments of the invention. The comparative compositions are presented on Table C, while treatment compositions of the invention are identified on one or more of the further tables, e.g, Table 1.

The compositions disclosed on the following tables were produced by simple mixing, under stirring, of the identified constituents, generally in accordance with the following protocol. To a suitably sized laboratory beaker outfitted with a mechanical stirrer or a magnetic stirrer, was first supplied a major proportion of the deionized water. All of the constituents, as well as the laboratory beaker were at room temperature (approx. 20° C.) and as the beaker was open, mixing was at normal atmospheric pressure. Thereafter under stirring conditions (approx. 300 rpm) was added the source of copper ions, and mixing continued until this material was dissolved. Subsequently while stirring continued, was next added the quaternary ammonium compound(s), and next any pH adjusting agents when such were included. Stirring continued for a further 15-30 minutes to ensure a homogenous mixture, to which was next added the alcohol constituent. Subsequently were added any remaining constituents including any further quantity of pH adjusting constituents (if present) in order to establish the desired pH of the surface treatment composition. Constituents identified as being added "q.s." were added in order to adjust the pH of the formed composition or to bring the weight of the formed composition to 100% wt. Stirring continued for a further 1-15 minutes to ensure the formation of a homogenous mixture, after which the surface treatment composition was withdrawn from the beaker and used or tested.

Where not indicated as already incorporating an amount of a suitable propellant, it is to be understood that to any of the example compositions described on the following tables may be added a suitable amount of a propellant. Typically an additional 1-10% wt. of a suitable propellant may be added to the 100% wt. of an example composition which can then be placed into a sealed container or vessel, e.g., an aerosol canister provided with a dispensing valve, such as a common nozzle through which the pressurized treatment composition may be dispensed.

TABLE A

| | |
|---|---|
| CuSO4•5H2O | CuSO$_4$•5H$_2$O, technical grade (100% wt. actives) |
| CuCl2•2H2O | CuCl$_2$•2H$_2$O, technical grade (100% wt. actives) |
| Cu(AcO)2•H2O | Cu(AcO)$_2$•H$_2$O, technical grade (100% wt. actives) |
| Cu D-gluconate | Cu D-gluconate, technical grade (100% wt. actives) |
| Cu(I)Cl•H2O | Cu(I)Cl•H$_2$O, technical grade (100% wt. actives) |
| ZnSO4•7H2O (or, zinc sulfate•7H2O) | zinc sulfate heptahydrate (100% wt. actives) |
| zinc citrate•3H$_2$O | zinc citrate•3H$_2$O, powder, 100% actives |
| zinc acetate | zinc acetate, powder, 100% actives |
| zinc chloride | zinc chloride, powder, 100% actives |

TABLE A-continued

| | |
|---|---|
| ethanol (100%) | ethanol, technical grade, (99-100% wt. actives) |
| ethanol (95%) | ethanol, technical grade (99-100% wt. actives), balance, water |
| isopropanol | isopropanol, technical grade, grade (99-100% wt. actives) |
| n-propanol | n-propanol, technical grade, grade (99-100% wt. actives) |
| propylene glycol | propylene glycol, technical grade (99-100% wt. actives) |
| BTC-65 (50%) | $C_{12}$-$C_{16}$ alkyl dimethyl benzyl ammonium chloride provided in an aqueous alcoholic carrier (50% wt. actives) (ex. Stepan) |
| Onyxide 3300 (33%) | quaternary ammonium complex with saccharinate counterion, (33% wt. actives, balance ethanol) (ex. Stepan Co.) |
| MB-50 (50%) | Benalkonium chloride (50% wt actives) supplied as Barquat MB-50 |
| stearalkonium chloride | cationic surfactant (20% wt. actives) supplied as Mackernium 25NA (ex. Rhodia) |
| Neodol 91-6 | nonionic surfactant, $C_9$-$C_{11}$ linear primary alcohol ethoxylate, avg. 6 mols, ethoxylation, 100% wt. actives |
| Crodasol WS | nonionic surfactant based on alcohol alkoxylates, comprising polyethylene glycol monooctyl ether: $CH_3(CH_2)_6CH_2(OCH_2CH_2)_nOH$ where n = 2-8 (100% wt. active) ex. Croda |
| decyl glucoside | nonionic surfactant, (100% wt. actives) supplied as Mackol DG (ex. Rhodia) or Oramix NS (100% wt. actives) (ex. Seppic) |
| Steol CS370 | anionic surfactant, sodium laureth sulfate, 3 mols EO (70% wt. actives) (ex. Stepan Co.) |
| Glucopon 425N | alkylpolyglycoside (50% wt. actives) (ex. Cognis) |
| Plurafac SL62 | nonionic surfactant, linear alcohol ethoxylate (100% wt. active) (ex. BASF) |
| Tween 20 | sorbitan based surfactant |
| Silwet Hydrostable 212 | silylated/organic surfactant blend (used "as supplied") (ex. Momentive Performance Materials, Inc.). |
| sodium lauroyl sarcosinate (30%) | sodium lauroyl sarcsonate, suppled as Crodasinic LC30 (30% wt. active) (ex. Croda) |
| lauramine oxide (30%) | Lauramine oxide, supplied as Ammonyx LO (30% wt. actives) |
| ethanolamine (or, monoethanolamine) | ethanolamine, technical grade (100% wt. active) |
| triethanolamine | triethanolamine, technical grade (100% wt. active) |
| isopropylamine | laboratory grade, (98%-100% wt. active) |
| salicylic acid | laboratory grade, (98%-100% wt. active) |
| PCMX | parachlorometaxylenol, laboratory grade, (98%-100% wt. active) |
| Polyquaternium-7 | copolymer of diallyldimethyl ammonium chloride and acrylamide, (8-9% wt. actives) (MW = 2,000,000) supplied as Mackernium 007 |
| hydroxypropyl cellulose | hydroxypropyl cellulose, supplied as Methocel E4M (100% wt. active) |
| NH4OH (29.6%) | aqueous solution of NH$_4$OH (29.6% wt. active) |
| NaOH (10%) | aqueous solution of sodium hydroxide, 10% wt. active |
| NaOH (50%) | aqueous solution of sodium hydroxide, 50% wt. active |
| Citrosol 502(50%) | aqueous solution of citric acid (50% wt. active) (ex. ADM) |
| Citrosol 502(50%)/6 | aqueous solution of citric acid (50% wt. active) (ex. ADM) further diluted 1:6 in deionized water |
| citric acid (1.56%) | aqueous solution of anhydrous laboratory grade citric acid (1.56% wt. active) |
| citric acid (anhy) | anhydrous citric acid, powder, (100% wt. actives) laboratory grade |
| ammonium acetate | laboratory grade, (98%-100% wt. active) |
| Monacor BE | borate ester blend, used as supplied comprising MEA-borate ester and MIPA-borate ester (ex. Croda, tradename Crodacor BE) |
| IL2976 | corrosion inhibitor comprising mixed acid esters, a proprietary composition believed to be borate esters, used 'as supplied' |

TABLE A-continued

| | |
|---|---|
| morpholine | laboratory grade, (98%-100% wt. active) |
| sodium benzoate | sodium benzoate, powder, 100% actives |
| Neutrol TA | tetrahydroxypropyl ethylenediamine, used as supplied (ex. BASF) |
| fragrance | proprietary composition of its supplier |
| di H$_2$O | deionized water, (100% wt. active) |
| propellant | 21% wt. n-propane and 79% wt. n-butane, supplied as AB46 |

Further, wherein a specific composition was evaluated for microbicidal efficacy against a challenge microorganism according to one or more of the test protocols identified above, the results of these tests are reported as well. Wherein multiple challenge microorganisms were evaluated in any one test, multiple results are reported.

In the following tables, the tested microorganisms and their identity as reported on the tables are as identified on Table B:

TABLE B

| Microorganisms | |
|---|---|
| Identifier | Type/Challenge microorganism |
| "PV1" | Virus/Poliovirus type 1 Sabin, ex. supplied by U.S. Centers for Disease Control and Prevention (CDC) |
| "HAV" | Virus/Hepatitis A virus, strain MH-175 ex. Dr. Mark Sobsey, University of North Carolina, Chapel Hill, NC |
| "HAdV" | Virus/Human adenovirus type 5, supplied as ATCC VR-5 |
| "FCV" | Virus/Feline calicivirus strain F-9, supplied as ATCC VR-782 (The use of the feline calicivirus strain F-9 was as a surrogate virus for Norovirus) |
| "IV-A" | Virus/Influenza A virus, A/California/04/2009 (H1N1), supplied as Biodefence and Emerging Infections Research Resources Repository (BEI Resource) NR-13658Virus/Swine, supplied as |
| "HSV" | Virus/Herpes simplex type 1, supplied as ATCC VR-1493 |
| "HRV" | Virus/Human rhinovirus type 14 strain 1059, supplied as ATCC VR-284 |
| "Rota" | Virus/Rotavirus Wa strain, supplied as ATCC VR-2018 |
| "M. bovis" or "Mb" | Bacteria/Mycobacterium bovis - BCG, supplied by Organon Teknika, Durham, NC to ATS Labsas (used as a surrogate for testing efficacy against Tuberculosis) |
| "S. aureus" or "Sa" | Bacteria/Staphylococcus aureus, supplied as ATCC 6538 |
| "E. coli" or "Ec" | Bacteria/Escherichia coli, supplied as ATCC 10536 |
| "P. aeruginosa" or "Pa" | Bacteria/Pseudomonas aeruginosa ("P. aeruginosa") (supplied as ATCC 15442); |
| "E. hirae", or "Eh" | Bacteria/Enterococcus hirae, supplied as ATCC 10541 |
| "A. niger" | Fungus/Aspergillis niger, supplied as ATCC 16404 |
| "T. mentagropytes" or "T. ment" | Fungus/Trichophyton mentagropytesmetagropytes, supplied as ATCC 9533 |

In the following tables, Table C describes various "comparative" examples, (which may be identified by the prepended letter "C") while subsequent Table 1 describes various examples of compositions according to the invention, (which may also be identified by the prepended letter "E") as well as the observed physical properties and the results of microbidical testing according to one or more of the following standardized test protocols:

A) ASTM E1052-96(2002) Standard Test Method for Efficacy of Antimicrobial Agents against Viruses in Suspension, identified on the following tables as "ASTM E 1052 (log$_{10}$ reduction)" for 5 minutes contact time, unless otherwise specified;

B) ASTM E1053-11 Standard Test Method to Assess Virucidal Activity of Chemicals Intended for Disinfection of Inanimate, Nonporous Environmental Surfaces, identified on the following tables as "ASTM E 1053 (log$_{10}$ reduction) for a 10 minutes contact time, unless otherwise specified;

C) European Standard Surface Test, EN13697, identified on the following tables as "EN 13697 (log 10 reduction) at 5 minutes contact time", D) AOAC Germicidal Spray Products as Disinfectant Test Method, AOAC Index, 17th Ed. (2000), 5 minutes contact time identified on the following tables, unless otherwise specified, as "AOAC Germicidal Spray". In this test, a result of "0/60" or "1/60" is equivalent to a result of "pass" according to that test's protocols. Results of "2" or greater for "/60" are equivalent to a "fail" according to that test's protocols, E) The European Standard Surface Test, EN13697 protocol was used for testing antifungal efficacy against the fungus Trichophyton mentagrophytas (supplied as ATCC 9533); the results reported on the following tables are the log$_{10}$ reduction of the fungus, at 15 minutes contact time, unless otherwise specified;

F) ASTM E2315-03(2008) Standard Guide for Assessment of Antimicrobial Activity Using a Time-Kill Procedure identified on the following tables as "ASTM E 2315 (log 10 reduction)" at 1 minutes contact time, unless otherwise specified.

It is noted that each tested composition was not necessarily tested according to all of the foregoing protocols as test results of microbicidal efficacy against Poliovirus type 1 Sabin supports the presumption of efficacy against easier to control or eradicate microorganisms.

In the following tables the amount of the copper ions present are also indicated in parts per million (ppm) and this number is based on the empirical calculation of the available copper ions present in the indicated composition and 100% disassociation of the copper ion from the copper ion source is presumed for this empirical calculation. A similar calculation may be performed with respect to the amount of available zinc ions in a composition.

All of the compositions of Table 1, 2 and C were liquids which were readily pourable and pumpable and had a "water-thin" viscosity, unless indicated otherwise.

The inventive compositions disclosed on Table 1 were formulated and tested for microbicial efficacy without the addition of a propellant, unless otherwise specified. The inventive compositions disclosed on Table 2 were first combined with the indicated propellant and the expelled pressurized composition (spray) was collected, and subsequently subjected to microbicidal testing.

TABLE C (Comparative Examples)

|  | C1 | C2 | C3 | C4 | C5 | C6 |
|---|---|---|---|---|---|---|
| $CuSO_4 \cdot 5H_2O$ | — | — | 0.1 | 0.1 | — | — |
| ethanol (100%) | — | 45 | — | — | 5 | 10 |
| ethanol (95%) | — | — | — | — | — | — |
| BTC-65 (50%) | 0.2 | 0.2 | — | — | 0.2 | 0.2 |
| Onyxide 3300 (33%) | — | — | — | — | — | — |
| Neodol 91-6 | 0.1 | 0.1 | 0.1 | — | 0.1 | 0.1 |
| Plurafac SL62 | — | — | — | — | — | — |
| triethanolamine | 0.022 | 0.04 | 0.39 | 0.30 | — | — |
| citric acid (1.56%) | — | — | — | — | — | — |
| di $H_2O$ | 99.67 | 54.66 | 99.4 | 99.56 | 94.7 | 89.70 |
| pH | 9 | 9.09 | 8.08 | 8.08 | 8.44 | 8.35 |
| copper ion content (ppm) | 0 | 0 | 254 | 254 | 0 | 0 |
| appearance | colorless | colorless | light blue | medium blue | colorless | colorless |
| ASTM E 1052 (log10 reduction) | PV1 = 3.00<br>IV-A >5.00<br>HSV >6.00<br>HAdV <2.0 | PV1 >2.67<br>PV1 <2.17<br>PV1 <1.52<br>HSV >6.00<br>HAdV >4.5<br>HRV = 3.83 | PV1 = 2.5<br>IV-A >6.00<br>IV-A >5.17<br>HSV >7.5<br>HSV >7.0<br>HAdV <1.0 | PV1 = 1.5<br>IV-A <1.33<br>IV-A <0.33<br>HSV <2.17<br>HAdV <1.73 | PV1 <0.23 | PV1 <0.23 |
| ASTM E 1053 (log10 reduction) | — | — | — | — | — | — |
| AOAC Germicidal Spray | — | — | Sa = 57/60<br>Pa = 27/60 | Sa = 60/60<br>Pa = 23/60 | — | — |
| EN 13697 (log10 reduction) | Sa = 4.31<br>EC >5.50<br>Pa >4.52<br>Eh = 5.48 | — | Sa <1.17<br>Ec = 2.12<br>Pa = 2.84<br>Eh <1.3 | Sa <1.97<br>Ec = 0.44<br>Pa = 0.78 | Sa >6.40<br>Ec >6.58<br>Pa >5.16<br>Eh >6.74 | — |
| T. ment (log10 reduction) | — | — | — | 0.06 | — | — |

|  | C7 | C8 | C9 | C10 | C11 | C12 | C13 |
|---|---|---|---|---|---|---|---|
| $CuSO4 \cdot 5H2O$ | — | — | — | — | — | — | — |
| ethanol (100%) | 50 | 50 | 50 | 35 | 35 | 35 | 35 |
| ethanol (95%) | — | — | — | — | — | — | — |
| BTC-65 (50%) | 0.2 | — | — | — | — | — | — |
| Onyxide 3300 (33%) | — | — | — | — | — | — | — |
| Neodol 91-6 | 0.1 | 0.1 | — | — | — | — | — |
| Plurafac SL62 | — | — | — | — | — | — | — |
| triethanolamine | 0.012 | 0.014 | 0.015 | — | 0.002 | 0.08 | — |
| Citrasol 502 (50%) | — | — | — | 0.30 | 0.02 | 0.016 | 0.016 |
| NH4(OH) (29.86%) | — | — | — | — | — | — | — |
| NaOH (10%) | — | — | — | — | — | — | 0.01 |
| di H2O | 49.68 | 49.89 | 49.985 | 64.7 | 64.98 | 64.9 | 64.8 |
| pH | 8.64 | 8.87 | 8.98 | 3.07 | 5.01 | 9.01 | 11.15 |
| copper ion content (ppm) | 0 | 0 | 0 | 0 | 0 | 0 | 0 |
| appearance | colorless | colorless | — | colorless | colorless | colorless | colorless |
| ASTM E 1052 (log10 reduction) | PV1 <1.25<br>HAdv >4.50<br>HRV >6.00<br>FCV >4.33<br>FCV >6.00 | PV1 = 2.0 | PV1 = 1.5 | PV1 ≤1.77 | PV1 ≤1.67<br>FCV <2.33 | PV1 ≤2.10 | PV <1.67<br>FCV >3.83 |
| ASTM E 1053 (log10 reduction) | — | — | — | — | — | — | — |
| AOAC Germicidal Spray | — | — | — | — | — | — | — |
| EN 13697 (log10 reduction) | Sa >6.12<br>Ec >5.66<br>Pa >3.80<br>Eh >6.50 | — | — | — | — | — | — |
| T. ment (log10 reduction) | >5.74 | — | — | — | — | — | — |

|  | C14 | C15 | C16 | C17 | C18 | C19 | C20 |
|---|---|---|---|---|---|---|---|
| $CuSO_4 \cdot 5H_2O$ | — | — | — | — | — | 46.35 | 46.35 |
| ethanol (100%) | — | — | — | — | — | — | — |
| ethanol (95%) | 40.53 | 40.53 | 46.35 | 52.19 | 52.19 | — | — |
| BTC-65 (50%) | — | — | — | — | — | — | — |
| Onyxide 3300 (33%) | 0.342 | 0.342 | 0.342 | 0.342 | 0.342 | 0.34 | 0.34 |
| Neodol 91-6 | — | — | — | — | — | 0.15 | 0.15 |
| Plurafac SL62 | — | — | — | — | — | — | — |

TABLE C-continued

| | | | | | | | |
|---|---|---|---|---|---|---|---|
| Tween 20 | 0.057 | 0.054 | 0.054 | 0.054 | 0.54 | — | — |
| Silwet Hydrostable 212 | 0.108 | 0.108 | 0.108 | 0.108 | 0.108 | — | — |
| monoethanolamine | — | q.s. | — | — | q.s. | q.s. | q.s. |
| triethanlamine | — | — | — | — | — | 0.1 | 0.2 |
| citric acid (1.56%) | q.s. | — | q.s. | q.s | — | — | — |
| NH4OH (29.86%) | — | — | — | — | — | 0.05 | 0.05 |
| fragrance | 0.25 | 0.25 | 0.25 | 0.25 | 0.25 | 0.25 | 0.25 |
| Monacor BE | 0.269 | 0.269 | 0.269 | 0.269 | 0.269 | — | — |
| di $H_2O$ | 58.45 | 58.45 | 52.63 | 46.79 | 46.79 | 52.76 | 52.66 |
| propellant* | +7% vol. | +7% vol. | +7% vol. | +7% vol. | +7% vol. | — | — |
| pH | 7.5 | 10.5 | 9.0 | 7.5 | 10.5 | 9 | 10.5 |
| copper ion content (ppm) | 0 | 0 | 0 | 0 | 0 | 0 | 0 |
| appearance | colorless | colorless | colorless | colorless | colorless | colorless | colorless |
| ASTM E 1052 (log10 reduction) | — | — | — | — | — | — | — |
| ASTM E 1053 (log10 reduction) | 10 min: PV1 = 1.0 PV1 = 2.0 | 10 min: PV1 = 3.25 PV1 = 2.0 | 10 min: PV1 = 2.25 PV1 = 3.0 | 10 min: PV1 = 0 PV1 = 0 | 10 min: PV1 = 2.25 PV1 = >3.5 | 10 min: PV1 = 2.17 viral titer = 7.50 10 min: HRV = 2.75 HRV >3.25 | 10 min: PV1 = 2.83 viral titer = 7.50 10 min: HRV >3.25 HRV >3.25 |
| AOAC Germicidal Spray | — | — | — | — | — | — | — |
| EN 13697 (log10 reduction) | — | — | — | — | — | — | — |
| *T. ment* (log10 reduction) | — | — | — | — | — | — | — | propellant* - the measured constituents of the liquid composition (which provides 100% wt.) was charged to a pressurizable vessel (e.g., Wheaton bottle, aerosol canister, to which was added 7% by volume of the indicated propellant, and thereafter the vessel was sealed.

| | C21 | C22 | C23 | C24 | C25 | C26 | C27 |
|---|---|---|---|---|---|---|---|
| $CuSO_4 \cdot 5H_2O$ | — | 0.025 | — | — | — | — | — |
| BTC-65 (50%) | 0.015 | — | 0.19 | 0.19 | 0.19 | 0.19 | 0.10 |
| Neodol 91-6 | — | — | 0.6 | 0.6 | 0.6 | 0.6 | 0.6 |
| monoethanolamine | — | — | — | — | — | — | — |
| triethanlamine | — | — | — | — | — | 0.005 | 0.05 |
| Citrosol 502 (50%) | — | — | 0.10 | 0.09 | — | — | — |
| Monacor BE | — | — | 0.026 | 0.047 | 0.423 | — | — |
| di $H_2O$ | 99.985 | 99.975 | 99.08 | 99.07 | 98.78 | 99.2 | 99.29 |
| pH | 6.02 | 5.38 | 5.01 | 8.19 | 11.0 | 8.09 | 8.09 |
| copper ion content (ppm) | — | 63.62 | — | — | — | — | — |
| appearance | colorless | light blue | colorless | colorless | colorless | colorless | colorless |
| ASTM E 1052 (log10 reduction) | — | — | — | — | — | — | — |
| ASTM E 1053 (log10 reduction) | — | — | — | — | — | — | — |
| AOAC Germicidal Spray | — | — | — | — | — | — | — |
| EN 13697 (log10 reduction) | Sa <0.79 Pa = 2.60 | Sa <0.79 Pa = 1.79 | Sa = 2.53 | Sa = 4.99 | Sa >6.37 | Sa = 5.82 Ec = 3.17 Pa = 3.10 Eh = 4.21 | Sa = 2.76 Ec >6.24 Pa = 2.34 Eh = 3.78 |
| *T. ment* (log10 reduction) | — | — | — | — | — | — | — |

| | C28 | C29 | C30 | C31 | C32 | C33 | C34 |
|---|---|---|---|---|---|---|---|
| $CuSO_4 \cdot 5H_2O$ | 0.2 | 0.1 | 0.025 | — | — | — | — |
| BTC-65 (50%) | — | — | — | 0.2 | — | — | — |
| BTC-2125M | — | — | — | — | 0.2 | — | — |
| BTC-1010 | — | — | — | — | — | 0.2 | — |
| Onyxide 3300 (33%) | — | — | — | — | — | — | 0.2 |
| Neodol 91-6 | 0.60 | 0.60 | 0.60 | — | 0.1 | 0.1 | 0.1 |
| monoethanolamine | — | — | — | — | — | — | — |
| triethanlamine | 0.80 | 0.34 | 0.13 | — | — | — | — |
| Citrosol 502 (50%) | — | — | — | — | — | — | — |
| di $H_2O$ | 98.40 | 98.96 | 99.24 | 99.8 | 99.7 | 99.7 | 99.6 |
| pH | 7.99 | 8.10 | 8.02 | 8.58 | 8.4 | 8.84 | 8.61 |
| copper ion content (ppm) | 509 | 254 | 63.6 | — | — | — | — |
| appearance | light blue | light blue | light blue | colorless | colorless | colorless | colorless |
| ASTM E 1052 (log10 reduction) | — | — | — | PV1 ≤1.83 IV-A >5.00 HSV >6.00 HAdV <1.50 | HAdV <2.0 | HAdV <1.17 | HAdV <2.17 |
| ASTM E 1053 (log10 reduction) | — | — | — | — | — | — | — |
| AOAC Germicidal Spray | Sa = 10/10 (fail) Pa = 1/10 | Sa = 10/10 (fail) Pa = 1/10 | Sa = 10/10 (fail) Pa = 1/10 | Sa = 1/60 (pass) Pa = 1/60 (pass) | — | — | — |
| EN 13697 (log10 reduction) | — | — | — | Sa = 4.47 Ec = 4.28 Pa >4.52 Eh = 3.83 | — | — | — |
| *T. ment* (log10 reduction) | — | — | — | 2.73 | — | — | — |

TABLE C-continued

|  | C35 | C36 |
|---|---|---|
| CuSO₄•5H₂O | — | — |
| BTC-65 (50%) | — | — |
| BTC-2125M | — | — |
| BTC-1010 | 0.20 | — |
| Onyxide 3300 (33%) | — | 0.3 |
| Neodol 91-6 | 0.1 | 0.1 |
| monoethanolamine | — | — |
| triethanolamine | — | — |
| Citrosol 502 (50%) | — | — |
| di H₂O | 99.7 | — |
| pH | 8.84 | 8.61 |
| copper ion content (ppm) | — | — |
| appearance | colorless | colorless |
| ASTM E 1052 (log10 reduction) | HAdV <1.17 | HAdV <2.17 |
| ASTM E 1053 (log10 reduction) | — | — |
| AOAC Germicidal Spray | — | — |
| EN 13697 (log10 reduction) | — | — |
| *T. ment* (log10 reduction) | — | — |

|  | C37 | C38 | C39 | C40 | C41 | C42 | C43 | C44 |
|---|---|---|---|---|---|---|---|---|
| CuSO4•5H2O | — | — | — | — | 0.1 | 0.1 | 0.1 | 0.1 |
| ethanol (100%) | 35 | 35 | 35 | — | — | — | — | — |
| ethanol (95%) | — | — | — | — | — | — | — | — |
| BTC-65 (50%) | 0.2 | — | — | 0.2 | — | — | — | — |
| Onyxide 3300 (33%) | — | — | — | — | — | — | — | — |
| Neodol 91-6 | 0.1 | 0.1 | — | — | — | — | — | — |
| triethanolamine | 0.016 | 0.02 | 0.025 | — | — | — | 0.31 | 0.31 |
| Citrasol 502 (50%) | — | — | — | — | 0.04 | — | — | — |
| NH4(OH) (29.86%) | — | — | — | — | — | — | 0.12 | 0.08 |
| NaOH (10%) | — | — | — | — | — | — | — | 0.39 |
| di H2O | 64.68 | 64.88 | 64.97 | 99.8 | 99.86 | 99.90 | 99.49 | 99.1 |
| pH | 8.89 | 9.08 | 9.23 | 8.58 | 3.08 | 5.08 | 9.22 | 10.95 |
| copper ion content (ppm) | 0 | 0 | 0 | 0 | 254 | 254 | 254 | 254 |
| appearance | clear | clear | clear | clear | colorless | colorless | colorless | Colorless |
| ASTM E 1052 (log10 reduction) | PV1 = <2.17 | PV1 = <1.17 | PV1 = <1.83 FCV >6.00 | PV1 = <1.83 IV-A >5.00 HSV >6.00 HAdv <1.5 | PV1 <1.83 | PV1 <1.67 FCV <1.83 | PV1 <1.67 | PV1 <1.42 FCV >3.33 |
| ASTM E 1053 (log10 reduction) | — | — | — | — | — | — | — | — |
| AOAC Germicidal Spray | — | — | — | Sa = 1/60 PA = 1/60 | — | — | — | — |
| EN 13697 (log10 reduction) | Sa >6.35, Ec >5.35, Pa >3.85 | Sa >6.55 Ec >5.50 Pa >4.52 Eh >6.68 | Sa = 4.60, Ec = 4.19, Pa >4.52 Eh >6.68 | Sa = 4.47, Ec = 4.28, Pa = >4.52 Eh = 3.83 | — | — | — | — |
| *T. ment* (log10 reduction) | — | — | 4.84 | 2.73 | — | — | — | — |

|  | C45 | C46 | C47 | C48 | C49 | C50 | C51 |
|---|---|---|---|---|---|---|---|
| CuSO4•5H2O | — | — | — | — | — | — | — |
| ethanol (100%) | 20.0 | — | — | 10 | 10 | 10 | 10 |
| ethanol (95%) | — | — | — | — | — | — | — |
| isobutanol | — | 35.0 | — | — | — | — | — |
| isopropanol | — | — | 35 | — | — | — | — |
| n-propanol | — | — | — | — | — | — | — |
| BTC-65 (50%) | — | — | — | — | — | — | — |
| Onyxide 3300 (33%) | — | — | — | — | — | — | — |
| Neodol 91-6 | — | — | — | — | — | — | — |
| Plurafac SL62 | — | — | — | — | — | — | — |
| triethanolamine | 0.003 | 0.003 | 0.003 | — | — | — | 0.15 |
| Citrasol 502 (50%) | — | — | — | 0.085 | 0.0025 | 0.02 | — |
| NH4(OH) (29.86%) | — | — | — | — | 0.0035 | — | — |
| NaOH (10%) | — | — | — | — | — | — | 0.035 |
| di H2O | 80.0 | 65.0 | 65.0 | 89.9 | 89.99 | 89.98 | 89.98 |
| pH | 8.81 | 8.93 | 8.47 | 3.07 | 5.07 | 9.22 | 11.04 |
| copper ion content (ppm) | — | — | — | — | — | — | — |
| appearance | colorless | light blue, two phases | colorless | colorless | colorless | colorless | colorless |

TABLE C-continued

|  |  |  |  |  |  |  |  |
|---|---|---|---|---|---|---|---|
| ASTM E 1052 (log10 reduction) | PV1 <0.73 | PV1 <0.83 | PV1 <0.56 | PV1 <0.73 | PV1 <0.73 | PV1 <0.90 | PV1 <0.56 |
| ASTM E 1053 (log10 reduction) | — | — | — | — | — | — | — |
| AOAC Germicidal Spray | — | — | — | — | — | — | — |
| EN 13697 (log10 reduction) | Sa <1.02 EC <1.20 Pa = 0.00 Eh <1.36 | — | — | — | — | — | — |
| T. ment (log10 reduction) | <0.22 | — | — | — | — | — | — |

|  | C52 | C53 | C54 | C55 | C56 | C57 |
|---|---|---|---|---|---|---|
| CuSO4•5H2O | — | — | — | 0.099 | — | 0.099 |
| ethanol (100%) | 12 | — | 17.5 | — | — | — |
| ethanol (95%) | — | — | — | — | — | — |
| isobutanol | 12 | — | 17.5 | — | — | — |
| isopropanol | — | — | — | — | — | — |
| n-propanol | 12 | 35 | — | — | — | — |
| propylene glycol n-propyl ether | — | — | — | 50.0 | 50 | — |
| phenol propane glycol ether | — | — | — | — | — | 50 |
| BTC-65 (50%) | — | — | — | — | — | — |
| Onyxide 3300 (33%) | — | — | — | — | — | — |
| Neodol 91-6 | — | — | — | — | — | — |
| Plurafac SL62 | — | — | — | — | — | — |
| triethanolamine | 0.003 | 0.003 | — | 0.40 | 0.003 | 0.40 |
| Citrasol 502 (50%) | — | — | — | — | — | — |
| NH4(OH) (29.86%) | — | — | — | — | — | — |
| NaOH (10%) | — | — | — | — | — | — |
| di H2O | 64.0 | 65.0 | 65.0 | 49.5 | 50 | 49.5 |
| pH | 8.21 | 8.63 | 8.36 | 7.95 | 8.26 | 8.02 |
| copper ion content (ppm) | — | — | — | 254 | — | 254 |
| appearance | colorless | colorless | colorless | light blue | colorless | light blue, two phase |
| ASTM E 1052 (log10 reduction) | PV1 <0.50 | PV1 <0.50 | PV1 = 1.17 | PV1 <0.17 | PV1 <0.17 | PV1 <0.17 |
| ASTM E 1053 (log10 reduction) | — | — | — | — | — | — |
| AOAC Germicidal Spray | — | — | — | — | — | — |
| EN 13697 (log10 reduction) | — | — | — | — | — | — |
| T. ment (log10 reduction) | — | — | — | — | — | — |

|  | C58 | C59 | C60 | C61 | C62 | C63 |
|---|---|---|---|---|---|---|
| CuSO4•5H2O | — | — | — | — | — | — |
| ethanol (100%) | — | — | — | — | — | — |
| ethanol (95%) | — | — | — | — | — | — |
| BTC-65 (50%) | 0.2 | 0.2 | 0.2 | 0.2 | 0.2 | 0.2 |
| Onyxide 3300 (33%) | — | — | — | — | — | — |
| decyl glucoside | 1.0 | 1.0 | — | — | 5.0 | 5.0 |
| stearalkonium chloride | — | — | 1.0 | 1.0 | — | — |
| triethanolamine | — | — | — | — | — | — |
| Citrasol 502 (50%) | — | — | — | — | — | — |
| NH4(OH) (29.86%) | — | — | — | — | — | — |
| NaOH (10%) | — | — | — | — | — | — |
| di H2O | q.s. | q.s. | q.s. | q.s. | q.s. | q.s. |
| pH | 5.1 | 8.14 | 4.77 | 8.00 | 5.26 | 8.27 |
| copper ion content (ppm) | — | — | — | — | — | — |
| appearance | — | — | — | — | — | — |
| ASTM E 2315 (log10 reduction) | Sa >6.43 Ec = 5.13 | Sa >6.43 Ec = 3.54 | Sa >6.49 Ec >6.58 | Sa >6.49 Ec >6.58 | Sa = 1.19 Ec = 2.51 | Sa = 2.43 Ec = 1.77 |
| ASTM E 1052 (log10 reduction) | — | — | — | — | — | — |
| ASTM E 1053 (log10 reduction) | — | — | — | — | — | — |
| AOAC Germicidal Spray | — | — | — | — | — | — |
| EN 13697 (log10 reduction) | — | — | — | — | — | — |
| T. ment (log10 reduction) | — | — | — | — | — | — |

|  | C64 | C65 | C66 | C67 | C68 | C69 | C70 |
|---|---|---|---|---|---|---|---|
| zinc acetate | — | — | — | — | 0.08 | — | — |
| zinc sulfate•7H2O | — | — | — | — | — | 0.08 | 0.08 |
| zinc chloride | — | — | — | — | — | — | — |
| ethanol (100%) | 35.0 | 45.0 | — | — | — | — | — |
| BTC-65 (50%) | — | — | 0.20 | — | — | — | — |
| Onyxide 3300 (33%) | — | — | — | 0.30 | — | — | — |
| Neodol 91-6 | — | — | — | — | — | 0.10 | — |
| monoethanolamine | — | — | — | — | — | 0.06 | 0.07 |

TABLE C-continued

|  | | | | | | | |
|---|---|---|---|---|---|---|---|
| triethanolamine | 0.025 | 0.005 | — | 0.005 | 0.07 | 0.10 | 0.10 |
| sodium citrate•2H$_2$O | — | — | — | — | 0.20 | 0.10 | 0.10 |
| Citrasol 502 (50%) | — | — | — | — | — | 0.05 | 0.08 |
| NH4(OH) (29.86%) | — | — | — | — | 0.05 | — | — |
| NaOH (10%) | — | — | — | — | — | — | — |
| Triton BX | — | — | — | — | — | — | — |
| Monacor BE | — | — | — | — | — | — | — |
| Silwet Hydrostable | — | — | — | — | — | — | — |
| fragrance | — | — | — | — | — | — | — |
| di H$_2$O | q.s. | q.s. | q.s. | q.s. | q.s. | q.s. | q.s. |
| pH | 9.23 | 8.70 | 8.58 | 9.16 | 9.33 | 9.03 | 9.18 |
| zinc ions (ppm) | 0 | 0 | 0 | 0 | 285 | 182 | 182 |
| ASTM E 1052 (log10 reduction) | PV1 ≥1.83 FCV ≥6.00 | PV1 ≥3.17 | PV1 = 1.83 IVA ≥5.00 HSV ≥6.00 HAdV = 1.50 | PV1 = 2.50 | PV1 = 2.17 | PV1 = 2.83 | PV1 = 2.83 |
| ASTM 1053 (log10 reduction) | — | — | — | — | — | — | — |
| AOAC Germicidal Spray | Sa = 60/60 Pa = 0/60 | — | Sa = 1/60 Pa = 1/60 | — | — | — | — |
| EN 13697 (log10 reduction) | Sa = 4.60 Ec = 4.19 Pa ≥4.52 Eh ≥6.68 | — | Sa = 4.47 Ec = 4.28 Pa ≥4.52 Eh = 3.83 | — | — | — | — |
| EN 13697 T. ment (log10 reduction) | A. niger = 0.93 T. ment = 4.84 | — | A. niger = 0.85 T. ment = 2.73 | — | — | — | — |

|  | C71 | C72 | C73 | C74 | C75 | C76 | C77 | C78 | C79 |
|---|---|---|---|---|---|---|---|---|---|
| zinc acetate | — | — | — | — | — | — | — | — | — |
| zinc sulfate•7H2O | — | — | — | — | — | — | — | — | — |
| zinc chloride | — | — | — | — | — | — | — | — | — |
| ethanol (100%) | 20.0 | 20.0 | 35.0 | 45.0 | 45.0 | 45.0 | 45.0 | 55.0 | 70.0 |
| BTC-65 (50%) | — | 0.20 | 0.20 | 0.20 | — | 0.20 | — | 0.20 | — |
| Onyxide 3300 (33%) | 0.30 | — | — | — | 0.303 | — | 0.303 | — | 0.30 |
| Neodol 91-6 | 0.10 | 0.10 | 0.10 | 0.10 | — | 0.10 | — | 0.10 | 0.10 |
| monoethanolamine | 0.05 | 0.05 | — | — | — | — | — | 0.06 | 0.05 |
| triethanolamine | 0.10 | 0.10 | 0.016 | 0.01 | 0.005 | — | 0.03 | 0.10 | 0.10 |
| sodium citrate•2H$_2$O | 0.08 | 0.08 | — | — | — | 0.04 | — | 0.10 | 0.08 |
| Citrasol 502 (50%) | 0.07 | 0.07 | — | — | — | — | — | 0.06 | 0.07 |
| NH4(OH) (29.86%) | — | — | — | — | — | — | — | — | — |
| NaOH (10%) | — | — | — | — | — | — | — | — | — |
| Triton BX | — | — | — | — | — | — | — | — | — |
| Monacor BE | — | — | — | — | — | — | — | — | — |
| Silwet Hydrostable | — | — | — | — | — | — | — | — | — |
| fragrance | — | — | — | — | — | — | — | — | — |
| di H$_2$O | q.s. | q.s. | q.s. | q.s. | q.s. | q.s. | q.s. | q.s. | q.s. |
| pH | 9.05 | 9.05 | 8.89 | 7.99 | 8.03 | 8.78 | 8.9 | 9.03 | 9.14 |
| zinc ions (ppm) | 0 | 0 | 0 | 0 | 0 | 0 | 0 | 0 | 0 |
| ASTM E 1052 (log10 reduction) | PV1 = 2.83 | PV1 = 2.83 | PV1 = 2.17 | PV1 = 2.00 | PV1 = 2.00 | PV1 = 3.00 | PV1 = 2.27 | PV1 = 4.00 | PV1 = 5.83 |
| ASTM 1053 (log10 reduction) | — | — | — | — | — | — | — | — | — |
| AOAC Germicidal Spray | — | — | — | — | — | — | — | — | — |
| EN 13697 (log10 reduction) | — | — | Sa ≥6.35 Ec ≥5.35 Pa ≥3.85 | — | — | — | Sa ≥6.75 Ec ≥6.06 Pa ≥5.41 Eh ≥6.66 | — | — |
| EN 13697 T. ment (log10 reduction) | — | — | A. niger = 1.86 | — | — | — | ≥4.61 | — | — |

|  | C80 | C81 |
|---|---|---|
| zinc acetate | — | — |
| zinc sulfate•7H2O | — | — |
| zinc chloride | — | — |
| ethanol (100%) | 37.20 | 39.06 |
| BTC-65 (50%) | — | — |
| Onyxide 3300 (33%) | 0.30 | 0.30 |
| Neodol 91-6 | 0.093 | 0.093 |
| monoethanolamine | 0.223 | 0.707 |
| triethanolamine | 0.093 | 0.093 |
| sodium citrate•2H$_2$O | — | — |
| Citrasol 502 (50%) | 0.11 | 0.11 |
| NH4(OH) (29.86%) | 0.093 | 0.093 |
| NaOH (10%) | — | — |

TABLE C-continued

|  |  |  |
|---|---|---|
| Triton BX | — | — |
| Monacor BE | — | — |
| Silwet Hydrostable | — | — |
| fragrance | — | — |
| propellant | 7.0 | 7.0 |
| di H$_2$O | q.s. | q.s. |
| pH | 10.04 | 10.47 |
| zinc ions (ppm) | 0 | 0 |
| can type | W | W |
| ASTM E 1052 (log10 reduction) | — | — |
| ASTM 1053 (log10 reduction) | PV1 = 3.00 | PV1 = 3.58 |
| AOAC Germicidal Spray | — | — |
| EN 13697 (log10 reduction) | — | — |
| EN 13697 *T. ment* (log10 reduction) | — | — |

|  | C83 | C84 | C85 | C86 | C87 | C88 |
|---|---|---|---|---|---|---|
| zinc acetate | — | — | — | — | — | — |
| zinc sulfate•7H$_2$O | — | — | — | — | — | — |
| zinc chloride | — | — | — | — | — | — |
| ethanol (100%) | 49.77 | 49.77 | 49.77 | 49.77 | 49.77 | 49.77 |
| BTC-65 (50%) | — | — | — | — | — | — |
| Onyxide 3300 (33%) | 0.337 | 0.337 | 0.337 | 0.337 | 0.337 | 0.337 |
| Neodol 91-6 | — | — | — | — | — | — |
| monoethanolamine | 0.02 | — | — | 0.13 | 0.65 | 2.51 |
| triethanolamine | 0.1 | 0.1 | 0.1 | 0.1 | 0.1 | 0.1 |
| sodium citrate•2H$_2$O | — | — | — | — | — | — |
| Citrasol 502 (50%) | 0.35 | 0.26 | 0.19 | 0.12 | 0.12 | 0.12 |
| NH4(OH) (29.86%) | 0.1 | 0.1 | 0.1 | 0.1 | 0.1 | 0.1 |
| NaOH (10%) | — | — | — | — | — | — |
| Triton BX | — | — | — | — | — | — |
| Monacor BE | 0.15 | 0.15 | 0.15 | 0.15 | 0.15 | 0.15 |
| Crodasol WS | 0.15 | 0.15 | 0.15 | 0.15 | 0.15 | 0.15 |
| fragrance | — | — | — | — | — | — |
| di H$_2$O | q.s. | q.s. | q.s. | q.s. | q.s. | q.s. |
| pH | 9.0 | 9.25 | 9.53 | 10.0 | 10.5 | 10.99 |
| zinc ions (ppm) | 0 | 0 | 0 | 0 | 0 | 0 |
| can type | S | S | S | S | S | S |
| ASTM 1053 (log10 reduction), 30 seconds contact time | — | — | — | PV1 = 0.73 | PV1 = 0.90 | PV1 = 0.90 |
| ASTM 1053 (log10 reduction), 5 minutes contact time | — | — | — | — | — | PV1 = 2.33 |

To each of comparative examples C83 through C88 was added an additional amount of 10% wt. of AB46 (based on the total weight of the example composition's constituents, which totaled 100% wt.) as the propellant constituent, and the reported microbicidal testing was performed utilizing the recovered liquid collected immediately after a quantity of the pressurized composition was dispensed from an aerosol canister

|  | C89 | C90 | C91 | C92 |
|---|---|---|---|---|
| zinc acetate | — | — | — | — |
| zinc sulfate•7H$_2$O | 0.13 | — | 0.13 | — |
| zinc chloride | — | — | — | — |
| ethanol (100%) | — | 44.22 | — | 44.22 |
| BTC-65 (50%) | — | — | — | — |
| Onyxide 3300 (33%) | — | 0.313 | — | 0.313 |
| Neodol 91-6 | — | — | 0.14 | 0.14 |
| monoethanolamine | 0.093 | 0.093 | — | — |
| triethanolamine | — | — | 0.97 | 0.97 |
| citric acid (anhy.) | 0.056 | 0.056 | 0.093 | 0.093 |
| sodium citrate•2H$_2$O | — | — | — | — |
| Citrasol 502 (50%) | — | — | 0.056 | 0.056 |
| NH4OH (29.86%) | 0.093 | 0.093 | — | — |
| NaOH (10%) | — | — | 0.093 | 0.093 |
| Triton BX | — | — | — | — |
| Monacor BE | 0.14 | 0.14 | — | — |
| Crodasol WS | 0.14 | 0.14 | 0.14 | 0.14 |
| Silwet Hydrostable | — | — | — | — |
| fragrance | — | 0.225 | — | 0.225 |
| propellant | 7.0 | 7.0 | 7.0 | 7.0 |
| di H$_2$O | q.s. | q.s. | q.s. | q.s. |
| pH | 10.60 | 10.54 | 10.60 | 10.54 |
| zinc ions (ppm) | 295.1 | 0 | 295.1 | 0 |
| can type | S | S | S | S |
| ASTM E 1052 (log10 reduction) | — | — | — | — |
| ASTM 1053 (log10 reduction) | — | — | — | — |
| AOAC Germicidal Spray | Sa = 30/30  Pa = 5/30 | Sa = 0/60  Pa = 0/30 | Sa = 30/30  Pa = 5/30 | Sa = 0/30  Pa = 0/60 |
| EN 13697 (log10 reduction) | — | — | — | — |
| EN 13697 *T. ment* (log10 reduction) | — | — | — | — |

TABLE 1

| (Examples) | | | | | | | | |
|---|---|---|---|---|---|---|---|---|
| | E1 | E2 | E3 | E4 | E5 | E6 | E7 | E8 |
| $CuSO_4 \cdot 5H_2O$ | 0.1 | 0.1 | 0.199 | 0.1 | 0.1 | 0.1 | 0.1 | 0.1 |
| ethanol (100%) | 25 | 45 | 45 | 75 | 35 | 35 | 50 | 50 |
| ethanol (95%) | — | — | — | — | — | — | — | — |
| BTC-65 (50%) | 0.2 | 0.2 | — | 0.2 | 0.2 | 0.2 | 0.2 | 0.2 |
| Onyxide 3300 (33%) | — | — | 0.30 | — | — | — | — | — |
| Neodol 91-6 | 0.1 | 0.1 | 0.1 | 0.1 | 0.1 | 0.1 | 0.1 | 0.1 |
| triethanolamine | 0.42 | 0.19 | 0.3 | 0.302 | 0.443 | — | — | 0.37 |
| ethanolamine | — | — | — | — | — | — | — | — |
| NH4OH (29.8%) | — | 0.1 | 0.09 | — | — | — | — | — |
| NaOH (10%) | — | — | — | — | — | — | — | — |
| Citrosol 502(50%) | — | — | — | — | — | — | — | — |
| ammonium acetate | — | — | — | — | — | 2.0 | 2.0 | — |
| Monacor BE | — | — | — | — | — | — | — | — |
| MEA-MIPA borate | — | 0.1 | 0.1 | — | — | — | — | — |
| Trilon BX | — | — | — | — | — | — | — | — |
| di $H_2O$ | 74.18 | 54.21 | 53.907 | 24.298 | 64.157 | 62.6 | 47.6 | 49.22 |
| pH | 8.09 | 9.5 | 8.85 | 8.23 | 8.06 | 6.82 | 7.08 | 8.06 |
| copper ion content (ppm) | 254 | 254 | 506 | 254 | 254 | 254 | 254 | 254 |
| appearance | colorless | light blue | light blue | light blue | light blue | light blue | light blue | light blue |
| ASTM E 1052 (log 10 reduction) | PV1 >3.67 | PV1 >5.27 PV1 >5.88 HAV >6.00 FCV >6.00 | PV1 >5.67 | PV1 >5.67 | PV1 >4.87 FCV >6.00 | — | — | PV1 >5.89 HAdV >5.00 HRV >6.00 HAV >6.00 FCV >6.00 |
| ASTM E 1053 (log 10 reduction) | — | 1 minute: PV1 >4.50 5 minutes: PV1 >4.50 | — | — | — | PV1 >4.38 HRV >2.75 Rota >2.5 | PV1 >3.50 | PV1 >3.50 PV1 >4.50 |
| AOAC Germicidal Spray Test | — | Sa = 0/60 Pa = 0/60 Mb = 0/30 (hard surface test) and ≥5.32 (suspension test) | — | — | — | — | — | Sa = 0/30 Pa = 0/30 |
| EN 13697 (log 10 reduction) | — | — | — | — | — | — | — | Sa >6.29, Ec >5.90, Pa >4.23, Eh >5.67 |
| *T. ment* (log 10 reduction) | — | — | — | — | — | — | — | >5.74 |

| | E9 | E10 | E11 | E12 | E13 | E14 |
|---|---|---|---|---|---|---|
| $CuSO_4 \cdot 5H_2O$ | 0.1 | 0.1 | 0.1 | 0.1 | 0.1 | 0.1 |
| ethanol (100%) | 40 | 40 | 40 | 40 | 40 | 40 |
| ethanol (95%) | — | — | — | — | — | — |
| BTC-65 (50%) | — | — | — | — | — | — |
| Onyxide 3300 (33%) | 0.303 | 0.303 | 0.303 | 0.303 | 0.303 | 0.303 |
| Neodol 91-6 | 0.1 | 0.1 | 0.1 | 0.1 | 0.1 | 0.1 |
| triethanolamine | 0.13 | 0.13 | 0.13 | 0.13 | 0.13 | 0.13 |
| ethanolamine | 0.05 | 0.05 | 0.05 | 0.05 | 0.05 | 0.05 |
| NH4OH (29.8%) | 0.12 | 0.12 | 0.12 | 0.12 | 0.12 | 0.12 |
| NaOH (10%) | — | — | — | — | — | — |
| Citrosol 502 (50%) | — | — | — | — | — | — |
| ammonium acetate | — | — | — | — | — | — |
| Monacor BE | — | — | — | — | — | — |
| MEA-MIPA borate | — | — | — | 0.20 | — | — |
| Trilon BX | — | — | — | — | — | — |
| IL2976 | — | 0.60 | 0.20 | — | 1.22 | 0.11 |
| di $H_2O$ | 59.2 | 58.6 | 59.0 | 59.0 | 58.0 | 59.1 |
| pH | 8.92 | 9.10 | 9.10 | 9.59 | 9.50 | 9.10 |
| copper ion content (ppm) | 254 | 254 | 254 | 254 | 254 | 254 |
| appearance | light blue | light blue | light blue | light blue | light blue | light blue |
| ASTM E 1052 (log 10 reduction) | PV1 = <2.77 | PV1 = <3.44 | PV1 = <3.54 | PV1 = <5.10 | PV1 = <3.10 | PV1 = <2.44 |
| ASTM E 1053 (log 10 reduction) | — | — | — | — | — | — |
| AOAC Germicidal Spray Test | — | — | — | — | — | — |
| EN 13697 (log 10 reduction) | — | — | — | — | — | — |
| *T. ment* (log 10 reduction) | — | — | — | — | — | — |

TABLE 1-continued

| (Examples) | | | | | |
|---|---|---|---|---|---|
| | E15 | E16 | E17 | E18 | E19 |
| CuSO₄·5H₂O | 0.1 | 0.1 | 0.1 | 0.1 | 0.1 |
| ethanol (100%) | 50 | 50 | 50 | 50 | 50 |
| ethanol (95%) | — | — | — | — | — |
| BTC-65 (50%) | 0.2 | 0.2 | 0.2 | 0.2 | 0.2 |
| Onyxide 3300 (33%) | — | — | — | — | — |
| Neodol 91-6 | 0.1 | — | 0.1 | 0.1 | 0.1 |
| triethanolamine | 0.48 | 0.37 | 0.41 | — | 0.48 |
| ethanolamine | — | — | — | — | — |
| NH4OH (29.8%) | — | — | — | — | — |
| NaOH (50%) | — | — | 0.054 | 0.03 | — |
| Citrosol 502(50%) | — | — | q.s. | — | — |
| sodium citrate | — | — | — | 0.1 | — |
| ammonium acetate | — | — | — | — | — |
| Monacor BE | — | — | — | — | 0.06 |
| di H₂O | 49.12 | 49.32 | 49.45 | 49.57 | 49.06 |
| pH | 8.06 | 8.10 | 8.24 | 8.45 | 8.52 |
| copper ion content (ppm) | 254 | 254 | 254 | 254 | 254 |
| appearance | light blue | light blue | cloudy | colorless | — |
| ASTM E 1052 (log 10 reduction) | — | PV1 = <4.73 | PV1 = <5.00 | PV1 >5.67 | — |
| ASTM E 1053 (log 10 reduction) | PV1 >3.50 PV1 >4.50 | — | — | — | — |
| AOAC Germicidal Spray Test | — | — | — | — | — |
| EN 13697 (log 10 reduction) | — | — | — | — | — |

| | E20 | E21 | E22 | E23 | E24 |
|---|---|---|---|---|---|
| CuSO₄·5H₂O | 0.1 | 0.1 | 0.1 | 0.1 | 0.1 |
| ethanol (100%) | — | 45 | 45 | 25 | 45 |
| ethanol (95%) | 50 | — | — | — | — |
| isopropanol | — | — | — | 20 | — |
| BTC-65 (50%) | 0.1 | — | — | 0.2 | 0.2 |
| Onyxide 3300 (33%) | — | 0.3 | 0.3 | — | — |
| Neodol 91-6 | 0.1 | 0.1 | 0.1 | 0.1 | 0.1 |
| Steol CS370 | — | — | — | — | 0.143 |
| triethanolamine | 0.31 | 0.48 | 0.18 | 0.4 | 0.43 |
| ethanolamine | — | — | — | — | — |
| NH4OH (29.8%) | — | — | 0.11 | — | — |
| NaOH (10%) | — | — | — | — | — |
| Citrosol 502(50%) | — | — | — | — | — |
| Citrosol 502(50%)/6 | — | — | — | — | — |
| ammonium acetate | — | — | — | — | — |
| Monacor BE | — | — | — | — | — |
| Trilon BX | — | — | — | — | — |
| di H₂O | 49.39 | 54.02 | 54.21 | 54.2 | 54.027 |
| pH | 8.1 | 8.2 | 9.17 | 8.03 | 8.08 |
| copper ion content (ppm) | 254 | 254 | 254 | 254 | 254 |
| appearance | light blue | light blue | light blue | light blue | dark blue, slight haze |
| ASTM E 1052 (log 10 reduction) | — | PV1 >5.27 HRV >4.83 HSV >6.00 | PV1 >4.50 | PV1 = 4.83 | PV1 >6.00 |
| ASTM E 1053 (log 10 reduction) | — | — | PV1 >4.50 (at 1 min), PV1 >4.50 (at 5 min) | — | — |
| AOAC Germicidal Spray Test | — | — | Sa = 0/60 Pa = 0/60 | — | — |
| EN 13697 (log 10 reduction) | — | — | — | — | — |

| | E25 | E26 | E27 | E28 | E29 | E30 | E31 | E32 |
|---|---|---|---|---|---|---|---|---|
| CuSO₄·5H₂O | 0.1 | 0.1 | 0.1 | 0.1 | 0.1 | 0.1 | 0.1 | 0.1 |
| ethanol (100%) | 45 | — | — | 45 | 45 | 45 | 45 | 35 |
| ethanol (95%) | — | — | — | — | — | — | — | — |
| isopropanol | — | 45 | — | — | — | — | — | — |
| n-propanol | — | — | 45 | — | — | — | — | — |
| BTC-65 (50%) | 0.2 | 0.2 | 0.2 | 0.2 | — | — | 0.2 | — |
| Onyxide 3300 (33%) | — | — | — | — | — | — | — | — |
| BTC-2125M | — | — | — | — | 0.2 | — | — | — |
| BTC-1010 | — | — | — | — | — | 0.2 | — | — |

TABLE 1-continued (Examples)

|  |  |  |  |  |  |  |  |  |
|---|---|---|---|---|---|---|---|---|
| Neodol 91-6 | 0.1 | 0.1 | 0.1 | — | 0.1 | 0.1 | — | — |
| Steol CS370 | — | — | — | 0.143 | — | — | — | — |
| Glucopon 425N | — | — | — | — | — | — | 0.2 | — |
| triethanolamine | 0.41 | 0.43 | 0.4 | 0.41 | 0.42 | 0.46 | 0.42 | — |
| ethanolamine | — | — | — | — | — | — | — | — |
| NH4OH (29.8%) | — | — | — | — | — | — | — | — |
| NaOH (10%) | — | — | — | — | — | — | — | — |
| Citrosol 502(50%) | — | — | — | — | — | — | — | 0.055 |
| ammonium acetate | — | — | — | — | — | — | — | — |
| Monacor BE | — | — | — | — | — | — | — | — |
| Trilon BX | — | — | — | — | — | — | — | — |
| di $H_2O$ | 54.19 | 54.17 | 54.2 | 54.14 | 54.18 | 54.14 | 54.08 | 64.8 |
| pH | 8.09 | 8.09 | 8.09 | 8.11 | 8.12 | 8.12 | 8.13 | 3.08 |
| copper ion content (ppm) | 254 | 254 | 254 | 254 | 254 | 254 | 254 | 254 |
| appearance | light blue | colorless | — | dark blue, slight haze | light blue | light blue | dark blue | Colorless |
| ASTM E 1052 (log 10 reduction) | PV1 >6.33 HRV >6.00 | PV1 = <3.17 | — | PV1 >6.00 | PV1 >6.00 | PV1 >6.00 | PV1 >6.00 | PV1 = <2.44 |
| ASTM E 1053 (log 10 reduction) | — | — | — | — | — | — | — | — |
| AOAC Germicidal Spray Test | Sa = 0/30 Pa = 0/30 | — | — | — | — | — | — | — |
| EN 13697 (log 10 reduction) | — | — | — | — | — | — | — | — |

|  | E33 | E34 | E35 | E36 | E37 | E38 | E39 | E40 |
|---|---|---|---|---|---|---|---|---|
| $CuSO_4 \cdot 5H_2O$ | 0.1 | 0.1 | 0.1 | 0.1 | 0.1 | 0.1 | 0.1 | 0.1 |
| ethanol (100%) | 45 | 45 | 40 | 38 | 45 | 38 | 38 | 38 |
| ethanol (95%) | — | — | — | — | — | — | — | — |
| isopropanol | — | — | — | — | — | — | — | — |
| n-propanol | — | — | — | — | — | — | — | — |
| BTC-65 (50%) | 0.2 | 0.2 | 0.2 | 0.2 | 0.2 | 0.2 | 0.2 | 0.2 |
| Onyxide 3300 (33%) | — | — | — | — | — | — | — | — |
| BTC-2125M | — | — | — | — | — | — | — | — |
| Neodol 91-6 | — | — | 0.1 | 0.1 | 0.1 | 0.1 | 0.1 | 0.1 |
| Steol CS370 | — | — | — | — | — | — | — | — |
| Ammonyx LO | 0.33 | — | — | — | — | — | — | — |
| Plurafac SL62 | — | 0.1 | — | — | — | — | — | — |
| triethanolamine | 0.48 | 0.43 | 0.42 | 0.015 | 0.0102 | 0.42 | 0.08 | — |
| ethanolamine | — | — | — | — | — | — | — | — |
| NH4OH (29.8%) | — | — | — | — | — | — | 0.11 | 0.11 |
| NaOH (10%) | — | — | — | — | — | — | — | — |
| Citrosol 502 (50%) | — | — | — | 0.08 | 0.066 | — | — | — |
| ammonium acetate | — | — | — | — | — | — | — | — |
| Monacor BE | — | — | — | — | — | — | — | — |
| Trilon BX | — | — | — | — | — | — | — | — |
| di $H_2O$ | 53.88 | 54.17 | 59.18 | 61.58 | 54.4 | 61.18 | 61.41 | 61.49 |
| pH | 8.18 | 8.14 | 8.10 | 5.0 | 5.04 | 8.08 | 9.20 | 9.38 |
| copper ion content (ppm) | 254 | 254 | 254 | 254 | 254 | 254 | 254 | — |
| appearance | dark blue | light blue | light blue | light blue | light blue | light blue | light blue | — |
| ASTM E 1052 (log 10 reduction) | PV1 >6.00 | PV1 >6.00 | PV1 >5.69 HRV >6.00 | PV1 >5.62 PV1 >4.73 HAV = >6.00 HAdV >4.50 FCV = <4.27 | PV1 = >4.73 | PV1 = <4.54 HRV >6.00 | PV1 >5.65 HAV >6.00 FCV >6.00 | — |
| ASTM E 1053 (log 10 reduction) | — | — | — | — | PV1 = 3 (5 min, aluminum Can, complete inactivation) PV1 = 3.5 (5 min, glass jar pressured, completed inactivation) | — | — | — |
| AOAC Germicidal Spray Test | — | — | — | — | — | — | Sa = 0/30 Pa = 0/30 | — |
| EN 13697 (log 10 reduction) | — | — | — | Sa >6.27 Ec >6.25 Pa >4.97 Eh >6.56 | — | — | — | — |

TABLE 1-continued (Examples)

| | E41 | E42 | E43 | E44 | E45 | E46 |
|---|---|---|---|---|---|---|
| $CuSO_4 \cdot 5H_2O$ | 0.1 | 0.1 | 0.1 | 0.1 | 0.1 | 0.1 |
| ethanol (100%) | 50 | 50 | 20 | — | — | 10 |
| ethanol (95%) | — | — | — | — | — | — |
| isopropanol | — | — | — | 35 | — | — |
| isobutanol | — | — | — | — | 35 | — |
| BTC-65 (50%) | — | — | — | — | — | — |
| Onyxide 3300 (33%) | — | — | — | — | — | — |
| Neodol 91-6 | 0.1 | — | — | — | — | — |
| triethanolamine | 0.34 | 0.45 | 0.45 | 0.45 | 0.40 | — |
| Citrasol 502 (50%) | — | — | — | — | — | — |
| NH4(OH) (29.86%) | 0.1 | 0.1 | — | — | — | — |
| NaOH (10%) | — | — | — | — | — | — |
| di H2O | 49.4 | 49.3 | 79.4 | 64.4 | 64.5 | 89.9 |
| pH | 10 | 10 | 8.12 | 8.0 | 8.08 | 5.01 |
| copper ion content (ppm) | 254 | 254 | 254 | 254 | 254 | 254 |
| appearance | light blue | light blue | colorless | colorless | light blue, two phases | colorless |
| ASTM E 1052 (log 10 reduction) | PV1 >3.73 | PV1 >3.73 | PV ≤2.10 | PV <0.23 | PV1 <1.33 | PV1 <0.73 |
| ASTM E 1053 (log 10 reduction) | PV1 >4.50 | — | — | — | — | — |
| AOAC Germicidal Spray | Sa = 0/60 (pass) Pa = 0/60 (pass) | — | — | — | — | — |
| EN 13697 (log 10 reduction) | — | — | — | — | — | — |
| T. ment (log 10 reduction) | — | — | — | — | — | — |

| | E47 | E48 | E49 | E50 | E51 | E52 | E53 |
|---|---|---|---|---|---|---|---|
| $CuSO_4 \cdot 5H_2O$ | 0.1 | 0.1 | 0.1 | 0.1 | 0.1 | 0.1 | 0.1 |
| ethanol (100%) | 35 | 35 | 35 | 30 | 25 | 20 | 10 |
| ethanol (95%) | — | — | — | — | — | — | — |
| BTC-65 (50%) | 0.2 | 0.2 | 0.2 | 0.2 | — | — | — |
| Onyxide 3300 (33%) | — | — | — | — | 0.30 | 0.30 | — |
| Neodol 91-6 | — | 0.1 | 0.1 | 0.1 | 0.1 | 0.1 | — |
| triethanolamine | 0.41 | 0.4 | 0.1 | 0.45 | 0.1 | 0.28 | — |
| ethanolamine | — | — | 0.1 | — | — | — | — |
| NH4OH (29.8%) | — | — | 0.17 | 0.21 | 0.10 | 0.18 | — |
| NaOH (10%) | — | — | 0.25 | — | — | — | — |
| Citrosol 502 (50%) | — | — | — | — | — | — | 0.04 |
| ammonium acetate | — | — | — | — | — | — | — |
| MEP-MIPA borate | — | — | — | — | 0.06 | — | — |
| Monacor BE | — | — | — | — | — | — | — |
| di $H_2O$ | 64.29 | 64.2 | 63.98 | 68.94 | 74.2 | 79.0 | 89.9 |
| pH | 8.1 | 8.1 | 11.03 | 9.51 | 9.21 | 9.16 | 3.07 |
| copper ion content (ppm) | 254 | 254 | 254 | 254 | 254 | 254 | — |
| appearance | light blue | light blue | light blue | light blue | light blue | light blue | colorless |
| ASTM E 1052 (log 10 reduction) | — | PV1 = 4.97, FCV >6.0 | PV1 >5.88 | PV1 >5.17, HAV >2.00, HAdV >4.50, HSV-1 >6.0 | PV1 3.23 | PV1 <3.00 FCV >6.00 | PV1 <0.73 |
| ASTM E 1053 (log 10 reduction) | — | — | — | — | — | — | — |
| AOAC Germicidal Spray Test | — | — | — | — | — | — | — |
| EN 13697 (log 10 reduction) | — | Sa >6.12 Ec >5.66 Pa >3.80 Eh >6.50 | — | Sa >6.62 Ec >6.63 Pa >6.69 Eh >6.74 | — | — | — |

| | E54 | E55 | E56 | E57 | E58 | E59 | E60 |
|---|---|---|---|---|---|---|---|
| $CuSO_4 \cdot 5H_2O$ | 0.1 | 0.1 | 0.1 | 0.1 | 0.1 | 0.1 | 0.1 |
| ethanol (100%) | 35 | 35 | 50 | 50 | 35 | 35 | 35 |
| ethanol (95%) | — | — | — | — | — | — | — |
| BTC-65 (50%) | — | — | — | — | — | — | — |
| Onyxide 3300 (33%) | — | — | — | — | — | — | — |
| Neodol 91-6 | 0.10 | — | 0.10 | — | — | — | — |
| triethanolamine | 0.41 | 0.41 | 0.34 | 0.45 | 0.23 | 0.97 | 0.20 |
| Citrasol 502 (50%) | — | — | — | — | 0.11 | — | 0.02 |
| NH4(OH) (29.86%) | — | — | — | — | — | 0.10 | 0.10 |
| NaOH (10%) | — | — | — | — | — | — | 0.37 |
| di H2O | 64.39 | 64.49 | 49.46 | 49.45 | 64.6 | 63.8 | 64.2 |
| pH | 8.09 | 8.10 | 8.01 | 8.11 | 5.10 | 8.95 | 10.98 |

TABLE 1-continued (Examples)

| | | | | | | | |
|---|---|---|---|---|---|---|---|
| copper ion content (ppm) | 254 | 254 | 254 | 254 | 254 | 254 | 254 |
| appearance | light blue | light blue | light blue | light blue | colorless | colorless | colorless |
| ASTM E 1052 (log 10 reduction) | PV1 <2.23 | PV1 +2.50 | PV1 <3.48 | PV1 ≤3.00 PV1 ≤4.09 | PV1 <1.5 | PV1 <2.27 | PV1 <3.67 |
| ASTM E 1053 (log 10 reduction) | — | — | — | — | — | — | — |
| AOAC Germicidal Spray | Sa = 0/60 Pa = 0/60 | — | Sa = 0/60 Pa = 0/60 | — | — | — | — |
| EN 13697 (log 10 reduction) | Sa >6.23 Ec >5.50 Pa >3.38 Eh >6.36 | — | Sa >6.23 Ec >5.50 Pa >3.38 Eh >6.36 | — | — | — | — |
| T. ment (log 10 reduction) | — | — | >5.74 | — | — | — | — |

| | E61 | E62 | E63 | E64 |
|---|---|---|---|---|
| CuSO$_4$•5H$_2$O | 0.099 | 0.099 | 0.05 | 0.025 |
| ethanol (100%) | 45 | 45 | 45 | 45 |
| ethanol (95%) | — | — | — | — |
| BTC-65 (50%) | — | — | — | — |
| Onyxide 3300 (33%) | 0.151 | 0.076 | 0.303 | 0.303 |
| Neodol 91-6 | 0.1 | 0.1 | 0.1 | 0.1 |
| triethanolamine | 0.35 | 0.28 | 0.2 | 0.1 |
| ethanolamine | — | — | — | — |
| NH4OH (29.8%) | 0.09 | 0.09 | 0.13 | 0.08 |
| NaOH (10%) | — | — | — | — |
| Citrosol 502 (50%) | — | — | — | — |
| ammonium acetate | — | — | — | — |
| Monacor BE | — | — | — | — |
| MEP-MIPA borate | — | — | 0.06 | 0.06 |
| di H$_2$O | 54.21 | 54.35 | 54.15 | 54.33 |
| pH | 8.97 | 9.05 | 9.84 | 10.06 |
| copper ion content (ppm) | 254 | 254 | 127 | 64 |
| appearance | light blue | light blue | light blue | light blue |
| ASTM E 1052 (log 10 reduction) | PV1 >5.67 | PV1 >5.67 | PV1 >5.67 | PV1 >5.67 |
| ASTM E 1053 (log 10 reduction) | — | — | — | — |
| AOAC Germicidal Spray Test | — | — | — | — |
| EN 13697 (log 10 reduction) | — | — | — | — |

| | E65 | E66 | E67 | E68 |
|---|---|---|---|---|
| CuSO$_4$•5H$_2$O | — | — | — | — |
| CuCl$_2$•2H$_2$O | 0.1 | — | — | — |
| Cu(AcO)$_2$•H$_2$O | — | 0.1 | — | — |
| Cu D-gluconate | — | — | 0.1 | — |
| Cu(I)Cl•H$_2$O | — | — | — | 0.1 |
| ethanol (100%) | 45 | 45 | 45 | 45 |
| ethanol (95%) | — | — | — | — |
| BTC-65 (50%) | 0.2 | 0.2 | 0.2 | — |
| Onyxide 3300 (33%) | — | — | — | 0.3 |
| Neodol 91-6 | 0.1 | 0.1 | 0.1 | 0.1 |
| triethanolamine | 0.6 | 0.45 | 0.45 | 0.45 |
| ethanolamine | — | — | — | — |
| NH4OH (29.8%) | — | — | — | — |
| NaOH (10%) | — | — | — | — |
| Citrosol 502 (50%) | — | — | — | — |
| di H$_2$O | 54.0 | 54.15 | 54.35 | 54.05 |
| pH | 8.1 | 8.03 | 8.03 | 8.14 |
| copper ion content (ppm) | 372 | 318 | 140 | 641 |
| appearance | light blue | light blue | — | light blue, slight haze |
| ASTM E 1052 (log 10 reduction) | — | — | PV1 = <5.50 | FCV = >6.00 |
| ASTM E 1053 (log 10 reduction) | — | — | — | — |
| EN 13697 (log 10 reduction) | — | — | — | — |

| | E69 | E70 | E71 | E72 | E73 | E74 |
|---|---|---|---|---|---|---|
| CuSO$_4$•5H$_2$O | 0.025 | 0.20 | 0.10 | 0.05 | 0.10 | 0.05 |
| BTC-65 (50%) | 0.015 | 0.19 | 0.19 | 0.19 | 0.1 | 0.10 |
| Neodol 91-6 | — | 0.6 | 0.6 | — | 0.6 | 0.6 |
| Ammonyx LO | — | — | — | — | — | — |
| triethanolamine | — | — | 0.31 | 0.15 | 0.31 | 0.15 |
| ethanolamine | — | — | — | — | — | — |
| NaOH (10%) | — | — | — | — | — | — |

TABLE 1-continued (Examples)

| | | | | | | |
|---|---|---|---|---|---|---|
| NaOH (50%) | — | — | — | — | — | — |
| Citrosol 502 (50%) | — | — | — | — | — | — |
| di H$_2$O | 99.96 | 99.01 | 98.8 | 99.6 | 98.89 | 99.1 |
| pH | 5.43 | 5.07 | 8.1 | 8.07 | 8.01 | 8.06 |
| copper ion content (ppm) | 63.62 | 509 | 254 | 127.25 | 254 | 127.25 |
| appearance | light blue | light blue | light blue | light blue | light blue | light blue |
| ASTM E 1052 (log 10 reduction) | — | — | — | — | — | — |
| ASTM E 1053 (log 10 reduction) | — | — | — | — | — | — |
| AOAC Germicidal Spray Test | — | — | — | — | — | — |
| EN 13697 (log 10 reduction) | Sa <0.79 Pa = 2.05 | Sa <0.99 | Sa = 4.63 Ec = 5.99 Pa = 2.96 Eh = 6.68 | Sa = 5.82 Ec = 5.99 Pa = 3.52 Eh = 6.68 | Sa = 4.29 Ec >6.24 Pa = 4.01 Eh = 4.89 | Sa = 4.41 Ec >6.24 Pa = 2.95 Eh = 4.82 |
| T. ment (log 10 reduction) | — | — | — | — | — | — |

| | E75 | E76 | E77 |
|---|---|---|---|
| CuSO$_4$•5H$_2$O | 0.10 | 0.10 | 0.10 |
| BTC-65 (50%) | — | — | — |
| BTC-2125M | 0.2 | — | — |
| BTC-1010 | — | 0.20 | — |
| Onyxide 3300 (33%) | — | — | 0.30 |
| Neodol 91-6 | 0.1 | 0.1 | 0.1 |
| Ammonyx LO | — | — | — |
| triethanolamine | 0.31 | 0.31 | 0.31 |
| ethanolamine | — | — | — |
| NaOH (10%) | — | — | — |
| NaOH (50%) | — | — | — |
| Citrosol 502 (50%) | — | — | — |
| di H$_2$O | 99.30 | 99.3 | 99.2 |
| pH | 8.0 | 8.03 | 8.0 |
| copper ion content (ppm) | 254 | 254 | 254 |
| appearance | light blue | light blue | light blue. slight haze |
| ASTM E 1052 (log 10 reduction) | HAdV <2.5 | HAdV <1.83 | HAdV <1.00 |
| ASTM E 1053 (log 10 reduction) | — | — | — |
| AOAC Germicidal Spray Test | — | — | Sa = fail (37/60) Pa = fail (2/60) |
| EN 13697 (log 10 reduction) | — | — | — |
| T. ment (log 10 reduction) | — | — | — |

| | E78 | E79 | E80 |
|---|---|---|---|
| CuSO4•5H2O | 0.1 | 0.1 | 0.1 |
| ethanol (100%) | 5 | 10 | 50 |
| ethanol (95%) | — | — | — |
| BTC-65 (50%) | 0.2 | 0.2 | 0.2 |
| Onyxide 3300 (33%) | — | — | — |
| Neodol 91-6 | 0.1 | 0.1 | 0.1 |
| Plurafac SL62 | — | — | — |
| triethanolamine | 0.31 | 0.31 | — |
| citric acid (1.56%) | — | — | — |
| di H2O | 94.3 | 89.3 | 49.60 |
| pH | 8.04 | 7.97 | 4.74 |
| copper ion content (ppm) | 254 | 254 | — |
| appearance | medium blue | light blue | — |
| ASTM E 1052 (log 10 reduction) | PV1 = <0.23 IV-A >5.00 HSV >6.00 | PV1 <0.9 | — |
| ASTM E 1053 (log 10 reduction) | — | — | HRV = 1.50 |

TABLE 1-continued (Examples)

| | | | | |
|---|---|---|---|---|
| AOAC Germicidal Spray | Sa = 0/30 Pa = 0/30 | — | — | |
| EN 13697 (log 10 reduction) | Sa = 3.48 Ec >6.58 Pa >5.16 Eh = 3.43 | — | — | |
| T. ment (log 10 reduction) | — | | | |

| | E81 | E82 | E83 | E84 | E85 | E86 |
|---|---|---|---|---|---|---|
| CuSO4•5H2O | 0.1 | 0.1 | 0.099 | 0.1 | 0.099 | 0.099 |
| ethanol (100%) | 10 | 10 | 12.0 | — | 17.5 | 35.0 |
| ethanol (95%) | — | — | — | — | — | — |
| isopropanol | — | — | 12.0 | — | — | — |
| n-propanol | — | — | 12.0 | 35.0 | — | — |
| isobutanol | — | — | — | — | 17.5 | — |
| propylene glycol n-propyl ether | — | — | — | — | — | 25.0 |
| BTC-65 (50%) | — | — | — | — | — | — |
| Onyxide 3300 (33%) | — | — | — | — | — | — |
| Neodol 91-6 | — | — | — | — | — | — |
| triethanolamine | 0.30 | 0.30 | 0.40 | 0.50 | 0.40 | 0.40 |
| Citrasol 502 (50%) | — | — | — | — | — | — |
| NH4(OH) (29.86%) | 0.14 | 0.12 | — | — | — | — |
| NaOH (10%) | — | 0.35 | — | — | — | — |
| di H2O | 89.5 | 89.1 | 63.5 | 64.4 | 64.5 | 39.5 |
| pH | 9.07 | 10.97 | 7.89 | 8.03 | 7.90 | 7.89 |
| copper ion content (ppm) | 254 | 254 | 254 | 254 | 254 | 254 |
| appearance | colorless | colorless | light blue | colorless | light blue | light blue |
| ASTM E 1052 (log 10 reduction) | PV1 ≤2.10 FCV <1.00 | PV1 <0.73 | PV1 <0.67 | PV1 <1.33 | PV1 <1.33 | PV1 <0.50 |
| ASTM E 1053 (log 10 reduction) | — | — | — | — | — | — |
| AOAC Germicidal Spray | — | — | — | — | — | — |
| EN 13697 (log 10 reduction) | — | — | — | — | — | — |
| T. ment (log 10 reduction) | — | — | — | — | — | — |

| | E87 | E88 | E89 | E90 | E91 | E92 |
|---|---|---|---|---|---|---|
| CuSO4•5H2O | 0.1 | 0.1 | 0.1 | 0.1 | 0.1 | 0.1 |
| ethanol (100%) | 35.0 | 35.0 | 35.0 | 35.0 | 5.0 | 5.0 |
| ethanol (95%) | — | — | — | — | — | — |
| BTC-65 (50%) | 0.2 | 0.2 | 0.2 | 0.2 | 0.2 | 0.2 |
| Onyxide 3300 (33%) | — | — | — | — | — | — |
| decyl glucoside | 1.0 | 1.0 | 5.0 | 5.0 | 5.0 | 5.0 |
| stearalkonium chloride | — | — | — | — | — | — |
| triethanolamine | — | — | — | — | — | — |
| Citrasol 502 (50%) | — | — | — | — | — | — |
| NH4(OH) (29.86%) | — | — | — | — | — | — |
| NaOH (10%) | — | — | — | — | — | — |
| di H2O | q.s. | q.s. | q.s. | q.s. | q.s. | q.s. |
| pH | 5.60 | 7.77 | 5.49 | 7.90 | 5.8 | 8.34 |
| copper ion content (ppm) | 254 | 254 | 254 | 254 | 254 | 254 |
| appearance | — | — | — | — | — | — |
| ASTM E 2315 (log 10 reduction) | Sa >6.36 Sa >7.09 Ec >6.49 | Sa >6.36 Sa >7.09 Ec >6.49 | Sa >6.36 Sa >7.09 Ec >6.49 | Sa >6.36 Sa >7.09 Ec >6.49 | Sa = 1.27 Ec = 2.15 | Sa = 1.73 Ec = 1.69 |
| ASTM E 1052 (log 10 reduction) | — | — | — | — | — | — |
| ASTM E 1053 (log 10 reduction) | — | — | — | — | — | — |
| AOAC Germicidal Spray | — | — | — | — | — | — |
| EN 13697 (log 10 reduction) | — | — | — | — | — | — |
| T. ment (log 10 reduction) | — | — | — | — | — | — |

| | E93 | E94 | E95 | E96 | E97 | E98 | E99 | E100 |
|---|---|---|---|---|---|---|---|---|
| CuSO4•5H2O | 0.1 | 0.1 | 0.1 | 0.1 | 0.1 | 0.1 | 0.1 | 0.1 |
| ethanol (100%) | — | — | — | — | — | — | — | — |
| ethanol (95%) | — | — | — | — | — | — | — | — |
| BTC-65 (50%) | 0.2 | 0.2 | 0.2 | 0.2 | 0.2 | 0.2 | 0.2 | 0.2 |
| Onyxide 3300 (33%) | — | — | — | — | — | — | — | — |
| decyl glucoside | 1.0 | 1.0 | — | — | 5.0 | 5.0 | 20.0 | 20.0 |
| stearalkonium chloride | — | — | 1.0 | 1.0 | — | — | — | — |
| triethanolamine | — | — | — | — | — | — | — | — |
| Citrasol 502 (50%) | — | — | — | — | — | — | — | — |
| NH4(OH) (29.86%) | — | — | — | — | — | — | — | — |
| NaOH (10%) | — | — | — | — | — | — | — | — |

TABLE 1-continued (Examples)

| | | | | | | | | |
|---|---|---|---|---|---|---|---|---|
| di H2O | q.s. | q.s. | q.s. | q.s. | q.s. | q.s. | q.s. | q.s. |
| pH | 5.81 | 7.94 | 5.25 | 8.26 | 5.55 | 8.04 | 5.01 | 7.80 |
| copper ion content (ppm) | 254 | 254 | 254 | 254 | 254 | 254 | 254 | 254 |
| appearance | — | — | — | — | — | — | — | — |
| ASTM E 2315 (log 10 reduction) | Sa >6.43 Ec = 6.24 | Sa >6.43 Ec >6.54 | Sa >6.79 Ec >6.58 | Sa >6.71 Ec >6.49 | Sa = 1.64 Ec = 3.38 | Sa = 2.09 Ec = 2.43 | Sa = 1.07 Ec = 1.20 | Sa = 0.96 Ec = 1.13 |
| ASTM E 1052 (log 10 reduction) | — | — | — | — | — | — | — | — |
| ASTM E 1053 (log 10 reduction) | — | — | — | — | — | — | — | — |
| AOAC Germicidal Spray | — | — | — | — | — | — | — | — |
| EN 13697 (log 10 reduction) | — | — | — | — | — | — | — | — |
| T. ment (log 10 reduction) | — | — | — | — | — | — | — | — |

TABLE 2

| | E101 | E102 | E103 | E104 | E105 | E106 |
|---|---|---|---|---|---|---|
| $CuSO_4 \cdot 5H_2O$ | 0.108 | 0.108 | 0.108 | 0.108 | 0.108 | 0.108 |
| ethanol (100%) | — | — | — | — | — | — |
| ethanol (95%) | 40.53 | 40.53 | 40.53 | 46.35 | 46.35 | 46.35 |
| BTC-65 (50%) | — | — | — | — | — | — |
| Onyxide 3300 (33%) | 0.34 | 0.34 | 0.34 | 0.34 | 0.34 | 0.34 |
| Neodol 91-6 | — | — | — | — | — | — |
| Tween 20 | 0.054 | 0.054 | 0.054 | 0.054 | 0.054 | 0.054 |
| Silwet Hydrostable 212 | 0.108 | 0.108 | 0.108 | 0.108 | 0.108 | 0.108 |
| citric acid (1.56%) | q.s. | q.s. | — | q.s. | q.s. | — |
| monoethanolamine | — | — | q.s. | — | — | q.s. |
| Monacor BE | 0.269 | 0.269 | 0.269 | 0.269 | 0.269 | 0.269 |
| fragrance | 0.25 | 0.25 | 0.25 | 0.25 | 0.25 | 0.25 |
| di H2O | 58.34 | 58.34 | 58.34 | 52.52 | 52.52 | 52.52 |
| propellant* | +7% vol | +7% vol | +7% vol | +7% vol | +7% vol | +7% vol |
| pH | 7.5 | 9 | 10.5 | 7.5 | 9 | 10.5 |
| copper ion content (ppm) | 254 | 254 | 254 | 254 | 254 | 254 |
| appearance | light blue | light blue | light blue | light blue | light blue | light blue |
| ASTM E 1052 (log10 reduction) | — | — | — | — | — | — |
| ASTM E 1053 (log10 reduction) | — | 10 min: PV1 = 0.75 PV1 = 1.0 viral titer = 2.75 10 min: HRV >1.25 HRV 0.5 viral titer = 2.75 | 10 min: PV1 = 4.25 PV1 = 3.50 viral titer = 6.0 | — | 10 min: PV1 >1.25 PV1 = 1.0 viral titer = 2.75 10 min: HRV = 1.0 HRV = 0.75 viral titer = 2.75 | 10 min: PV1 >4.5 PV >4.5 viral titer = 6.00 |
| AOAC Germicidal Spray | — | — | — | — | — | — |
| EN 13697 (log10 reduction) | — | — | — | — | — | — |
| T. ment (log10 reduction) | — | — | — | — | — | — |

| | E107 | E108 | E109 | E110 | E111 | E112 |
|---|---|---|---|---|---|---|
| $CuSO_4 \cdot 5H_2O$ | 0.108 | 0.108 | 0.108 | 0.108 | 0.108 | 0.108 |
| ethanol (100%) | — | — | — | — | — | — |
| ethanol (95%) | 52.187 | 52.187 | 46.35 | 46.35 | 40.53 | 40.53 |
| BTC-65 (50%) | — | — | — | — | — | — |
| Onyxide 3300 (33%) | 0.34 | 0.34 | 0.34 | 0.34 | 0.34 | 0.34 |
| Neodol 91-6 | — | — | — | — | — | — |
| Tween 20 | 0.054 | 0.054 | 0.054 | — | 0.054 | — |
| Silwet Hydrostable 212 | 0.108 | 0.108 | 0.108 | — | 0.108 | — |
| citric acid (1.56%) | q.s. | q.s. | q.s. | q.s. | — | — |
| monoethanolamine | — | — | — | — | q.s. | q.s. |
| Monacor BE | 0.269 | 0.269 | 0.269 | — | — | — |
| fragrance | 0.25 | 0.25 | 0.25 | — | 0.25 | 0.25 |
| di H2O | 46.68 | 46.68 | 52.82 | 53.21 | 58.64 | 59.01 |
| propellant* | +7% vol | +7% vol | +7% vol | +7% vol | +7% vol | +7% vol |
| pH | 7.5 | 10.5 | 9 | 9 | 10.5 | 10.5 |
| copper ion content (ppm) | 254 | 254 | 254 | 254 | 254 | 254 |
| appearance | light blue | light blue | light blue | light blue | light blue | light blue |
| ASTM E 1052 (log10 reduction) | — | — | PV1 >4.83 | PV1 >4.83 | PV1 >4.83 | PV1 >4.83 |
| ASTM E 1053 (log10 reduction) | — | 10 min: PV1 >4.50 PV1 >4.50 Viral titer = 6.00 | 10 min: PV1 = 2.75 PV1 = 3.25 viral titer = 4.75 | 10 min: PV1 = 2.75 PV1 = 3.25 viral titer = 4.75 | 10 min: PV1 = 2.00 PV1 >3.25 viral titer = 4.75 | 10 min: PV1 = 2.25 PV1 >3.25 viral titer = 4.75 |

TABLE 2-continued

| | | | | | | | |
|---|---|---|---|---|---|---|---|
| AOAC Germicidal Spray | — | — | — | — | — | — | — |
| EN 13697 (log10 reduction) | — | — | — | — | — | — | — |
| T. ment (log10 reduction) | — | — | — | — | — | — | — |

| | E113 | E114 | E115 | E116 | E117 | E118 | E119 |
|---|---|---|---|---|---|---|---|
| $CuSO_4 \cdot 5H_2O$ | 0.11 | 0.11 | 0.11 | 0.11 | 0.11 | 0.11 | 0.11 |
| ethanol (100%) | 46.35 | 46.35 | 46.35 | 46.35 | 46.35 | 46.35 | 46.35 |
| ethanol (95%) | — | — | — | — | — | — | — |
| BTC-65 (50%) | — | — | — | — | — | — | — |
| Onyxide 3300 (33%) | 0.34 | 0.34 | 0.34 | 0.34 | 0.34 | 0.34 | 0.34 |
| Neodol 91-6 | — | — | — | — | — | — | — |
| Tween 20 | — | — | — | — | — | — | — |
| Silwet Hydrostable 212 | — | — | — | — | — | — | — |
| citric acid (50%) | q.s. | q.s. | q.s. | q.s. | q.s. | q.s. | q.s. |
| monoethanolamine | q.s. | q.s. | q.s. | 0.10 | q.s. | 0.050 | q.s. |
| morpholine | 0.37 | — | — | — | — | — | — |
| NH4OH (29.6%) | — | 0.098 | 0.169 | — | — | 0.068 | 0.17 |
| isopropylamine | — | — | — | — | 0.09 | — | — |
| Monacor BE | — | — | — | — | — | — | — |
| fragrance | — | — | — | — | — | — | — |
| di $H_2O$ | 52.8 | 53.1 | 52.9 | 53.1 | 53.1 | 53.1 | 53.0 |
| propellant* | +7% vol. | +7% vol. | +7% vol. | +7% vol. | +7% vol. | +7% vol. | +7% vol. |
| pH | 9.0 | 9.0 | 9.0 | 9.0 | 9.0 | 9.0 | 9.0 |
| copper ion content (ppm) | 280 | 280 | 280 | 280 | 280 | 280 | 280 |
| appearance | light blue | light blue | light blue | light blue | light blue | light blue | light blue |
| ASTM E 1052 (log10 reduction) | PV1 >5.00 | PV1 >5.00 | PV1 >5.00 | PV1 >5.00 | — | PV1 >5.00 | PV1 >5.00 |
| ASTM E 1053 (log10 reduction) | 10 min: PV1 = 0.5 PV1 = 0.75 viral titer = 4.25 | 10 min: PV1 = 2.00 PV1 = 2.00 viral titer = 4.25 | 10 min: PV1 = 2.00 PV1 = 2.00 viral titer = 4.25 | 10 min: PV1 = 3.75 PV1 = 3.75 viral titer = 4.25 | — | 10 min: PV1 = 3.00 PV1 = 3.75 viral titer = 4.25 | 10 min: PV1 = 1.25 PV1 = 1.75 viral titer = 4.25 |
| AOAC Germicidal Spray | — | — | — | — | — | — | — |
| EN 13697 (log10 reduction) | — | — | — | — | — | — | — |
| T. ment (log10 reduction) | — | — | — | — | — | — | — |

| | E120 | E121 | E122 | E123 | E124 | E125 |
|---|---|---|---|---|---|---|
| $CuSO_4 \cdot 5H_2O$ | 0.11 | 0.11 | 0.11 | 0.11 | 0.11 | 0.11 |
| ethanol (100%) | 46.35 | 46.35 | 46.35 | 46.35 | 46.35 | 40 |
| ethanol (95%) | — | — | — | — | — | — |
| BTC-65 (50%) | — | — | — | — | — | — |
| Onyxide 3300 (33%) | 0.34 | 0.34 | 0.34 | 0.34 | 0.34 | 0.30 |
| Neodol 91-6 | — | — | — | — | — | 0.093 |
| Tween 20 | 0.05 | 0.05 | 0.05 | 0.05 | 0.05 | — |
| Silwet Hydrostable 212 | 0.11 | 0.11 | 0.11 | 0.11 | 0.11 | — |
| citric acid (50%) | q.s. | — | — | — | — | — |
| monoethanolamine | q.s. | q.s. | q.s. | q.s. | q.s. | 0.09 |
| triethanolamine | 0.20 | 0.20 | — | — | 0.2 | 0.09 |
| morpholine | — | — | — | — | — | — |
| NH4OH (29.6%) | 0.05 | 0.05 | — | — | 0.05 | 0.05 |
| isopropylamine | 0.05 | — | — | — | — | — |
| Monacor BE | — | — | — | — | — | — |
| fragrance | — | 0.25 | 0.25 | 0.25 | 0.25 | — |
| di $H_2O$ | 53.1 | 52.54 | 52.79 | 52.79 | 52.54 | 52.3 |
| propellant* | +7% vol. | +7% vol. | — | — | — | — |
| pH | 9.0 | 9.0 | 9 | 10.5 | 10.5 | 9.38 |
| copper ion content (ppm) | 280 | 280 | 280 | 280 | 280 | 280 |
| appearance | light blue | light blue | light blue | light blue | light blue | light blue |
| ASTM E 1052 (log10 reduction) | — | PV1 >5.00 | — | — | — | — |
| ASTM E 1053 (log10 reduction) | — | 10 min: PV1 = 3.50 PV1 = 3.50 viral titer = 7.25 | 10 min: PV1 = 4.25 PV1 = 4.50 viral titer = 7.25 | 10 min: PV1 = 4.75 PV1 = 3.50 viral titer = 7.25 | 10 min: PV1 = 4.75 PV1 = 3.75 viral titer = 7.25 | 10 min: PV1 = 4.25 PV1 = 4.00 viral titer = 7.25 10 min: HRV >3.25 HRV >3.25 viral tier = 4.75 |
| AOAC Germicidal Spray | — | — | — | — | — | — |
| EN 13697 (log10 reduction) | — | — | — | — | — | — |
| T. ment (log10 reduction) | — | — | — | — | — | — |

| | E126 | E127 | E128 | E129 | E130 | E131 | E132 | E133 |
|---|---|---|---|---|---|---|---|---|
| $CuSO_4 \cdot 5H_2O$ | 0.11 | 0.11 | 0.11 | 0.11 | 0.54 | 0.54 | 1.08 | 1.08 |
| ethanol (100%) | 46.35 | 46.35 | 46.35 | 46.35 | 46.5 | 46.5 | 46.5 | 46.5 |
| ethanol (95%) | — | — | — | — | — | — | — | — |
| BTC-65 (50%) | — | — | — | — | — | — | — | — |
| Onyxide 3300 (33%) | 0.34 | 0.34 | 0.34 | 0.34 | 0.34 | 0.34 | 0.34 | 0.34 |
| Neodol 91-6 | 0.15 | 0.15 | 0.15 | 0.15 | 0.15 | 0.15 | 0.15 | 0.15 |

TABLE 2-continued

| | | | | | | | | |
|---|---|---|---|---|---|---|---|---|
| Tween 20 | — | — | — | — | — | — | — | — |
| Silwet Hydrostable 212 | — | — | — | — | — | — | — | — |
| citric acid (50%) | — | — | — | — | — | — | — | — |
| monoethanolamine | q.s. | q.s. | q.s. | q.s. | 0.38 | 2.23 | 0.90 | 4.07 |
| triethanolamine | 0.1 | 0.1 | 0.2 | 0.2 | 0.2 | 0.2 | 0.2 | 0.2 |
| morpholine | — | — | — | — | — | — | — | — |
| NH4OH (29.6%) | 0.05 | 0.05 | 0.05 | 0.05 | 0.05 | 0.05 | 0.05 | 0.05 |
| isopropylamine | — | — | — | — | — | — | — | — |
| Monacor BE | — | — | — | — | — | — | — | — |
| fragrance | 0.25 | 0.25 | 0.25 | 0.25 | 0.25 | 0.25 | 0.25 | 0.25 |
| di H$_2$O | 52.65 | 52.65 | 52.55 | 52.55 | 52.22 | 52.22 | 51.68 | 51.68 |
| propellant* | +7% vol. | +7% vol. | +7% vol. | +7% vol. | +7% vol. | +7% vol. | +7% vol. | +7% vol. |
| pH | 9.0 | 10.5 | 9.0 | 10.5 | 9.01 | 10.5 | 9.0 | 10.5 |
| copper ion content (ppm) | 280 | 280 | 280 | 280 | 1374 | 1374 | 2748 | 2748 |
| appearance | light blue | light blue | light blue | light blue | medium blue | medium blue | medium blue | medium blue |
| ASTM E 1052 (log10 reduction) | — | — | — | — | — | — | — | — |
| ASTM E 1053 (log10 reduction) | 10 min: PV1 = 3.83 viral titer = 7.50 | 10 min: PV1 >5.00 viral titer = 7.50 | 10 min: PV1 = 2.27 viral titer = 7.50 | 10 min: PV1 = 2.83 viral titer = 7.50 | 10 min: PV1 = 4.17 viral titer = 7.50 | 10 min: PV1 = 4.50 viral titer = 7.50 | 10 min: PV1 = 4.83 viral titer = 7.50 | 10 min: PV1 = 5.00 viral titer = 7.50 |
| | 10 min: HRV >3.25 HRV >3.25 viral tier = 4.75 | 10 min: HRV >3.25 HRV >3.25 viral tier = 4.75 | 10 min: HRV >3.25 HRV >3.25 viral tier = 4.75 | 10 min: HRV >3.25 HRV >3.25 viral tier = 4.75 | | | | |
| AOAC Germicidal Spray | — | — | — | — | — | — | — | — |
| EN 13697 (log10 reduction) | — | — | — | — | — | — | — | — |
| T. ment (log10 reduction) | — | — | — | — | — | — | — | — | propellant* - the measured constituents of the liquid composition (which provides 100% wt.) was charged to a pressurizable vessel (e.g, Wheaton bottle, aerosol canister, to which was further added 7% by volume of the indicated propellant, and thereafter the vessel was sealed.

TABLE 1

| | E134 | E135 | E136 | E137 | E138 | E139 | E140 | E141 |
|---|---|---|---|---|---|---|---|---|
| zinc acetate | 0.08 | — | — | 0.08 | 0.08 | 0.08 | 0.08 | — |
| zinc sulfate•7H$_2$O | — | 0.08 | 0.08 | — | — | — | — | 0.08 |
| zinc chloride | — | — | — | — | — | — | — | — |
| ethanol (100%) | 35.0 | 40.0 | 40.0 | 45.0 | 45.0 | — | — | — |
| BTC-65 (50%) | — | — | — | — | — | 0.20 | 0.20 | — |
| Onyxide 3300 (33%) | — | — | — | — | — | — | — | 0.30 |
| Neodol 91-6 | 0.10 | — | 0.10 | 0.10 | 0.10 | 0.10 | 0.10 | — |
| monoethanolamine | — | 0.06 | 0.07 | — | 0.02 | 0.05 | — | 0.06 |
| triethanolamine | 0.07 | 0.10 | 0.10 | 0.12 | 0.27 | — | 0.27 | 0.10 |
| sodium citrate•2H$_2$O | 0.20 | 0.10 | 0.10 | 0.20 | — | — | — | 0.10 |
| Citrasol 502 (50%) | — | 0.05 | 0.05 | — | 0.14 | 0.012 | — | 0.06 |
| NH4(OH) (29.86%) | 0.07 | — | — | 0.03 | 0.12 | — | 0.12 | — |
| NaOH (10%) | — | — | — | — | — | — | — | — |
| Triton BX | — | — | — | — | — | — | — | — |
| Monacor BE | — | — | — | — | — | — | — | — |
| Silwet Hydrostable | — | — | — | — | — | — | — | — |
| fragrance | — | — | — | — | — | — | — | — |
| di H$_2$O | q.s. | q.s. | q.s. | q.s. | q.s. | q.s. | q.s. | q.s. |
| pH | 9.11 | 9.00 | 9.13 | 8.05 | 8.74 | 8.15 | 8.66 | 9.13 |
| zinc ions (ppm) | 285 | 182 | 182 | 285 | 285 | 285 | 285 | 182 |
| ASTM E 1052 (log10 reduction) | PV1 = 2.00 | PV1 = 2.56 | PV1 = 2.73 | PV1 = 2.50 | PV1 ≥5.00 | PV1 = 2.17 | PV1 = 1.83 | PV1 = 2.67 |
| ASTM 1053 (log10 reduction) | — | — | — | — | — | — | — | — |
| AOAC Germicidal Spray | — | — | — | — | — | — | — | — |
| EN 13697 (log10 reduction) | Sa ≥6.75 Ec ≥6.06 Pa ≥5.41 Eh ≥6.66 | — | — | — | Sa ≥6.75 Ec ≥6.06 Pa ≥5.41 Eh ≥6.66 | Sa = 3.90 Ec ≥6.06 Pa ≥5.41 Eh ≥6.66 | Sa = 5.01 Ec ≥6.06 Pa ≥5.41 Eh ≥6.66 | — |
| EN 13697 T. ment (log10 reduction) | ≥4.61 | — | — | — | ≥4.61 | =1.40 | =1.09 | — |

| | E142 | E143 | E144 | E145 | E146 | E147 |
|---|---|---|---|---|---|---|
| zinc acetate | — | — | 0.08 | 0.08 | 0.12 | 0.12 |
| zinc sulfate•7H$_2$O | 0.10 | 0.12 | — | — | — | — |
| zinc chloride | — | — | — | — | — | — |
| ethanol (100%) | 20.0 | 35.0 | 35.0 | 35.0 | 38.0 | 38.0 |
| BTC-65 (50%) | — | — | 0.20 | 0.20 | — | — |
| Onyxide 3300 (33%) | 0.30 | 0.303 | — | — | 0.303 | 0.303 |
| Neodol 91-6 | 0.10 | 0.10 | 0.10 | 0.10 | 0.10 | 0.10 |
| monoethanolamine | 0.20 | — | — | 0.74 | — | — |
| triethanolamine | 0.10 | 0.15 | 0.07 | — | 0.15 | — |
| sodium citrate•2H$_2$O | 0.08 | 0.20 | 0.20 | — | — | 0.20 |
| Citrasol 502 (50%) | 0.32 | — | — | — | 0.09 | — |

TABLE 1-continued

|  |  |  |  |  |  |  |
|---|---|---|---|---|---|---|
| NH4(OH) (29.86%) | — | 0.17 | 0.06 | — | 0.13 | 0.08 |
| NaOH (10%) | — | — | — | — | — | — |
| Triton BX | — | — | — | — | — | — |
| Monacor BE | — | — | — | — | — | — |
| Silwet Hydrostable | — | — | — | — | — | — |
| fragrance | — | — | — | — | — | — |
| di H$_2$O | q.s. | q.s. | q.s. | q.s. | q.s. | q.s. |
| pH | 9.03 | 9.50 | 9.05 | 10.76 | 9.28 | 9.46 |
| zinc ions (ppm) | 227 | 272.8 | 285 | 285 | 272.8 | 272.8 |
| ASTM E 1052 (log10 reduction) | PV1 = 2.50 | PV1 = 3.30 | PV1 = 2.17 | PV1 ≥5.00 | PV1 = 2.33 | PV1 = 3.00 |
| ASTM 1053 (log10 reduction) | — | — | — | — | — | — |
| AOAC Germicidal Spray | — | — | — | — | — | — |
| EN 13697 (log10 reduction) | — | — | Sa ≥6.75 Ec ≥6.06 Pa ≥5.41 Eh ≥6.66 | — | — | — |
| EN 13697 T. ment (log10 reduction) | — | — | ≥4.61 | — | — | — |

|  | E148 | E149 | E150 | E151 | E152 | E153 | E154 |
|---|---|---|---|---|---|---|---|
| zinc citrate•3H$_2$O | — | 0.05 | — | — | — | — | — |
| zinc sulfate•7H$_2$O | 0.04 | — | 0.08 | 0.08 | 0.08 | 0.08 | 0.08 |
| zinc chloride | — | — | — | — | — | — | — |
| ethanol (100%) | 40.0 | 40.0 | 40.0 | 40.0 | 40.0 | 40.0 | 40.0 |
| BTC-65 (50%) | — | 0.20 | — | — | — | — | — |
| Onyxide 3300 (33%) | 0.30 | — | 0.300 | 0.30 | 0.15 | 0.15 | 0.30 |
| Neodol 91-6 | 0.10 | 0.10 | 0.10 | 0.10 | 0.10 | 0.10 | 0.10 |
| monoethanolamine | 0.10 | — | 0.008 | 0.015 | 0.06 | 0.80 | 0.70 |
| triethanolamine | 0.10 | 0.27 | 0.10 | 0.10 | 0.10 | 0.10 | 0.10 |
| sodium citrate•2H$_2$O | 0.10 | — | 0.20 | 0.20 | 0.10 | 0.10 | 0.20 |
| Citrasol 502 (50%) | 0.12 | 0.06 | 0.015 | — | 0.05 | 0.05 | — |
| NH4OH (29.86%) | — | — | — | — | — | 0.08 | 0.15 |
| NaOH (10%) | — | — | — | — | — | — | — |
| Triton BX | — | — | — | — | — | — | — |
| Monacor BE | — | — | — | — | — | — | — |
| Silwet Hydrostable | — | — | — | — | — | — | — |
| fragrance | — | — | — | — | — | — | — |
| di H$_2$O | q.s. | q.s. | q.s. | q.s. | q.s. | q.s. | q.s. |
| pH | 9.17 | 7.89 | 8.52 | 9.13 | 9.05 | 10.73 | 11.0 |
| zinc ions (ppm) | 91 | 155 | 182 | 182 | 182 | 182 | 182 |
| ASTM E 1052 (log10 reduction) | PV1 = 2.83 | PV1 = 1.83 | PV1 = 2.50 | PV1 = 2.83 | PV1 = 3.00 | PV1 ≥6.00 | PV1 ≥5.00 |
| ASTM 1053 (log10 reduction) | — | — | — | — | — | — | — |
| AOAC Germicidal Spray | — | — | — | — | — | — | — |
| EN 13697 (log10 reduction) | — | — | Sa ≥6.75 Ec ≥6.06 Pa ≥5.41 Eh ≥6.66 | — | — | — | — |
| EN 13697 T. ment (log10 reduction) | — | — | ≥4.61 | — | — | — | — |

|  | E155 | E156 | E157 | E158 | E159 | E160 | E161 | E162 |
|---|---|---|---|---|---|---|---|---|
| zinc citrate•3H$_2$O | 0.10 | 0.10 | — | — | — | — | — | 0.15 |
| zinc sulfate•7H$_2$O | — | — | 0.115 | 0.115 | 0.115 | 0.12 | 0.12 | — |
| zinc chloride | — | — | — | — | — | — | — | — |
| ethanol (100%) | 40.0 | 40.0 | 40.0 | 40.0 | 40.0 | 40.0 | 43.0 | 40.0 |
| BTC-65 (50%) | 0.40 | 0.40 | — | — | — | — | — | 0.20 |
| Onyxide 3300 (33%) | — | — | 0.303 | 0.91 | 0.30 | 0.30 | 0.303 | — |
| Neodol 91-6 | 0.10 | 0.10 | 0.10 | 0.10 | 0.10 | 0.10 | 0.10 | 0.10 |
| monoethanolamine | — | — | — | 0.21 | 0.41 | 0.04 | — | — |
| triethanolamine | 0.34 | 0.38 | 0.72 | 0.38 | 0.38 | 0.10 | 0.15 | 0.38 |
| sodium citrate•2H$_2$O | — | — | — | — | — | 0.20 | 0.20 | — |
| Citrasol 502 (50%) | 0.07 | 0.07 | 0.15 | 0.19 | 0.19 | — | 0.02 | 0.08 |
| NH4OH (29.86%) | — | 0.15 | — | 0.08 | 0.07 | — | 0.12 | — |
| NaOH (10%) | — | 0.45 | — | 0.25 | 0.42 | — | — | — |
| Triton BX | — | — | — | — | — | — | — | — |
| Monacor BE | — | — | — | — | — | — | — | — |
| Silwet Hydrostable | — | — | — | — | — | — | — | — |
| fragrance | — | — | — | — | — | — | — | — |
| di H$_2$O | q.s. | q.s. | q.s. | q.s. | q.s. | q.s. | q.s. | q.s. |
| pH | 7.92 | 11.02 | 7.92 | 9.72 | 10.35 | 9.10 | 9.46 | 7.89 |
| zinc ions (ppm) | 310 | 310 | 261 | 261 | 261 | 272.8 | 272.8 | 465 |
| ASTM E 1052 (log10 reduction) | PV1 = 2.00 | PV1 ≥5.00 | PV1 = 2.50 | PV1 ≥4.73 | PV1 ≥5.00 | PV1 = 2.17 | PV1 = 3.92 | PV1 = 2.00 |
| ASTM 1053 (log10 reduction) | — | — | — | — | — | — | — | — |
| AOAC Germicidal Spray | — | — | — | — | — | — | — | — |
| EN 13697 (log10 reduction) | — | — | — | — | — | — | — | — |
| EN 13697 T. ment (log10 reduction) | — | — | — | — | — | — | — | — |

TABLE 1-continued

|  | E163 | E164 | E165 | E166 | E167 | E168 | E169 | E170 |
|---|---|---|---|---|---|---|---|---|
| zinc citrate•3H$_2$O | 0.10 | 0.10 | — | — | — | — | — | 0.15 |
| zinc sulfate•7H$_2$O | — | — | 0.115 | 0.115 | 0.115 | 0.12 | 0.12 | — |
| zinc chloride | — | — | — | — | — | — | — | — |
| ethanol (100%) | 40.0 | 40.0 | 40.0 | 40.0 | 40.0 | 40.0 | 43.0 | 40.0 |
| BTC-65 (50%) | 0.40 | 0.40 | — | — | — | — | — | 0.20 |
| Onyxide 3300 (33%) | — | — | 0.303 | 0.91 | 0.30 | 0.30 | 0.303 | — |
| Neodol 91-6 | 0.10 | 0.10 | 0.10 | 0.10 | 0.10 | 0.10 | 0.10 | 0.10 |
| monoethanolamine | — | — | — | 0.21 | 0.41 | 0.04 | — | — |
| triethanolamine | 0.34 | 0.38 | 0.72 | 0.38 | 0.38 | 0.10 | 0.15 | 0.38 |
| sodium citrate•2H$_2$O | — | — | — | — | — | 0.20 | 0.20 | — |
| Citrasol 502 (50%) | 0.07 | 0.07 | 0.15 | 0.19 | 0.19 | — | 0.02 | 0.08 |
| NH4OH (29.86%) | — | 0.15 | — | 0.08 | 0.07 | — | 0.12 | — |
| NaOH (10%) | — | 0.45 | — | 0.25 | 0.42 | — | — | — |
| Triton BX | — | — | — | — | — | — | — | — |
| Monacor BE | — | — | — | — | — | — | — | — |
| Silwet Hydrostable | — | — | — | — | — | — | — | — |
| fragrance | — | — | — | — | — | — | — | — |
| di H$_2$O | q.s. | q.s. | q.s. | q.s. | q.s. | q.s. | q.s. | q.s. |
| pH | 7.92 | 11.02 | 7.92 | 9.72 | 10.35 | 9.10 | 9.46 | 7.89 |
| zinc ions (ppm) | 310 | 310 | 261 | 261 | 261 | 272.8 | 272.8 | 465 |
| ASTM E 1052 (log10 reduction) | PV1 = 2.00 | PV1 ≥5.00 | PV1 = 2.50 | PV1 ≥4.73 | PV1 ≥5.00 | PV1 = 2.17 | PV1 = 3.92 | PV1 = 2.00 |
| ASTM 1053 (log10 reduction) | — | — | — | — | — | — | — | — |
| AOAC Germicidal Spray | — | — | — | — | — | — | — | — |
| EN 13697 (log10 reduction) | — | — | — | — | — | — | — | — |
| EN 13697 T. ment (log10 reduction) | — | — | — | — | — | — | — | — |

|  | E170B | E170C | E171 | E172 | E173 | E173B | E174 | E175 |
|---|---|---|---|---|---|---|---|---|
| zinc acetate | 0.08 | 0.08 | 0.08 | 0.08 | 0.08 | 0.08 | 0.08 | 0.08 |
| zinc sulfate•7H$_2$O | — | — | — | — | — | — | — | — |
| zinc chloride | — | — | — | — | — | — | — | — |
| ethanol (100%) | 45.0 | 45.0 | 45.0 | 45.0 | 45.0 | 45.0 | 45.0 | 45.0 |
| BTC-65 (50%) | — | — | 0.20 | — | — | 0.20 | 0.20 | — |
| Onyxide 3300 (33%) | 0.303 | 0.303 | — | 0.303 | 0.303 | — | 0.10 | 0.303 |
| Neodol 91-6 | 0.10 | 0.10 | 0.10 | 0.10 | 0.10 | 0.10 | 0.10 | 0.10 |
| monoethanolamine | — | — | — | 0.11 | 0.11 | — | 0.75 | — |
| triethanolamine | 0.22 | 0.295 | 0.22 | 0.22 | 0.22 | 0.335 | 0.07 | 0.27 |
| sodium citrate•2H2O | — | — | — | — | — | — | 0.20 | — |
| Citrasol 502 (50%) | 0.145 | 0.13 | 0.21 | 0.155 | 0.14 | — | — | 0.14 |
| NH4OH (29.86%) | 0.15 | 0.26 | 0.14 | 0.124 | 0.124 | — | 0.17 | — |
| NaOH (10%) | — | — | — | — | — | — | — | — |
| Triton BX | — | — | — | — | — | 0.26 | — | — |
| Monacor BE | 0.06 | — | — | — | 0.08 | — | — | — |
| Silwet Hydrostable | — | — | — | — | — | — | — | — |
| fragrance | — | — | — | — | — | — | — | — |
| di H$_2$O | q.s. | q.s. | q.s. | q.s. | q.s. | q.s. | q.s. | q.s. |
| pH | 9.25 | 9.45 | 8.56 | 9.63 | 9.24 | 8.6 | 10.78 | 7.08 |
| zinc ions (ppm) | 285 | 285 | 285 | 285 | 285 | 285 | 285 | 285 |
| ASTM E 1052 (log10 reduction) | PV1 ≥5.00 | PV1 = 4.50 | PV1 = 3.83 | PV1 ≥4.50 | PV1 ≥4.50 | PV1 ≥5.50 | PV1 ≥5.00 | PV1 = 3.17 |
| ASTM 1053 (log10 reduction) | — | — | — | — | — | — | — | — |
| AOAC Germicidal Spray | Sa = 0/30 Pa = 0/30 | — | — | — | — | — | — | — |
| EN 13697 (log10 reduction) | Sa ≥6.75 Ec ≥6.06 Pa ≥5.41 Eh ≥6.66 | — | Sa ≥6.75 Ec = 4.98 Pa ≥5.41 Eh ≥6.66 | — | — | — | — | — |
| EN 13697 T. ment (log10 reduction) | ≥4.61 | — | ≥4.61 | — | — | — | — | — |

|  | E176 | E177 | E178A | E178B | E178C | E179 |
|---|---|---|---|---|---|---|
| zinc acetate | — | — | — | — | — | — |
| zinc sulfate•7H$_2$O | 0.10 | 0.10 | 0.115 | — | — | 0.115 |
| zinc chloride | — | — | — | 0.055 | 0.055 | — |
| ethanol (100%) | 55.0 | 70.0 | 45.0 | 45.0 | 45.0 | 45.0 |
| BTC-65 (50%) | 0.20 | — | — | — | — | — |
| Onyxide 3300 (33%) | — | 0.30 | 0.303 | 0.303 | 0.303 | 0.30 |
| Neodol 91-6 | 0.10 | 0.10 | 0.10 | 0.10 | 0.10 | 0.10 |
| monoethanolamine | 0.075 | 0.15 | — | — | — | — |
| triethanolamine | 0.10 | 0.10 | 0.35 | 0.38 | 0.38 | 0.40 |
| sodium citrate | 0.10 | 0.08 | — | — | — | — |
| Citrasol 502 (50%) | 0.06 | 0.20 | 0.14 | 0.15 | 0.12 | 0.19 |
| NH4OH (29.86%) | — | — | 0.09 | 0.30 | 0.30 | 0.13 |
| NaOH (10%) | — | — | — | — | — | — |
| Triton BX | — | — | — | — | — | — |
| Monacor BE | — | — | — | — | 0.10 | 0.20 |
| Silwet Hydrostable | — | — | — | — | — | — |

TABLE 1-continued

|  | | | | | | |
|---|---|---|---|---|---|---|
| fragrance | — | — | — | — | — | — |
| di H$_2$O | q.s. | q.s. | q.s. | q.s. | q.s. | q.s. |
| pH | 9.03 | 9.2 | 8.12 | 8.34 | 9.27 | 9.5 |
| zinc ions (ppm) | 227.4 | 227.4 | 261 | 263.8 | 263.8 | 261 |
| ASTM E 1052 (log10 reduction) | PV1 = 4.17 | PV1 ≥6.00 | PV1 = 1.50 | PV1 = 2.27 | PV1 ≥4.73 | PV1 ≥4.73 |
| ASTM 1053 (log10 reduction) | — | — | — | — | — | — |
| AOAC Germicidal Spray | — | — | — | — | — | — |
| EN 13697 (log10 reduction) | — | — | — | — | — | — |
| EN 13697 T. ment (log10 reduction) | — | — | — | — | — | — |

|  | E180 | E181 | E182 | E183 | E184 | E185 | E186 |
|---|---|---|---|---|---|---|---|
| zinc acetate | — | — | — | — | — | — | — |
| zinc sulfate•7H$_2$O | 0.13 | 0.13 | 0.13 | 0.13 | 0.13 | 0.13 | 0.13 |
| zinc chloride | — | — | — | — | — | — | — |
| ethanol (100%) | 43.0 | 43.0 | 43.0 | 43.0 | 43.0 | 43.0 | 43.0 |
| BTC-65 (50%) | — | — | — | — | — | — | — |
| Onyxide 3300 (33%) | 0.33 | 0.33 | 0.33 | 0.33 | 0.33 | 0.33 | 0.33 |
| Neodol 91-6 | 0.10 | 0.10 | 0.10 | 0.10 | 0.10 | 0.10 | 0.10 |
| monoethanolamine | 1.04 | 1.04 | 1.04 | 1.04 | 1.04 | 1.04 | 1.04 |
| triethanolamine | 0.10 | 0.10 | 0.10 | 0.10 | 0.10 | 0.10 | 0.10 |
| sodium citrate | — | — | — | — | — | — | — |
| Citrasol 502 (50%) | 0.12 | 0.12 | 0.12 | 0.12 | 0.12 | 0.12 | 0.12 |
| NH4OH (29.86%) | 0.10 | 0.10 | 0.10 | 0.10 | 0.10 | 0.10 | 0.10 |
| NaOH (10%) | — | — | — | — | — | — | — |
| Triton BX | — | — | — | — | — | — | — |
| Monacor BE | 0.065 | 0.10 | 0.15 | 0.25 | — | — | — |
| sodium benzoate | — | — | — | — | 0.06 | 0.10 | 0.15 |
| Silwet Hydrostable | — | — | — | — | — | — | — |
| fragrance | — | — | — | — | — | — | — |
| di H$_2$O | q.s. | q.s. | q.s. | q.s. | q.s. | q.s. | q.s. |
| pH | 10.55 | 10.54 | 10.52 | 10.45 | 10.58 | 10.55 | 10.51 |
| zinc ions (ppm) | — | — | — | — | — | — | — |
| ASTM E 1052 (log10 reduction) | PV1 ≥7.00 | PV1 ≥7.00 | PV1 ≥7.00 | PV1 ≥7.00 | PV1 ≥7.00 | PV1 ≥7.00 | PV1 ≥7.00 |
| ASTM 1053 (log10 reduction) | — | — | — | — | — | — | — |
| AOAC Germicidal Spray | — | — | — | — | — | — | — |
| EN 13697 (log10 reduction) | — | — | — | — | — | — | — |
| EN 13697 T. ment (log10 reduction) | — | — | — | — | — | — | — |

|  | E187 | E188 | E189 | E190 | E191 | E192 |
|---|---|---|---|---|---|---|
| zinc acetate | — | — | — | — | — | — |
| zinc sulfate•7H$_2$O | 0.14 | 0.14 | 0.14 | 0.14 | 0.14 | 0.14 |
| zinc chloride | — | — | — | — | — | — |
| ethanol (100%) | 49.77 | 49.77 | 49.77 | 49.77 | 49.77 | 49.77 |
| BTC-65 (50%) | — | — | — | — | — | — |
| Onyxide 3300 (33%) | 0.337 | 0.337 | 0.337 | 0.337 | 0.337 | 0.337 |
| Neodol 91-6 | — | — | — | — | — | — |
| monoethanolamine | — | 0.01 | — | 0.34 | 1.4 | 4.92 |
| triethanolamine | 0.1 | 0.1 | 0.1 | 0.1 | 0.1 | 0.1 |
| sodium citrate•2H$_2$O | — | — | — | — | — | — |
| Citrasol 502 (50%) | 0.27 | 0.18 | 0.12 | 0.12 | 0.12 | 0.12 |
| NH4(OH) (29.86%) | 0.1 | 0.1 | 0.1 | 0.1 | 0.1 | 0.1 |
| NaOH (10%) | — | — | — | — | — | — |
| Triton BX | — | — | — | — | — | — |
| Monacor BE | 0.15 | 0.15 | 0.15 | 0.15 | 0.15 | 0.15 |
| Crodasol WS | 0.15 | 0.15 | 0.15 | 0.15 | 0.15 | 0.15 |
| fragrance | — | — | — | — | — | — |
| di H$_2$O | q.s. | q.s. | q.s. | q.s. | q.s. | q.s. |
| pH | 9.0 | 9.25 | 9.50 | 10.0 | 10.51 | 11.03 |
| zinc ions (ppm) | 318.33 | 318.33 | 318.33 | 318.33 | 318.33 | 318.33 |
| can type | S | S | S | S | S | S |
| ASTM 1053 (log10 reduction), 30 seconds contact time | PV1 = 2.56 | PV1 = 2.9 | PV1 = 3.73 | PV1 = 4.56 | PV1 ≥4.73 | PV1 ≥4.73 |
| ASTM 1053 (log10 reduction), 5 minute contact time | PV1 = 3.56 | PV1 = 3.73 | PV1 ≥4.73 | PV1 = 4.56 | PV1 ≥4.73 | PV1 ≥4.73 |

To each of examples E187 through E192 was added an additional amount of 10% wt. of AB46 (based on the total weight of the example composition's constituents, which totaled 100% wt.) as the propellant constituent, and the reported microbicidal testing was performed utilizing the recovered liquid collected immediately after a quantity of the pressurized composition was dispensed from an aerosol canister

|  | E193 | E194 | E195 | E196 | E197 | E198 | E199 | E200 |
|---|---|---|---|---|---|---|---|---|
| zinc acetate | — | — | — | — | — | — | — | — |
| zinc sulfate•7H$_2$O | 0.14 | 0.14 | 0.14 | 0.14 | 0.14 | 0.14 | 0.14 | 0.14 |
| zinc chloride | — | — | — | — | — | — | — | — |
| ethanol (100%) | 35.0 | 35.0 | 35.0 | 35.0 | 40.0 | 40.0 | 40.0 | 40.0 |
| BTC-65 (50%) | — | — | — | — | — | — | — | — |
| Onyxide 3300 (33%) | — | — | — | — | — | — | — | — |

TABLE 1-continued

| | | | | | | | | |
|---|---|---|---|---|---|---|---|---|
| Neodol 91-6 | 0.1 | 0.1 | 0.1 | 0.1 | 0.1 | 0.1 | 0.1 | 0.1 |
| monoethanolamine | — | — | — | — | 0.07 | 0.07 | 0.07 | 0.07 |
| triethanolamine | 0.07 | 0.07 | 0.07 | 0.07 | 0.1 | 0.1 | 0.1 | 0.1 |
| sodium citrate | 0.2 | 0.2 | 0.2 | 0.2 | 0.1 | 0.1 | 0.1 | 0.1 |
| Citrasol 502 (50%) | — | — | — | — | 0.05 | 0.05 | 0.05 | 0.05 |
| NH4OH (29.86%) | 0.07 | 0.07 | 0.07 | 0.07 | — | — | — | — |
| NaOH (10%) | 0.07 | 0.13 | 0.16 | 0.18 | 0.06 | 0.17 | 0.25 | 0.32 |
| Triton BX | — | — | — | — | — | — | — | — |
| Monacor BE | — | — | — | — | — | — | — | — |
| sodium benzoate | — | — | — | — | — | — | — | — |
| Silwet Hydrostable | — | — | — | — | — | — | — | — |
| fragrance | — | — | — | — | — | — | — | — |
| di H$_2$O | q.s. | q.s. | q.s. | q.s. | q.s. | q.s. | q.s. | q.s. |
| pH | 9.99 | 10.51 | 11.04 | 11.5 | 9.46 | 9.98 | 10.5 | 11.51 |
| zinc ions (ppm) | 318.33 | 318.33 | 318.33 | 318.33 | 318.33 | 318.33 | 318.33 | 318.33 |
| ASTM E1053 (log10 reduction) | — | — | PV1 = 4.44 | PV1 = 4.83 | — | — | PV1 = 3.17 | PV1 = 4.17 |

To each of comparative examples E193 through E200 was added an additional amount of 10% wt. of AB46 (based on the total weight of the example composition's constituents, which totaled 100% wt.) as the propellant constituent, and the reported microbicidal testing was performed utilizing the recovered liquid collected immediately after a quantity of the pressurized composition was dispensed from an aerosol canister

| | E201 | E202 | E203 | E204 | E205 | E206 | E207 | E208 | E209 |
|---|---|---|---|---|---|---|---|---|---|
| zinc acetate | — | — | — | — | — | — | — | — | — |
| zinc sulfate•7H$_2$O | 0.14 | 0.14 | 0.14 | 0.14 | 0.14 | 0.14 | 0.14 | 0.14 | 0.14 |
| zinc chloride | — | — | — | — | — | — | — | — | — |
| ethanol (100%) | 42.5 | 42.5 | 42.5 | 42.5 | 42.5 | 45.0 | 45.0 | 45.0 | 45.0 |
| BTC-65 (50%) | — | — | — | — | — | — | — | — | — |
| Onyxide 3300 (33%) | — | — | — | — | — | — | — | — | — |
| Neodol 91-6 | 0.1 | 0.1 | 0.1 | 0.1 | 0.1 | 0.1 | 0.1 | 0.1 | 0.1 |
| monoethanolamine | — | — | — | — | — | 0.2 | 0.2 | 0.2 | 0.2 |
| triethanolamine | 0.15 | 0.15 | 0.15 | 0.15 | 0.15 | 0.27 | 0.27 | 0.27 | 0.27 |
| sodium citrate | — | — | — | — | — | — | — | — | — |
| Citrasol 502 (50%) | 0.2 | 0.02 | 0.02 | 0.02 | 0.02 | 0.65 | 0.29 | 0.14 | 0.14 |
| NH4OH (29.86%) | 0.12 | 0.12 | 0.12 | 0.12 | 0.12 | 0.12 | 0.12 | 0.12 | 0.12 |
| NaOH (10%) | 0.06 | 0.04 | 0.22 | 0.37 | 0.5 | — | — | 0.32 | 0.47 |
| Triton BX | — | — | — | — | — | — | — | — | — |
| Monacor BE | — | — | — | — | — | — | — | — | — |
| sodium benzoate | — | — | — | — | — | — | — | — | — |
| Silwet Hydrostable | — | — | — | — | — | — | — | — | — |
| fragrance | — | — | — | — | — | — | — | — | — |
| di H$_2$O | q.s. | q.s. | q.s. | q.s. | q.s. | q.s. | q.s. | q.s. | q.s. |
| pH | 8.49 | 9.5 | 10.0 | 10.5 | 11.5 | 8.51 | 9.53 | 10.46 | 10.98 |
| zinc ions (ppm) | 318.33 | 318.33 | 318.33 | 318.33 | 318.33 | 318.33 | 318.33 | 318.33 | 318.33 |
| ASTM E1053 (log10 reduction) | — | — | PV1 = 5.0 | PV1 ≥5.17 | PV1 ≥5.17 | — | — | PV1 ≥5.17 | PV1 ≥5.17 |

To each of comparative examples E201 through E209 was added an additional amount canister of 10% wt. of AB46 (based on the total weight of the example composition's constituents, which totaled 100% wt.) as the propellant constituent, and the reported microbicidal testing was performed utilizing the recovered liquid collected immediately after a quantity of the pressurized composition was dispensed from an aerosol

TABLE 2

(Example Compositions)

| | E210 | E211 | E212 | E213 | E214 | E215 | E216 |
|---|---|---|---|---|---|---|---|
| zinc acetate | — | — | — | — | — | — | — |
| zinc sulfate•7H$_2$O | 0.12 | 0.116 | 0.116 | 0.116 | 0.12 | 0.12 | 0.12 |
| zinc chloride | — | — | — | — | — | — | — |
| ethanol (100%) | 33.95 | 38.8 | 38.8 | 43.65 | 37.20 | 37.20 | 37.20 |
| BTC-65 (50%) | — | — | — | — | — | — | — |
| Onyxide 3300 (33%) | 0.30 | 0.29 | 0.29 | 0.29 | 0.30 | 0.30 | 0.30 |
| Neodol 91-6 | 0.093 | 0.09 | 0.09 | 0.09 | 0.093 | 0.093 | 0.093 |
| monoethanolamine | — | — | 0.25 | — | 0.13 | 0.44 | 0.837 |
| triethanolamine | 0.13 | 0.12 | 0.12 | 0.12 | 0.093 | 0.093 | 0.093 |
| sodium citrate•2H$_2$O | 0.18 | 0.18 | 0.18 | 0.18 | — | — | — |
| Citrasol 502 (50%) | — | — | — | — | 0.093 | 0.093 | 0.093 |
| NH4OH (29.86%) | 0.081 | 0.081 | 0.14 | 0.063 | 0.11 | 0.11 | 0.11 |
| NaOH (10%) | — | — | — | — | — | — | — |
| Triton BX | — | — | — | — | — | — | — |
| Monacor BE | — | — | — | — | — | — | — |
| Silwet Hydrostable | — | — | — | — | — | — | — |
| fragrance | — | — | — | — | — | — | — |
| propellant | 7.0 | 7.0 | 7.0 | 7.0 | 7.0 | 7.0 | 7.0 |
| di H$_2$O | q.s. | q.s. | q.s. | q.s. | q.s. | q.s. | q.s. |
| pH | 9.11 | 9.17 | 10.44 | 9.18 | 9.45 | 9.98 | 10.37 |
| zinc ions (ppm) | 272.8 | 272.8 | 272.8 | 272.8 | 272.8 | 272.8 | 272.8 |
| can type | W | W | W | W | W | W | W |
| ASTM E 1052 (log10 reduction) | PV1 = 1.73 | PV1 = 3.27 | PV1 ≥5.00 | PV1 ≥5.00 | — | PV1 ≥5.00 | — |

TABLE 2-continued (Example Compositions)

| | | | | | | | |
|---|---|---|---|---|---|---|---|
| ASTM 1053 (log10 reduction) | PV1 = 0.00 | PV1 = 0.38 | PV1 ≥2.25 | PV1 = 2.00 | PV1 = 2.28 | PV1 ≥4.25 | PV1 ≥4.50 |
| AOAC Germicidal Spray | — | — | — | — | — | — | — |
| EN 13697 (log10 reduction) | — | — | — | — | — | — | — |
| EN 13697 T. ment (log10 reduction) | — | — | — | — | — | — | — |

| | E217 | E218 | E219 | E220 | E221 | E222 | E223 | E224 | E225 |
|---|---|---|---|---|---|---|---|---|---|
| zinc acetate | — | — | — | — | — | — | — | — | — |
| zinc sulfate•7H$_2$O | 0.12 | 0.12 | 0.12 | 0.12 | 0.12 | 0.12 | 0.12 | 0.12 | 0.12 |
| zinc chloride | — | — | — | — | — | — | — | — | — |
| ethanol (100%) | 39.06 | 39.06 | 39.06 | 39.06 | 41.85 | 41.85 | 41.85 | 40.0 | 39.81 |
| BTC-65 (50%) | — | — | — | — | — | — | — | — | — |
| Onyxide 3300 (33%) | 0.30 | 0.30 | 0.30 | 0.30 | 0.30 | 0.30 | 0.30 | 0.30 | 0.30 |
| Neodol 91-6 | 0.093 | 0.093 | 0.093 | 0.093 | 0.093 | 0.093 | 0.093 | 0.093 | 0.093 |
| monoethanolamine | 0.13 | 0.44 | 0.065 | 0.809 | 0.186 | 0.502 | 0.818 | 0.931 | 0.26 |
| triethanolamine | 0.093 | 0.093 | 0.093 | 0.093 | 0.093 | 0.093 | 0.093 | 0.093 | 0.12 |
| sodium citrate•2H$_2$O | — | — | 0.186 | — | — | — | — | — | — |
| Citrasol 502 (50%) | 0.11 | 0.11 | — | 0.11 | 0.11 | 0.11 | 0.11 | 0.12 | — |
| NH4OH (29.86%) | 0.11 | 0.11 | 0.11 | 0.11 | 0.102 | 0.093 | 0.093 | 0.093 | 0.15 |
| NaOH (10%) | — | — | — | — | — | — | — | — | — |
| Triton BX | — | — | — | — | — | — | — | — | — |
| Monacor BE | — | — | — | — | — | — | — | — | — |
| Silwet Hydrostable | — | — | — | — | — | — | — | — | 0.10 |
| fragrance | — | — | — | — | — | — | — | — | — |
| propellant | 7.0 | 7.0 | 7.0 | 7.0 | 7.0 | 7.0 | 7.0 | 7.0 | 7.0 |
| di H$_2$O | q.s. | q.s. | q.s. | q.s. | q.s. | q.s. | q.s. | q.s | q.s. |
| pH | 9.40 | 9.95 | 10.13 | 10.38 | 9.33 | 9.98 | 10.25 | 10.50 | 10.50 |
| zinc ions (ppm) | 272.8 | 272.8 | 272.8 | 272.8 | 272.8 | 272.8 | 272.8 | 272.8 | 272.8 |
| can type | W | W | W | W | W | W | W | S | E |
| ASTM E 1052 (log10 reduction) | PV1 ≥5.00 | PV1 ≥5.00 | PV1 ≥5.00 | PV1 ≥5.00 | — | — | — | PV1 ≥7.00 | PV1 ≥7.00 |
| ASTM 1053 (log10 reduction) | PV1 = 4.75 | PV1 ≥5.00 | PV1 = 4.00 | PV1 ≥4.42 | PV1 = 3.05 | PV1 = 4.58 | PV1 ≥5.00 | PV1 ≥5.00 (10 min) | PV1 ≥4.5 (10 min) |
| AOAC Germicidal Spray | — | — | — | — | — | — | — | — | — |
| EN 13697 (log10 reduction) | — | — | — | — | — | — | — | — | — |
| EN 13697 T. ment (log10 reduction) | — | — | — | — | — | — | — | — | — |

| | E226 | E227 | E228 | E229 | E230 | E231 | E232 |
|---|---|---|---|---|---|---|---|
| zinc acetate | — | — | — | — | — | — | — |
| zinc sulfate•7H$_2$O | 0.126 | 0.126 | 0.0099 | 0.0198 | 0.198 | 0.3869 | 3.969 |
| zinc chloride | — | — | — | — | — | — | — |
| ethanol (100%) | 42.80 | 42.797 | 42.797 | 42.797 | 42.797 | 42.797 | 42.797 |
| BTC-65 (50%) | — | — | — | — | — | — | — |
| Onyxide 3300 (33%) | 0.303 | 0.303 | 0.303 | 0.303 | 0.303 | 0.303 | 0.303 |
| Neodol 91-6 | — | — | — | — | — | — | — |
| Crodasol WS | 0.135 | 0.135 | 0.135 | 0.135 | 0.135 | 0.135 | 0.135 |
| monoethanolamine | 0.936 | 0.936 | 0.936 | 0.936 | 1.362 | 2.382 | 11.937 |
| triethanolamine | 0.09 | 0.09 | 0.09 | 0.09 | 0.09 | 0.09 | 0.09 |
| citric acid (anhy.) | 0.054 | 0.10 | 0.008 | 0.015 | 0.157 | 0.315 | 3.15 |
| sodium citrate•2H$_2$O | — | — | — | — | — | — | — |
| Citrasol 502 (50%) | — | — | — | — | — | — | — |
| NH4OH (29.86%) | 0.09 | 0.09 | 0.09 | 0.09 | 0.09 | 0.09 | 0.09 |
| NaOH (10%) | — | — | — | — | — | — | — |
| Triton BX | — | — | — | — | — | — | — |
| Monacor BE | 0.135 | 0.135 | 0.135 | 0.135 | 0.135 | 0.135 | 0.135 |
| Silwet Hydrostable | — | — | — | — | — | — | — |
| fragrance | 0.218 | 0.218 | — | — | — | — | — |
| propellant | 10.0 | 10.0 | 10.0 | 10.0 | 10.0 | 10.0 | 10.0 |
| di H$_2$O | q.s. | q.s. | q.s. | q.s. | q.s. | q.s. | q.s. |
| pH | 10.50 | 10.45 | 10.73 | 10.66 | 10.26 | 10.54 | 10.08 |
| zinc ions (ppm) | 286 | 286 | 22.5 | 45 | 450 | 900 | 9000 |
| can type | S | S | S | S | S | S | S |
| ASTM E 1052 (log10 reduction) | — | — | — | — | — | — | — |
| ASTM 1053 (log10 reduction) | PV1 ≥4.75 | PV1 ≥4.25 | PV1 ≥5.83 | PV1 ≥5.83 | PV1 ≥5.83 | PV1 ≥5.83 | PV1 ≥5.83 |
| AOAC Germicidal Spray, 5 minute contact time | Sa = 0/60 Pa = 0/60 | — | — | — | — | — | — |
| EN 13697 (log10 reduction) | — | — | — | — | — | — | — |
| EN 13697 T. ment (log10 reduction) | — | — | — | — | — | — | — |

TABLE 2-continued (Example Compositions)

|  | E233 | E234 | E235 | E236 | E237 | E238 | E239 | E240 |
|---|---|---|---|---|---|---|---|---|
| zinc acetate | — | — | — | — | — | — | — | — |
| zinc sulfate•7H$_2$O | 0.0003969 | 0.00198 | 0.00396 | 0.00594 | 0.00792 | 0.126 | 0.126 | 0.126 |
| zinc chloride | — | — | — | — | — | — | — | — |
| ethanol (100%) | 42.797 | 42.797 | 42.797 | 42.797 | 42.797 | 49.797 | 46.797 | 42.797 |
| BTC-65 (50%) | — | — | — | — | — | — | — | — |
| Onyxide 3300 (33%) | 0.303 | 0.303 | 0.303 | 0.303 | 0.303 | 0.303 | 0.303 | 0.303 |
| Neodol 91-6 | — | — | — | — | — | — | — | — |
| Crodasol WS | 0.135 | 0.135 | 0.135 | 0.135 | 0.135 | 0.135 | 0.135 | 0.135 |
| monoethanolamine | 0.950 | 1.073 | 1.026 | 1.284 | 1.233 | 1.47 | 0.936 | 0.936 |
| triethanolamine | 0.090 | 0.090 | 0.090 | 0.090 | 0.090 | 0.090 | 0.090 | 0.090 |
| citric acid (anhy.) | 0.100 | 0.100 | 0.100 | 0.100 | 0.100 | 0.100 | 0.100 | 0.100 |
| sodium citrate•2H$_2$O | — | — | — | — | — | — | — | — |
| Citrasol 502 (50%) | — | — | — | — | — | — | — | — |
| NH4OH (29.86%) | 0.09 | 0.09 | 0.09 | 0.09 | 0.09 | 0.09 | 0.09 | 0.09 |
| NaOH (10%) | — | — | — | — | — | — | — | — |
| Triton BX | — | — | — | — | — | — | — | — |
| Monacor BE | 0.135 | 0.135 | 0.135 | 0.135 | 0.135 | 0.135 | 0.135 | 0.135 |
| Silwet Hydrostable | — | — | — | — | — | — | — | — |
| fragrance | — | — | — | — | — | 0.225 | 0.225 | 0.218 |
| propellant | 10.0 | 10.0 | 10.0 | 10.0 | 10.0 | 10.0 | 10.0 | 10.0 |
| di H$_2$O | q.s. | q.s. | q.s. | q.s. | q.s. | q.s. | q.s. | q.s. |
| pH | 10.47 | 10.52 | 10.45 | 10.53 | 10.43 | 10.68 | 10.43 | 10.45 |
| zinc ions (ppm) | 0.9 | 4.5 | 9 | 13.5 | 18 | 286 | 286 | 286 |
| can type | S | S | S | S | S | S | S | S |
| ASTM E 1052 (log10 reduction) | — | — | — | — | — | — | — | — |
| ASTM 1053 (log10 reduction) | PV1 = 2.9 | PV1 = 3.23 | PV1 = 3.23 | PV1 = 3.56 | PV1 = 4.23 | PV1 ≥4.27 | PV1 ≥4.27 | — |
| AOAC Germicidal Spray, 5 minute contact time | — | — | — | — | — | — | — | — |
| EN 13697 (log10 reduction) | — | — | — | — | — | — | — | — |
| EN 13697 T. ment (log10 reduction) | — | — | — | — | — | — | — | — |

Any of the compositions described on Table 1 described herein may also be formed into a pressurized surface treatment composition of the invention by the addition of a further, suitable amount of a propellant thereto. Examples of such pressurized compositions are disclosed in the compositions of Table 2. Particularly preferred forms of a pressurized animate surface treatment compositions are ones in which between about 80-99.5 parts by weight of a treatment composition indicated on Table 1, and identified with the prepended letter "E" (e.g. "E1", "E2" etc.) are combined with 0.5-20 parts by weight of suitable propellant or propellant composition, and the resultant blend or mixture is supplied to a sealable dispensing container, such as an aerosol canister which includes a valve which permits for the sprayable, pressurized treatment compositions to exit the container. Typically such a sealed dispensing container includes in addition to the valve, a valve stem upon which is mounted a conventional spray nozzle adapted to be compressed or tilted by a consumer in order to release the pressurized composition as an aerosol. For example, a quantity of a composition according to the invention as described on Table 1 is supplied to a suitable aerosol canister, to which is added, e.g., 7% vol. of a propellant composition and the aerosol canister is sealed. The sprayable treatment composition may be dispensed from the aerosol canister in a conventional manner and used to treat an inanimate surface.

Any of the foregoing compositions may be used as topical rinse composition, a hair rinse composition, whether in an unpressurized or pressurized (e.g., aerosol) product format.

Several of the compositions of Table 1 were also tested for product stability and performance after being stored for an extended period of time (4 weeks or more) at room temperature (approx. 20-22° C.) to determine the microbicidal efficacy of the compositions following storage. The results in the following Table 1A below demonstrate the continued microbicidal efficacy of compositions according to the invention.

TABLE 1A

|  | E8 | E2 | E22 |
|---|---|---|---|
| pH | 8.06 | 9.5 | 9.17 |
| ASTM E 1052, (log10 reduction) | at 4 months: PV1 => 4.73 at 6 months: PV1 => 4.56 FCV > 6.00 | at 3 months: PV1 > 5.50 | at 3 months: PV1 > 4.27 |

As can be seen from the foregoing results, the compositions of the invention exhibited excellent microbicidal efficacy as demonstrated by the various test results, even wherein reduced levels of ethanol (e.g, less than 50% wt, especially 45% wt.) or less ethanol) was present as a constituent.

Two of the foregoing example compositions were again tested after having been retained in a pressurized container for in excess of 12 months at room temperature (20° C.-22° C.), and thereafter tested for microbicidal efficacy. The formulations, the time interval for which they were stored at room temperature, and the test results following the indicated time interval (days) are reported on the following Table 3.

TABLE 2

(Pressurized Example Compositions, Long Term Stability Testing)

|  | E220 | E241 |
|---|---|---|
| zinc sulfate•7H$_2$O | 0.12 | 0.05 |
| ethanol (100%) | 39.06 | 40.0 |
| Onyxide 3300 (33%) | 0.30 | 0.28 |
| Neodol 91-6 | 0.093 | 0.09 |
| monoethanolamine | 0.809 | 0.79 |
| triethanolamine | 0.093 | 0.09 |
| Citrasol 502 (50%) | 0.11 | 0.11 |
| NH4OH (29.86%) | 0.11 | 0.09 |
| propellant | 7.0 | 7.0 |
| di H$_2$O | q.s. | q.s. |
| pH | 10.38 | 10.42 |
| zinc ions (ppm) | 272.8 | 182 |
| can type | W | S |
| days stored | 570 | 493 |
| ASTM 1053 (log10 reduction) 10 minute contact time, 'dirty' conditions | PV ≥ 4.27 | PV ≥ 4.27 |

As can be seen from the foregoing results the compositions of the invention exhibited excellent microbicidal efficacy as demonstrated by the various test results, even wherein reduced amounts of ethanol were present as a constituent.

Further comparative example compositions of the invention, several of which included 1% wt. or greater amounts (e.g, 5% wt. or more) of detersive surfactants are disclosed on the following further parts of Table 1 as set forth below. To each of the foregoing a minor amount of an acid, e.g, citric acid, or a base, e.g, NaOH, may have been added in order to achieve the indicated pH of the respective composition.

TABLE 1

|  | E242 | E243 |
|---|---|---|
| CuSO$_4$•5H$_2$O | 0.1 | 0.1 |
| ethanol (100%) | 5.0 | 5.0 |
| BTC-65 (50%) | 0.2 | 0.2 |
| decyl glucoside | 5.0 | 5.0 |
| di H$_2$O | q.s. | q.s. |
| pH | 5.8 | 8.34 |
| ASTM E 2315 (log10 reduction) at 1 minute contact time** | Sa = 1.27<br>Ec = 2.15 | Sa = 1.73<br>Ec = 1.69 |

|  | E244 | E245 | E246 | E247 |
|---|---|---|---|---|
| CuSO$_4$•5H$_2$O | — | — | 0.1 | 0.1 |
| ZnSO4•7H2O | 0.12 | 0.12 | — | — |
| ethanol (100%) | 15.0 | 15.0 | 15.0 | 15.0 |
| BTC-65 (50%) | 0.2 | 0.2 | 0.2 | 0.2 |
| decyl glucoside | 5.0 | 5.0 | 5.0 | 5.0 |
| BTC-65 (50%) | 0.2 | 0.2 | 0.2 | 0.2 |
| propylene glycol | 2.0 | 2.0 | 2.0 | 2.0 |
| Neutrol TA | as required | as required | as required | as required |
| Citrosol 502(50%) | as required | as required | as required | as required |
| di H$_2$O | q.s. | q.s. | q.s. | q.s. |
| pH | 5.12 | 8.83 | 4.91 | 8.98 |
| ASTM E 2315 (log10 reduction), 1 minute contact time** | Sa = 2.31<br>Ec = 2.73 | Sa = 5.27<br>Ec = 5.38 | Sa = 4.31<br>Ec = 5.38 | Sa = 3.01<br>Ec = 4.70 |

|  | E248 | E249 | E250 | E251 |
|---|---|---|---|---|
| CuSO$_4$•5H$_2$O | 0.1 | 0.1 | 0.1 | 0.1 |
| ethanol (100%) | 35.0 | 35.0 | 35.0 | 35.0 |
| BTC-65 (50%) | 0.2 | 0.2 | 0.2 | 0.2 |
| decyl glucoside | 1.0 | 1.0 | 5.0 | 5.0 |
| di H$_2$O | q.s. | q.s. | q.s. | q.s. |
| pH | 5.6 | 7.7 | 5.49 | 7.90 |
| ASTM E 2315 (log10 reduction) at 1 minute contact time* | Sa = 1.27<br>Ec = 2.15 | Sa = 1.73<br>Ec = 1.69 | Sa > 6.72<br>Ec > 6.49 | Sa > 6.72<br>Ec > 6.49 |

**reported results are averaged from two or more tests

The compositions from the foregoing table demonstrate highly effective compositions are attained with an ethanol content of even as little as 15% wt., with improved results obtained with an increased ethanol contents of 35% wt., and that in these compositions antimicrobial efficacy is not compromised by the inclusion of 1%-5% wt. of the nonionic surfactant, at the indicated pHs.

Yet further comparative example compositions as well as further compositions of the invention, many of which included 1% wt. and greater amounts (e.g, 5% wt. or more) of detersive surfactants are disclosed on the following further parts of Table C and Table 1 as set forth below. To each of the foregoing a minor amount of an acid, e.g, citric acid, or a base, e.g, tetrahydroxypropyl ethylenediamine or NaOH, may have been added in order to achieve the indicated pH of the respective composition.

TABLE C (Comparative Examples)

|  | C94 | C95 | C96 | C97 |
|---|---|---|---|---|
| CuSO$_4$•5H$_2$O | — | — | — | — |
| ethanol (100%) | — | — | — | — |
| BTC-65 (50%) | 0.2 | 0.2 | 0.2 | 0.2 |
| decyl glucoside | 1.0 | 1.0 | 5.0 | 5.0 |
| di H$_2$O | q.s. | q.s. | q.s. | q.s. |
| pH | 5.01 | 8.14 | 5.26 | 8.27 |
| ASTM E 2315 (log10 reduction) at 1 minute contact tim | Sa > 6.43<br>Ec = 5.13 | Sa > 6.43<br>Ec = 3.54 | Sa = 1.19<br>Ec = 2.51 | Sa = 2.43<br>Ec −1.77 |

TABLE 1

(Examples)

|  | E252 | E253 | E254 | E255 |
|---|---|---|---|---|
| CuSO$_4$•5H$_2$O | 0.1 | 0.1 | 0.1 | 0.1 |
| ethanol (100%) | — | — | — | — |
| BTC-65 (50%) | 0.2 | 0.2 | 0.2 | 0.2 |
| decyl glucoside | 1.0 | 1.0 | 5.0 | 5.0 |
| di H$_2$O | q.s. | q.s. | q.s. | q.s. |
| pH | 5.81 | 7.94 | 5.55 | 8.04 |
| ASTM E 2315 (log10 reduction) at 1 minute contact tim | Sa > 6.43<br>Ec = 6.24 | Sa > 6.43<br>Ec > 6.54 | Sa = 1.64<br>Ec = 2.09 | Sa = 3.38<br>Ec = 2.43 |

As a review of the foregoing two tables confirms, example compositions which included a source of copper ions exhibited an increase of antimicrobial efficacy against both gram positive (viz., S. aureus) and gram negative bacteria (viz., E. coli), when at an alkaline pH even at 5% wt. content of the detersive nonionic surfactant. The foregoing demonstrate that compositions having a source of copper ion source material, and at an alkaline pH provide unexpectedly improved antimicrobial efficacy against challenge microorganisms, particularly gram positive bacteria even when comprising in excess of 1% wt. detersive surfactants, even when ethanol is absent from the compositions, as compared to like or similar comparative compositions which omit the copper ion source material.

Further compositions of the invention, many of which concurrently included several different detersive surfactants are disclosed on the following further part of Table 1 as set forth below; these compositions demonstrated inventive compositions in the format of a hand wash type product, a hand sanitizer type product and/or a bodywash type product.

TABLE 1

(Examples)

|  | E256 | E257 | E258 | E259 |
|---|---|---|---|---|
| $CuSO_4 \cdot 5H_2O$ | 0.1 | 0.1 | — | — |
| $ZnSO4 \cdot 7H2O$ | — | — | 0.12 | 0.12 |
| ethanol (100%) | 9.5 | 9.5 | 9.5 | 9.5 |
| MB-50 (50%) | 0.26 | 0.26 | 0.26 | 0.26 |
| sodium lauroyl sarcosinate (30%) | 0.3 | 0.3 | 0.3 | 0.3 |
| lauramine oxide | 0.2 | 0.2 | 0.2 | 0.2 |
| Polyquaternium-7 | 0.05 | 0.05 | 0.05 | 0.05 |
| NaOH (50%) | as required | as required | as required | as required |
| Citrosol 502 (50%) | as required | as required | as required | as required |
| di $H_2O$ | q.s. | q.s. | q.s. | q.s. |
| pH | 5.21 | 7.85 | 4.75 | 8.11 |
| ASTM E 2315 (log10 reduction), 1 minute contact time | Sa > 6.15 Ec > 5.61 | Sa > 6.15 Ec > 5.61 | Sa > 6.15 Ec > 5.61 | Sa > 6.15 Ec > 5.61 |

The foregoing demonstrate compositions having a high degree of antimicrobial efficacy, a reduced amount of ethanol, and a plurality of different surfactants being present.

Certain further comparative example compositions are disclosed in the following further part of Table C, which are relevant to the next part of Table 1, following.

TABLE C (Comparative Examples)

|  | C98 | C99 | C100 | C101 |
|---|---|---|---|---|
| $CuSO_4 \cdot 5H_2O$ | 0.1 | 0.1 | — | — |
| $ZnSO4 \cdot 7H2O$ | — | — | 0.12 | 0.12 |
| ethanol (100%) | — | — | — | — |
| salicylic acid | 0.3 | 0.3 | 0.3 | 0.3 |
| PCMX | 0.175 | 0.175 | 0.175 | 0.175 |
| decyl glucoside | 15.0 | 15.0 | 15.0 | 15.0 |
| NaOH (50%) | as required | as required | as required | as required |
| Citrosol 502 (50%) | as required | as required | as required | as required |
| di $H_2O$ | q.s. | q.s. | q.s. | q.s. |
| pH | 5.16 | 8.76 | 4.79 | 8.75 |
| ASTM E 2315 (log10 reduction), 1 minute contact time | Sa = 1.79 Ec = 4.69 | Sa = 1.92 Ec = 1.92 | Sa = 2.66 Ec = 4.14 | Sa = 4.14 Ec = 4.64 |

Further compositions of the invention, many of which concurrently included several different detersive surfactants are disclosed on the following further part of Table 1 as set forth below; these compositions demonstrated inventive compositions in the format of a hand wash type product, a hand sanitizer type product and/or a bodywash type product. As compared to the example compositions of the immediately prior part of Table C, these further example compositions demonstrate a surprising improvement in microbicidal effiacay against the tested gram positive and gram negative bacteria, particularly with respect to *S. aureus*.

TABLE 1

(Examples)

|  | E260 | E261 | E262 | E263 |
|---|---|---|---|---|
| $CuSO_4 \cdot 5H_2O$ | 0.1 | 0.1 | — | — |
| $ZnSO4 \cdot 7H2O$ | — | — | 0.12 | 0.12 |
| ethanol (100%) | 15.0 | 15.0 | 15.0 | 15.0 |
| salicylic acid | 0.3 | 0.3 | 0.3 | 0.3 |
| PCMX | 0.175 | 0.175 | 0.175 | 0.175 |
| decyl glucoside | 15.0 | 15.0 | 15.0 | 15.0 |
| NaOH (50%) | as required | as required | as required | as required |
| Citrosol 502 (50%) | as required | as required | as required | as required |
| di $H_2O$ | q.s. | q.s. | q.s. | q.s. |
| pH | 4.96 | 8.70 | 4.71 | 8.74 |
| ASTM E 2315 (log10 reduction), 1 minute contact time | Sa = 5.93 Ec = 5.47 | Sa = 5.69 Ec = 5.47 | Sa = 5.06 Ec = 5.47 | Sa = 5.25 Ec = 5.47 |

Further compositions of the invention are disclosed in the following further part of Table 1; the following may be used as hand sanitizer compositions or may be used in other forms of topical treatment compositions; certain of the following compositions included a thickening agent.

TABLE 1

(Examples)

|  | E264 | E265 | E266 | E267 |
|---|---|---|---|---|
| $CuSO_4 \cdot 5H_2O$ | — | — | 0.1 | 0.1 |
| zinc acetate | 0.1 | 0.1 | — | — |
| ethanol (100%) | 45.0 | 45.0 | 45.0 | 45.0 |
| hydroxypropyl cellulose | — | — | — | — |
| Neutrol TA | as required | as required | as required | as required |
| Citrosol 502(50%) | as required | as required | as required | as required |
| di $H_2O$ | q.s. | q.s. | q.s. | q.s. |
| pH | 4.93 | 8.85 | 4.98 | 8.89 |
| ASTM E 1025 (log10 reduction), 1 minute contact time | PV1 = 4.67 | PV1 = 5.33 | PV1 > 5.83 | PV1 = 5.67 |

|  | E268 | E269 | E270 | E271 |
|---|---|---|---|---|
| $CuSO_4 \cdot 5H_2O$ | 0.099 | 0.099 | — | — |
| zinc acetate | — | — | 0.099 | 0.099 |
| ethanol (100%) | 44.5 | 44.5 | 44.5 | 44.5 |
| hydroxypropyl cellulose | 1.0 | 1.0 | 1.0 | 1.0 |
| Neutrol TA | as required | as required | as required | as required |
| Citrosol 502(50%) | as required | as required | as required | as required |
| di $H_2O$ | q.s. | q.s. | q.s. | q.s. |
| pH | 4.73 | 8.89 | 4.92 | 8.64 |
| Viscosity (cP) | 180 | 370 | 170 | 470 |
| ASTM E 1025 (log10 reduction), 1 minute contact time | PV1 = 4.83 | PV1 = 5.00 | PV1 > 5.83 | PV1 = 5.33 |

As seen from the results reported from the foregoing fragment of Table 1, the compositions exhibited excellent antimicrobial efficacy against Poliovirus type 1, wherein the compositions comprised only 45% wt. ethanol in conjunction with a source of metal ions. The zinc ion containing compositions exhibited somewhat improved microbicidal efficacy when included in alkaline compositions, while the copper ion containing compositions exhibited somewhat improved microbicidal efficacy when included in acidic compositions.

With respect to the reported results of microbicidal efficacy as reported on the foregoing Tables, it is to be understood that each of the identified test protocols were performed according to their published standardized protocols, and the results are reported according to the identified test protocols. For example in the ASTM E 1052, ASTM 1053, EN 131697 tests, the use of the symbol "≥" (greater-than-or-equal-to) or the symbol ">" (greater-than) indicated that the $\log_{10}$ reduction of the challenge microorganism was at least equal to the reported result, but may be greater, while the use of the symbol "=" or the lack of a mathematical operator symbol indicated that the $\log_{10}$ reduction of the challenge microorganism was at least as indicated. In the AOAC Germicidal Spray test, the reported results indicate the number of positive substrates/total substrates, e.g., a result of "0/60" indicates that no positive substrates (survivors) were present within the 60 substrate samples tested.

The invention claimed is:

1. An animate surface treatment composition which imparts a virucidal benefit to a treated animate surface which composition comprises:
    a metal ion source material selected from a copper ion source material which releases Cu(I) and/or Cu(II) ions into the said treatment composition or a zinc ion source material which releases Zn(I) and/or Zn(II) ions into the said treatment composition;
    at least one quaternary ammonium compound which independently of other constituents present exhibits a microbicidal effect;
    about 10% to about 75% wt. of at least one lower alkyl aliphatic monohydric alcohol which independently of other constituents present exhibits a microbicidal effect;
    water; and,
    optionally at least one further detersive surfactant,
    further optionally, one or more further constituents which impart one or more further technical or aesthetic benefits to the composition,
    wherein the treatment composition exhibits a log10 reduction of at least 0.5 against adenovirus and/or poliovirus type 1 (Sabin) ("PV1") when tested according to ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

2. An animate surface treatment composition, which imparts a virucidal benefit to a treated animate surface, which composition comprises:
    a metal ion source material selected from a copper ion source material which releases Cu(I) and/or Cu(II) ions into the said treatment composition or a zinc ion source material which releases Zn(I) and/or Zn(II) ions into the said treatment composition;
    at least one quaternary ammonium compound which independently of other constituents present exhibits a microbicidal effect;
    water; and,
    optionally at least one further detersive surfactant,
    further optionally, one or more further constituents which impart one or more further technical or aesthetic benefits to the composition,
    wherein the treatment composition i exhibits a a log10 reduction of at least 0.5 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension.

3. An animate surface treatment composition which imparts a virucidal benefit to a treated animate surface which composition comprises:
    a metal ion source material selected from a copper ion source material which releases Cu(I) and/or Cu(II) ions into the said treatment composition or a zinc ion source material which releases Zn(I) and/or Zn(II) ions into the said treatment composition;
    at least one lower alkyl aliphatic monohydric alcohol which independently of other constituents present exhibits a microbicidal effect;
    water; and,
    optionally at least one further detersive surfactant,
    further optionally, one or more further constituents which impart one or more further technical or aesthetic benefits to the composition,
    wherein the treatment exhibits a a log10 reduction of at least 0.5 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

4. An animate surface treatment composition according to claim 1 wherein the composition further comprises at least a nonionic detersive surfactant.

5. An animate surface treatment composition comprising a microbicidal control system of constituents which in and of themselves are effective in providing effective control of adenovirus and/or poliovirus type 1 (Sabin) ("PV1"), independently of further and optional constituents, which microbicidal control system of constituents consists essentially of: water, a metal ion source material selected from a copper ion source material which releases Cu(I) and/or Cu(II) ions into the said system and/or a zinc ion source material which releases Zn(I) and/or Zn(II) ions into the said system; at least one lower alkyl aliphatic monohydric alcohol which independently of other constituents in the system exhibits a microbicidal effect and which is present in an amount of at least about 10% wt. of a microbicidal control system of which it forms a part; at least one cationic quaternary ammonium compound which provides a microbicidal benefit independently of the other constituents of the microbicidal control system; and, optionally, a buffer and/or pH adjusting agent, wherein the microbicidal control system exhibits a log10 reduction of at least 0.5 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

6. An animate surface treatment composition comprising a microbicidal control system of constituents which in and of themselves are effective in providing effective control of adenovirus and/or poliovirus type 1 (Sabin) ("PV1"),, independently of further and optional constituents, which microbicidal control system of constituents consists essentially of: water, a metal ion source material selected from a copper ion source material which releases Cu(I) and/or Cu(II) ions into the said system and/or a zinc ion source material which releases Zn(I) and/or Zn(II) ions into the said system; at least one cationic quaternary ammonium compound which provides a microbicidal benefit independently of the other constituents of the microbicidal control system; and, optionally, a buffer and/or pH adjusting agent to impart an appropriate pH for the microbicidal control system wherein the microbicidal control system exhibits a log10 reduction of at least 0.5 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

7. An animate surface treatment composition comprising a microbicidal control system of constituents which in and of themselves are effective in providing effective control adenovirus and/or poliovirus type 1 (Sabin) ("PV1"), independently of further and optional constituents, which microbicidal control system of constituents consists essentially of: water, a metal ion source material selected from a copper ion source material which releases Cu(I) and/or Cu(II) ions into the said system and/or a zinc ion source material which releases Zn(I) and/or Zn(II) ions into the said system; at least one lower alkyl aliphatic monohydric alcohol which independently of other constituents in the system exhibits a microbicidal effect which is present in an amount of at least about 10% wt. of a treatment composition of which it forms a part; and, optionally, a buffer and/or pH adjusting agent to impart an appropriate pH for the microbicidal control system wherein the microbicidal control system exhibits a log10 reduction of at least 0.5 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

8. A method of providing a virucidal benefit to an animate surface, the method comprising the step of applying the animate treatment composition according to claim 1, wherein the animate surface is selected from: skin and/or a keratinous surface and/or hair.

9. An animate surface treatment composition according to claim 1 which consists essentially of:
a metal ion source material selected from a copper ion source material which releases Cu(I) and/or Cu(II) ions into the said treatment composition or a zinc ion source material which releases Zn(I) and/or Zn(II) ions into the said treatment composition;
at least one quaternary ammonium compound which independently of other constituents present exhibits a microbicidal effect;
at least one lower alkyl aliphatic monohydric alcohol which independently of other constituents present exhibits a microbicidal effect;
water; and,
optionally at least one further detersive surfactant,
further optionally, one or more further constituents which impart one or more further technical or aesthetic benefits to the composition.

10. An animate surface treatment composition according to claim 2 which consists essentially of:
a metal ion source material selected from a copper ion source material which releases copper ions into the said treatment composition or a zinc ion source material which releases zinc ions into the said treatment composition;
at least one quaternary ammonium compound which independently of other constituents present exhibits a microbicidal effect;
water; and,
optionally at least one further detersive surfactant,
further optionally, one or more further constituents which impart one or more further technical or aesthetic benefits to the composition.

11. An animate surface treatment composition according to claim 3 which consists essentially of:
a metal ion source material selected from a copper ion source material which releases copper ions into the said treatment composition or a zinc ion source material which releases zinc ions into the said treatment composition;
at least one lower alkyl aliphatic monohydric alcohol which independently of other constituents present exhibits a microbicidal effect;
water; and,
optionally at least one further detersive surfactant,
further optionally, one or more further constituents which impart one or more further technical or aesthetic benefits to the composition.

12. An animate surface treatment composition according to claim 1, which exhibits a log10 reduction of at least about 2 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

13. An animate surface treatment composition according to claim 12, which exhibits a log10 reduction of at least about 3 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

14. An animate surface treatment composition according to claim 13, which exhibits a log10 reduction of at least about 4 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

15. An animate surface treatment composition according to claim 13, which exhibits a log10 reduction of at least about 2 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

16. An animate surface treatment composition according to claim 13, which exhibits a log10 reduction of at least about 3 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

17. An animate surface treatment composition according to claim 16, which exhibits a log10 reduction of at least about 4 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

18. An animate surface treatment composition according to claim 3, which exhibits a log10 reduction of at least about 2 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

19. An animate surface treatment composition according to claim 18, which exhibits a log10 reduction of at least about 3 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

20. An animate surface treatment composition according to claim 19, which exhibits a log10 reduction of at least about 4 against adenovirus and/or poliovirus type 1 (Sabin) ("PV1") when tested according to one or more of the following standardized test protocols: ASTM E1052 Standard Test Method for Efficacy of Antimicrobial Agents against Viruses in Suspension, or ASTM E1053 Standard Test Method to Assess Virucidal Activity of Chemicals Intended for Disinfection of Inanimate, Nonporous Environmental Surfaces.

* * * * *